United States Patent
Braun et al.

(10) Patent No.: US 12,153,051 B2
(45) Date of Patent: *Nov. 26, 2024

(54) REAGENTS FOR QUANTITATIVE MASS SPECTROMETRY

(71) Applicants: President and Fellows of Harvard College, Cambridge, MA (US); Dana-Farber Cancer Institute, Inc., Boston, MA (US)

(72) Inventors: Craig Braun, Cambridge, MA (US); Wilhelm Haas, Cambridge, MA (US); Steven P. Gygi, Cambridge, MA (US); Gregory H. Bird, Boston, MA (US); Loren D. Walensky, Boston, MA (US); Martin Helmut Wuhr, Cambridge, MA (US); Brian K. Erickson, Cambridge, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/626,881

(22) Filed: Apr. 4, 2024

(65) Prior Publication Data

US 2024/0272167 A1  Aug. 15, 2024

Related U.S. Application Data

(63) Continuation of application No. 17/387,888, filed on Jul. 28, 2021, now Pat. No. 11,982,674, which is a continuation of application No. 15/578,382, filed as application No. PCT/US2016/035819 on Jun. 3, 2016, now Pat. No. 11,169,155.

(60) Provisional application No. 62/170,657, filed on Jun. 3, 2015.

(51) Int. Cl.
| C07D 207/46 | (2006.01) |
| C07C 237/22 | (2006.01) |
| C07K 1/13 | (2006.01) |
| C07K 5/02 | (2006.01) |
| G01N 33/58 | (2006.01) |
| G01N 33/68 | (2006.01) |

(52) U.S. Cl.
CPC ........... *G01N 33/58* (2013.01); *C07C 237/22* (2013.01); *C07D 207/46* (2013.01); *C07K 1/13* (2013.01); *C07K 5/0202* (2013.01); *G01N 33/6848* (2013.01); *C07B 2200/07* (2013.01); *G01N 2458/15* (2013.01)

(58) Field of Classification Search
CPC .............................. G01N 33/58; C07C 237/22
See application file for complete search history.

(56) References Cited

U.S. PATENT DOCUMENTS

| 11,105,810 | B2 | 8/2021 | Braun et al. |
| 11,169,155 | B2 * | 11/2021 | Braun ................ G01N 33/6848 |
| 11,982,674 | B2 * | 5/2024 | Braun .................... G01N 33/58 |
| 2010/0167267 | A1 | 7/2010 | Schulzknappe et al. |
| 2011/0207228 | A1 | 8/2011 | Sohn et al. |
| 2014/0364337 | A1 | 12/2014 | Hermanson et al. |
| 2018/0209985 | A1 | 7/2018 | Braun et al. |
| 2020/0174007 | A1 | 6/2020 | Braun et al. |
| 2022/0018847 | A1 | 1/2022 | Braun et al. |
| 2023/0132372 | A9 | 4/2023 | Braun et al. |

FOREIGN PATENT DOCUMENTS

| EP | 2 108 957 A1 | 10/2009 |
| WO | WO 2007 /012849 A2 | 2/2007 |
| WO | WO 2010/104981 A2 | 9/2010 |
| WO | WO 2014/066284 A1 | 5/2014 |

OTHER PUBLICATIONS

Extended European Search Report for Application No. 16804562.3 dated Jan. 16, 2019.
European Office Action mailed Mar. 30, 2020 for Application No. EP 16804562.3.
European Office Action mailed Dec. 18, 2020 for Application No. EP 16804562.3.
Summons to Attend Oral Proceedings mailed Mar. 11, 2022 for Application No. EP 16804562.3.
International Search Report and Written Opinion mailed Sep. 1, 2016 for Application No. PCT/US2016/035819.
International Preliminary Report on Patentability mailed Dec. 14, 2017 for Application No. PCT/US2016/035819.

(Continued)

*Primary Examiner* — Paul V Ward
(74) *Attorney, Agent, or Firm* — Wolf, Greenfield & Sacks, P.C.

(57) ABSTRACT

In some embodiments, a mass spectrometry tag may comprise a linker region, a mass balance region, and a reporter region. The mass spectrometry tag may be configured to fragment in a mass spectrometer via an energy dependent process to produce multiple reporter molecules. For example, the reporter region of the tag may be configured to produce at least two reporter molecules via fragmentation. In some embodiments, one or more regions of the tag may comprise at least one heavy isotope. In some such embodiments, the ability to fragment into multiple reporter molecules as well as the placement and/or number of heavy isotope(s) allows the mass spectrometry tag to be distinguished from other similar mass spectrometry tags. In some such embodiments, the ability to distinguish between tags having the same or substantially similar total mass to charge ratio and reporter region mass may allow the system to have a greater multiplexing capacity than conventional systems.

20 Claims, 17 Drawing Sheets

(56) References Cited

OTHER PUBLICATIONS

Office Action mailed Dec. 31, 2019 for U.S. Appl. No. 15/578,382.
Office Action mailed Jun. 24, 2020 for U.S. Appl. No. 15/578,382.
Office Action mailed Jan. 14, 2021 for U.S. Appl. No. 15/578,382.
Notice of Allowance mailed Apr. 27, 2021 for U.S. Appl. No. 15/578,382.
Office Action mailed Jul. 28, 2020 for U.S. Appl. No. 16/692,762.
Office Action mailed Jan. 19, 2021 for U.S. Appl. No. 16/692,762.
Notice of Allowance mailed Apr. 28, 2021 for U.S. Appl. No. 16/692,762.
Office Action mailed Aug. 31, 2023 for U.S. Appl. No. 17/387,888.
Notice of Allowance mailed Jan. 26, 2024 for U.S. Appl. No. 17/387,888.
Braun et al., Generation of multiple reporter ions from a single isobaric reagent increases multiplexing capacity for quantitative proteomics. Anal Chem. Oct. 6, 2015;87(19):9855-63. doi: 10.1021/acs.analchem.5b02307.
Gung, Mass Spectrometry: Fragmentation. University of Miami. Presentation Created Jan. 30, 2017. http://chemistry.miamioh.edu/gung/CHM526/pdfs/Mass-fragmentation.pdf.
Hebert et al., Amine-reactive neutron-encoded labels for highly plexed proteomic quantitation. Mol Cell Proteomics. 2013;12(11):3360-3369.
Herzog, Isotope. Britannica Online Encyclopedia. Accessed Dec. 10, 2019: 1-29. https://www.britannica.com/print/article/296583.
Mcalister et al., Increasing the multiplexing capacity of TMTs using reporter ion isotopologues with isobaric masses. Anal Chem. Sep. 4, 2012;84(17):7469-78. doi: 10.1021/ac301572t.
McAlister et al., MultiNotch MS3 enables accurate, sensitive, and multiplexed detection of differential expression across cancer cell line proteomes. Anal Chem. Jul. 15, 2014;86(14):7150-8. doi: 10.1021/ac502040v.
Ross et al., Multiplexed protein quantitation in saccharomyces cerevisiae using amine-reactive isobaric tagging reagents. Molecular & Cellular Proteomics. Sep. 22, 2004;3(12):1154-1169.
Wühr et al., Accurate multiplexed proteomics at the MS2 level using the complement reporter ion cluster. Analytical Chemistry. Oct. 25, 2012;84(21):9214-9221.
U.S. Appl. No. 17/387,888, filed Jul. 28, 2021, Braun et al.
EP 16804562.3, Jan. 16, 2019, Extended European Search Report.
EP 16804562.3, Mar. 30, 2020, European Office Action.
PCT/US2016/035819, Sep. 1, 2016, International Search Report and Written Opinion.
PCT/US2016/035819, Dec. 14, 2017, International Preliminary Report on Patentability.

\* cited by examiner $$\text{Fractional Contribution Tag A} = \frac{175}{172 + 173 + 174 + 175}$$

$$\text{Fractional Contribution Tag E} = \frac{126}{126 + 127 + 128}$$

$$\text{Fractional Contribution Tag F} = \frac{172}{172 + 173 + 174 + 175}$$

$$\text{Fractional Contribution Tag C} = \frac{173}{172 + 173 + 174 + 175} - FC(E)$$

$$\text{Fractional Contribution Tag B} = \frac{127}{126 + 127 + 128} - FC(F)$$

$$\text{Fractional Contribution Tag D} = \frac{174}{172 + 173 + 174 + 175} - FC(B)$$

| Isotopes/Tag | 13C Only | | 13C 15N (Single) | | 13C 15N (Both) | 13C 15N (Both) O18 |
|---|---|---|---|---|---|---|
| | TMT | CMT | TMT | CMT | CMT | CMT |
| 1 | 2 | 3 | 3 | 5 | 5 | 5 |
| 2 | 3 | 5 | 5 | 9 | 10 | 12 |
| 3 | 4 | 7 | 7 | 13 | 15 | 21 |
| 4 | 5 | 9 | 9 | 17 | 20 | 31 |
| 5 | 6 | 11 | 11 | 21 | 25 | 41 |

REAGENTS FOR QUANTITATIVE MASS SPECTROMETRY

This application is a continuation application of U.S. application Ser. No. 17/387,888, filed Jul. 28, 2021, which is a continuation application of U.S. application Ser. No. 15/578,382, filed Jun. 20, 2018, which is a national stage filing under 35 U.S.C. § 371 of International Application No. PCT/US2016/035819, filed Jun. 3, 2016, which claims the benefit of U.S. Provisional Patent Application Ser. No. 62/170,657, filed Jun. 3, 2015, each of which is incorporated herein by reference in its entirety.

TECHNICAL FIELD

Reagents for quantitative mass spectrometry and related systems and methods are generally described.

BACKGROUND

Mass spectrometry is a technique that analyzes a sample by identifying the mass-to-charge ratio of constituent parts of the sample. Mass spectrometry (MS) has many applications in the study of proteins, known as proteomics. MS may be used to characterize and identify proteins in a sample or to quantify the amount of particular proteins in a sample. In the last decade, instrumentation and methodological improvements have allowed mass spectrometry based proteomics to significantly mature, allowing for the identification of entire proteomes and their post-translational modifications. The field of quantitative MS-based proteomics has emerged as a powerful technique for interrogating the proteome-based mechanisms underlying phenotypic differences. A variety of MS approaches for quantitative proteomics have been developed, including metabolic labeling, chemical labeling, and label-free approaches. Two particularly attractive strategies, owing to their compatibility with essentially any sample origin, are label-free methods and chemical labeling. While label-free approaches require the least amount of sample manipulation and are applicable to a wide array of MS instruments, lack of parallelization introduces throughput limitations and can impact quantitative measurement precision and accuracy. In contrast, heavy isotope-labeled samples behave identically during chromatographic separation, ionization, and detection, allowing sample mixing at the beginning of the experimental workflow for simultaneous analysis in a single MS run. However, such heavy isotope tagging systems have limited multiplexing capacity. Accordingly, improved systems and methods are needed.

SUMMARY

Reagents for quantitative mass spectrometry and related systems and methods are generally described. The subject matter of the present invention involves, in some cases, interrelated products, alternative solutions to a particular problem, and/or a plurality of different uses of one or more systems and/or articles.

In one set of embodiments, mass spectrometry tags are provided. In one embodiment, a mass spectrometry tag comprises Formula (I):

$$L-Q-R' \qquad (I)$$

wherein:
L is a linker region comprising a reactive group;
Q is a mass balance region; and
R' is a reporter region, and wherein at least one of Q or R' comprises a stable heavy isotope and the tag is configured to fragment under dissociation conditions in a mass spectrometer to produce fragments comprising a primary reporter ion and a secondary reporter ion.

In another set of embodiments, compounds are provided. In one embodiment, a compound comprises Formula (II):

$$M-T-Q-R' \qquad (II)$$

wherein:
M is a biological molecule;
T is a tethering region;
Q is a mass balance region; and
R' is a reporter region, and wherein at least one of Q or R' comprises a stable heavy isotope and the compound is configured to fragment under dissociation conditions in a mass spectrometer to produce fragments comprising a primary reporter ion and a secondary reporter ion.

In one embodiment, a compound comprises Formula (III):

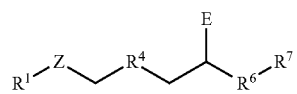

or a isotopic analogue thereof,
wherein:
$R^1$ is selected from the group consisting of optionally substituted alkyl, optionally substituted acyl, optionally substituted aryl, and optionally substituted heteroaryl;
Z is a nucleophilic group;
$R^4$ is absent or selected from the group consisting of optionally substituted alkylene and optionally substituted heteroalkylene;
E is a leaving group;
$R^6$ is selected from the group consisting of optionally substituted alkylene and optionally substituted heteroalkylene; and
$R^7$ is a reactive group.

In one set of embodiments, systems are provided. In one embodiment, a system comprises a plurality of distinguishable mass spectrometry tags comprising a first tag comprising a first reporter region and a second tag comprising a second reporter region, wherein the first and second tags comprise one or more isotopes, and wherein the difference between the molecular weight of the first reporter region and the second reporter region is indistinguishable via mass spectrometry.

In another embodiment, a system comprises a set of mass spectrometry tags, wherein each tag of the set is configured to fragment under dissociation conditions in a mass spectrometer to produce at least two reporter ions.

In one embodiment, a system comprises a set of mass spectrometry tags comprising reporter regions, wherein the set comprises distinguishable isotopomeric reporter regions and isotopologous reporter regions.

In another embodiment, a system comprises a set of mass spectrometry tags comprising one or more isotopes, wherein the multiplexing capacity is greater than 2.2.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
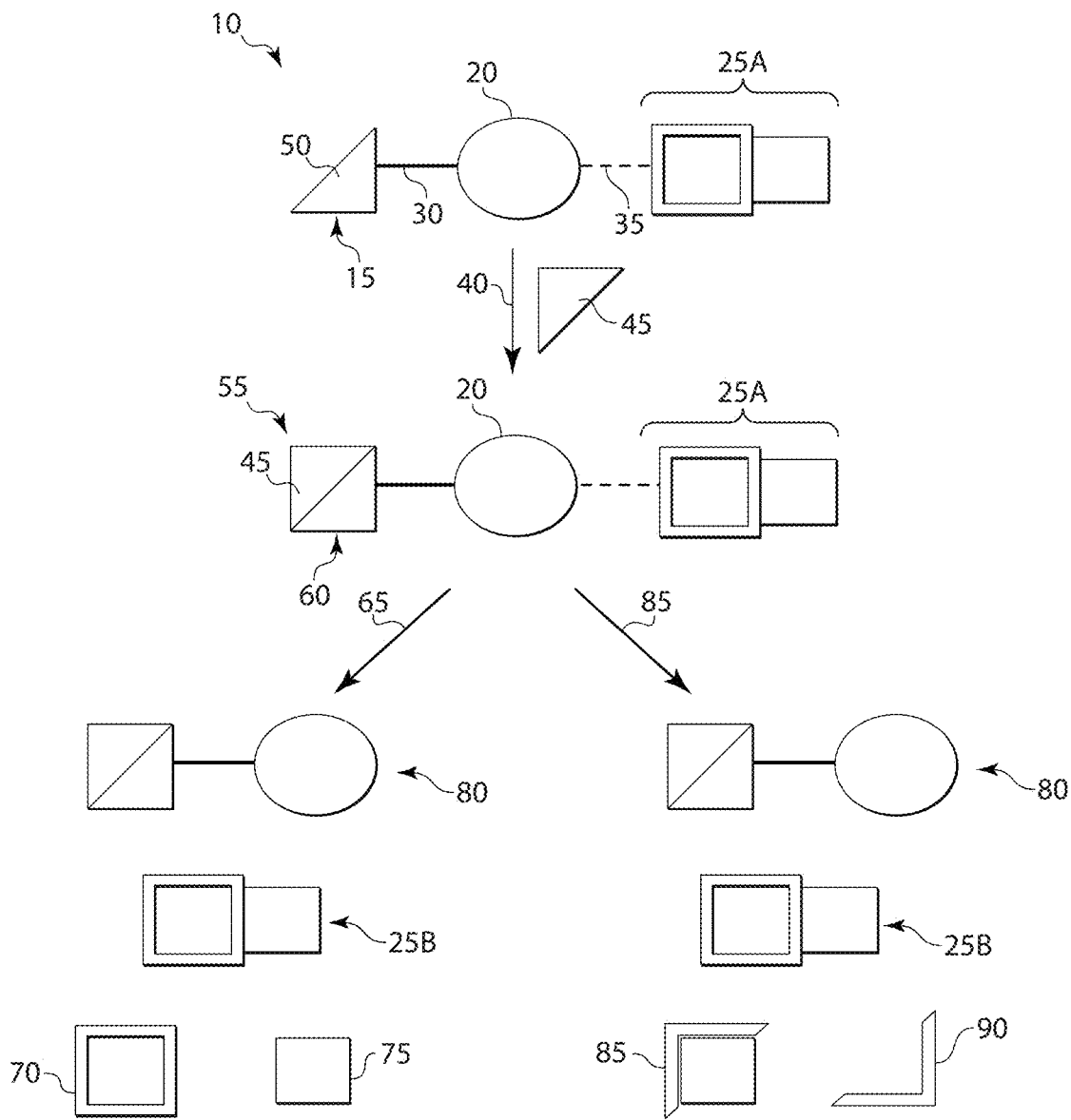
FIG. 1A is a schematic of a mass spectrometry tag and a fragmentation process, according to one set of embodiments.

In some embodiments, a mass spectrometry tag may comprise a linker region, a mass balance region, and a reporter region. The mass spectrometry tag may be configured to fragment in a mass spectrometer under dissociation conditions to produce multiple reporter ions. For example, the reporter region of the tag may be configured to produce at least two reporter ions (e.g., a primary reporter ion, a secondary reporter ion) via fragmentation. In some embodiments, one or more regions (e.g., mass balance region, reporter region) of the tag may comprise at least one stable heavy isotope. In some such embodiments, the ability to fragment into multiple reporter ions as well as the placement and/or number of stable heavy isotope(s) allows the mass spectrometry tag to be distinguished from other similar mass spectrometry tags. For instance, such a mass spectrometry tag may be distinguishable from another tag having the same or substantially similar (e.g., indistinguishable via mass spectrometry) total mass to charge ratio and reporter region mass. In some embodiments, the mass spectrometry tags, described herein, may be used in a system for labeling an analyte in samples. In some such embodiments, the ability to distinguish between tags having the same or substantially similar (e.g., indistinguishable via mass spectrometry) total mass to charge ratio and reporter region mass to charge ratio may allow the system to have a greater multiplexing capacity than conventional systems.

While a variety of mass spectrometry based techniques have been used to determine analytes (e.g., biological molecules) in a sample, nominal isobaric and isobaric labeling have proven to be an accurate, reliable, and sensitive quantitative technique for determining an analyte in one or more samples. Conventional isobaric labeling utilizes a set of mass spectrometry tags having the same or a substantially similar (e.g., indistinguishable via mass spectrometry) molecular weight, which can co-migrate in chromatographic separation, to label an analyte in different samples. In conventional isobaric labeling, each isobaric tag has a reporter region with a different molecular weight from the other isobaric tags in the set. Fragmentation of the tag results in the cleavage of the bond anchoring the reporter region to the tag. The sample origin and relative abundance of an analyte may be determined based on the location and intensity, respectively, of the reporter region peak on the mass spectrum.

As used herein, "isobaric" refers to molecules that have the same accurate mass. In some instances, molecules having a mass that is indistinguishable via mass spectrometry may be referred to as isobaric.

As used herein, "nominal isobaric" refers to molecules that have the same nominal mass. The nominal mass of an ion or molecule is calculated using the integer mass of the most abundant isotope of each element. A set of nominal isobaric molecules may include isobaric molecules.

The differences in the molecular weight of the reporter regions in an isobaric set of tags are often achieved using stable heavy isotopes. In some instances, a conventional isobaric set includes tags comprising reporter regions that are isotopic analogues, also known as isotopologues, of other reporter regions in the set. In order to produce a set of tags having the same or substantially similar (e.g., indistinguishable via mass spectrometry) molecular weight, conventional isobaric tags may comprise a mass balancing region. In such cases, the combined molecular weight of the mass balance region and the reporter region are the same or substantially similar for at least a portion (e.g., all) of the tags in an isobaric set.

As used herein, "isotopologues" refer to molecules that differ only in isotopic composition (number of isotopic substitutions), e.g. $CH_4$, $CH_3D$, $CH_2D_2$.

Many conventional isobaric labeling systems have limited multiplexing capacity. As used herein, "multiplexing capacity" refers to the maximum number of distinguishable tags per number of isotopes that can be generated for a given tag structure. The multiplexing capacity is related (e.g., linearly) to the maximum number of distinguishable tags per the molecular weight of the tags and determines the maximum number of samples that may be processed in a single stream. In many conventional isobaric labeling systems, restraints on the molecular weight of the tags, due to the inverse relationship between tag molecular weight and sensitivity, limit the total number of isotopes that can be used in a tag, and accordingly the multiplexing capacity.

It has been discovered, within the context of certain embodiments of the present invention, that a mass spectrometry tag comprising a reporter region capable of fragmenting into at least two distinguishable reporter ions may be used to increase the multiplexing capacity in mass spectrometer tag systems (e.g., isobaric labeling system). More distinguishable tags are produced for a given number of isotopes due, at least in part, to the ability to generate multiple distinguishable tags having the same reporter region mass to charge ratio. For instance, unlike conventional isobaric labeling systems, reporter regions that are isotopic isomers (also known as isotopomers) can be distinguished using the tags, systems, and methods described herein.

As used herein, "isotopomers" refer to isomers having the same number of each isotopic atom but differing in their positions. In some instances, the isotopomers may be constitutional isomers (e.g. $CH_2DCH=O$ and $CH_3CD=O$).

Figure 1B:
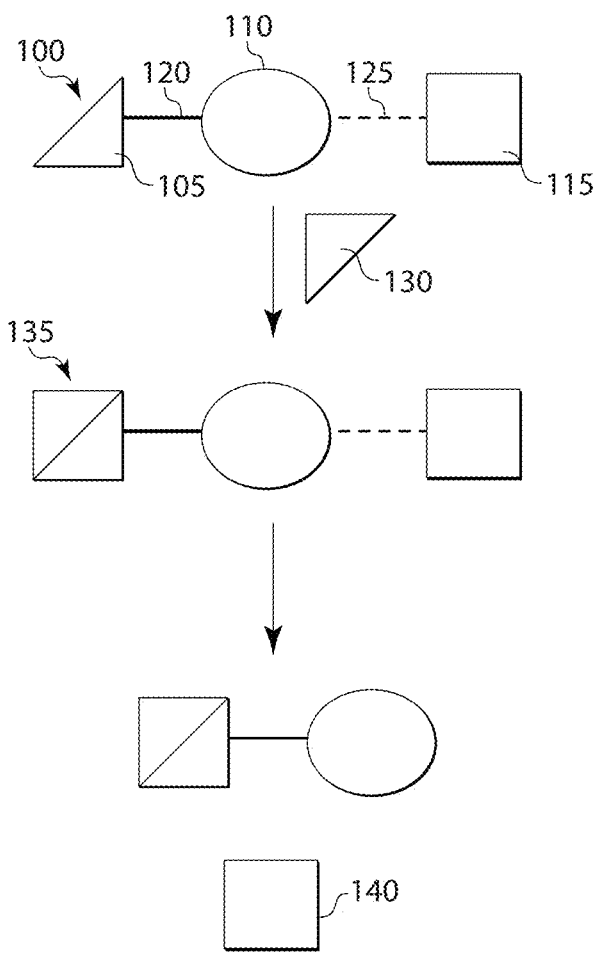
FIG. 1B is a schematic of a conventional mass spectrometry tag and a fragmentation process.

Non-limiting examples of a mass spectrometry tag, described herein, and a conventional isobaric mass spectrometry tag are shown in FIG. 1A and FIG. 1B, respectively. FIG. 1A is a schematic of a mass spectrometry tag 10 comprising a linker region 15, a mass balance region 20, and a reporter region 25A. The linker region 15 may be connected to mass balance region 20 via bond 30. In some embodiments, bond 30 may not be susceptible to cleavage under dissociation conditions in the mass spectrometer as indicated by the solid line in FIG. 1A. In other embodiments, bond 30 may be susceptible to cleavage. Mass balance region 20 may be positioned between the linker region and the reporter region as shown in FIG. 1A. The mass balance region may be connected to reporter region 25A via bond 35. In some embodiments, bond 35 may be susceptible to cleavage under dissociation conditions in the mass spectrometer as indicated by the dashed line in FIG. 1A. It should be understood that the regions of the mass spectrometry tag need not be connected as shown in FIG. 1A and the susceptibility of the bonds in the tag to cleavage in dissociation conditions may depend on the position of the regions within the tag. For instance, the linker region may be positioned between the reporter region and the mass balance region. In some such cases, the linker may be bound to the reporter region via a cleavable bond. Alternatively, the reporter region may be positioned between the mass balance region and the linker region. In some such cases, the reporter region may be bound to the other regions via cleavable bonds.

In some embodiments, as indicated by arrow 40, the tag may be exposed to analyte 45. The linker region may comprise a reactive group 50 capable of associating with (e.g., via a covalent bond) the analyte. The reactive group may associate with the analyte and tether the tag to the analyte forming a labeled analyte 55. The association between the reactive group and the analyte may convert the linker region into a tethered region 60. After the analyte is labeled with the tag, the labeled analyte may be exposed to dissociation conditions in a mass spectrometer. In some such embodiments, the tag may produce fragments comprising at least two reporter ions. In some embodiments, as indicated by arrow 65, the fragments may primarily be formed via cleavage of susceptible bonds, as described in more detail below. In some such embodiments, bond 35 may be broken thereby releasing reporter region 25A to form free reporter region 25B and complement region 80. At least a portion of the reporter region may fragment to from ions 70 and 75. In some embodiments, the free reporter region may serve as a primary reporter ion and ion 70 and/or ion 75 may serve as additional reporter ions. In certain embodiments, the free reporter region, ion 70, and/or ion 75 may not be a reporter ion. For example, the mass to charge ratio of ion 75 may be relatively small, such that it does not fall within the region typically used for determination of the analyte and/or may not be accurately identified.

In some embodiments, as indicated by arrow 85, the fragments may be formed via cleavage of susceptible bonds and one or more chemical reactions of the reporter region, as described in more detail below. In some such embodiments, bond 35 is cleaved to form free reporter region 25B and complement region 80. At least some of free reporter region 25 may undergo one or more chemical reactions (e.g., an intramolecular reaction) to form ion 85 and 90. In some instances, as illustrated in FIG. 1A, free reporter region 25B may undergo one or more chemical reactions that comprise an elimination step, which reduces the molecular weight of the free reporter region and produces ion 85. In such cases, ion 90 may be the eliminated portion of free reporter region 25B. In some embodiments, free reporter region 25B may serve as a primary reporter ion and ion 85 and/or ion 90 may serve as additional reporter ions. In certain embodiments, free reporter region 25B, ion 85, and/or ion 90 may not be a reporter ion. For instance, ion 90 may not be a reporter ion due, e.g., to one or more of the reasons described above with respect to ion 75.

An example of a conventional isobaric tag is shown in FIG. 1B. FIG. 1B is a schematic of a conventional mass spectrometry tag 100 comprising a linker region 105, a mass balance region 110, and a reporter region 115. The linker region 105 may be connected to mass balance region 110 via bond 120. Bond 120 may not be susceptible to cleavage under dissociation conditions in the mass spectrometer as indicated by the solid line in FIG. 1B. The mass balance region may be connected to reporter region 115 via bond 125. Bond 125 may be susceptible to cleavage under dissociation conditions in the mass spectrometer as indicated by the dashed line in FIG. 1B. The tag may be exposed to analyte 130 to from a labeled analyte 135. After the analyte is labeled with the tag, the labeled analyte may be exposed to dissociation conditions in a mass spectrometer. In some such embodiments, tag 100 fragments to produce a single reporter ion 140.

In some embodiments, a mass spectrometry tag (e.g., tag 10) comprises Formula (I):

L—Q—R'     (I)

wherein:
L is a linker region comprising a reactive group;
Q is a mass balance region; and
R' is a reporter region.

In certain embodiments, at least one of Q or R' comprises one or more stable heavy isotopes (e.g., at least two stable heavy isotopes, at least three stable heavy isotopes, at least five stable heavy isotopes). In some instances, each of Q and R' comprise at least one stable heavy isotope. Non-limiting examples of suitable stable heavy isotopes include $^{2}H$, $^{13}C$, $^{15}N$, $^{18}O$, $^{33}S$, and $^{34}S$. In some cases, at least one of Q or R' (e.g., both) comprises $^{13}C$, $^{15}N$, and/or $^{18}O$. In some instances, at least one of Q or R' (e.g., each) comprises $^{13}C$ and $^{15}N$. In certain embodiments, the one or more stable heavy isotopes in the tag are selected from the group consisting of $^{13}C$, $^{15}N$, $^{18}O$, $^{33}S$, and $^{34}S$. In some instances, the stable heavy isotopes in the tag are selected from the group consisting of $^{13}C$, $^{15}N$, and $^{18}O$. In certain cases, the stable heavy isotopes in the tag are selected from the group consisting of $^{13}C$ and $^{15}N$. In certain cases, the stable heavy isotopes in the tag consist essentially of $^{13}C$. It should be understood that Q and R' may comprise the same or different stable heavy isotopes.

In some embodiments, the tag may be configured to fragment under dissociation conditions (e.g., collision induced dissociation) in a mass spectrometer. In some such embodiments, one or more bonds within the tag may be selected to have a bond dissociation energy that is less than or equal to the energy (e.g., collision energy) produced during dissociation conditions in the mass spectrometer. In such cases, cleavage of the one or more bonds occurs under dissociation conditions. For instance, the Q-R bond may be selected to have a bond dissociation energy that is less than or equal to about the energy generated under dissociation conditions in the mass spectrometer. In certain embodiments, one or more bonds within the tag may be designed to not be susceptible to cleavage by the dissociation conditions in the mass spectrometer. For instance, the L-Q bond may be configured to resist dissociation and/or not dissociate under the dissociation conditions.

In general, the dissociation energy of the bonds within the tag may be configured such that the fragments produced under dissociation conditions may comprise at least two reporter ions (e.g., primary reporter ions and secondary reporter ions) and/or complement ions. For instance, cleavage of the Q-R' bond may produce a primary reporter ion (e.g., primary reporter ion) and at least a portion of the primary reporter ion may further react and/or fragment under the conditions in the mass spectrometer to produce a secondary reporter ion and, optionally, a tertiary reporter ion.

Non-limiting examples of bonds that may have dissociation energies less than or equal to the energy generated under dissociation conditions, described herein, include amide bonds, ester bonds, and bonds that are alpha to carbonyl bonds.

Non-limiting examples of bonds that may have a dissociation energies greater than the energy generated under dissociation conditions, described herein, include carbon-carbon bonds.

In some embodiments, at least one of Q or R' comprises a charged group and/or a functional group that becomes charged as part of a fragmentation process in a mass spectrometer. In certain embodiments, R' comprises one or more charged groups and/or functional groups that becomes charged as part of a fragmentation process in a mass spectrometer. For instance, Q and/or R' may comprise a functional group that is a Lewis base. In some embodiments, at least one of Q or R' comprises a nitrogen containing functional group. In some instances, each of Q and R' comprise the same or different nitrogen containing functional group. Non-limiting examples of nitrogen containing functional groups include amides, amines, imines, imides, azides, and nitriles. In some embodiments, at least one of Q or R' (e.g., R') comprises an amine (e.g., primary amine, secondary amine, tertiary amine). In certain embodiments, Q and/or R' comprises two or more nitrogen containing functional groups. For instance, R' may comprise at least two nitrogen containing functional groups that are the same or different (e.g., two amines; an amine and an imine). Those of ordinary skill in the art would be knowledgeable of suitable functional and charged groups.

As noted above, the mass spectrometry tags, described herein, are designed to produce two or more reporter ions under dissociation conditions in a mass spectrometer. Without being bound by theory, it is believed that at least a portion of the reporter regions (e.g., free reporter regions, reporter regions within the tag) undergoes fragmentation and/or one or more chemical reactions to generate additional reporter ions (e.g., secondary reporter ion, tertiary reporter ion). For example, after cleavage of the Q-R' bond, at least a portion of the free reporter regions in the mass spectrometer may undergo one or more chemical reactions (e.g., intramolecular ring forming reaction) to generate additional distinguishable reporter ions (e.g., secondary reporter ions, tertiary reporter ions). In some embodiments, cleavage of the Q-R' bond may produce a functional group that participates in the one or more chemical reactions. For instance, the bond cleavage may produce a nucleophile, electrophile, radical, or a leaving group.

In some embodiments, one or more (e.g., all) chemical reactions may be an intramolecular chemical reaction. In certain embodiments, the reporter region may undergo at least one intermolecular chemical reaction. In other embodiments, the reporter region may not undergo an intermolecular chemical reaction. Non-limiting examples of suitable chemical reactions include substitution reactions, rearrangement reactions, elimination reactions, and cyclization reactions. In some embodiments, the reporter region may be designed to undergo one or more intramolecular and/or intermolecular reaction. For instance, the spacing of functional groups that participate in the chemical reactions may be selected to allow for an energetically favorable chemical reaction. For example, the reporter region may be designed to allow for formation of energetically favorable ring structures (e.g., five-membered rings, six-membered rings) via one or more intramolecular reactions.

As another example, one or more bonds in the reporter region may be configured to have a bond dissociation energy less than or equal to about the energy generated under dissociation conditions in the mass spectrometer, such that prior to, during, or after cleavage of the Q-R' bond, the reporter region breaks into one or more fragments. In some such embodiments, one or more fragments produced from the reporter region may be a distinguishable reporter ion.

It should be understood that, in some embodiments, the reporter region may not comprise bonds having bond dissociation energies that allow for cleavage under dissociation conditions.

In some embodiments, a mass spectrometry tag may be designed to produce two reporter ions. In certain embodiments, a mass spectrometry tag may be designed to produce three reporter ions. In some such embodiments, a tertiary reporter ion may be used to increase the precision of a system of mass spectrometry tags by, e.g., generating additional linear equations to describe the system of reporter ions already solved in a 2-reporter ion system. Such an overdetermined system would be deconvolved by means of an 'ordinary least squares' regression model to fit the data. Comparing the measurement variability across each channel with and without this additional data will allow one to set tertiary ion signal intensity thresholds above which these corrections are useful. In some embodiments, a tertiary reporter ion may be used to increase multiplexing capacity.

As described herein, the mass spectrometry tag is configured to produce a plurality of distinguishable reporter ions upon exposure to dissociation conditions in a mass spectrometer. In some embodiments, reporter ions may be distinguishable based on their molecular weight:charge ratio. In general, a reporter ion comprises one or more charged groups. In some embodiments, one or more reporter ions may be positively charged or negatively charged. For instance, one or more reporter ion (e.g., primary reporter ion, secondary reporter ion) may be positively charged. For example, one or more reporter ions may comprise a quaternary amine. As used herein, the term "charged group" has its ordinary meaning in the art and may refer to a molecule comprising one or more charged moiety. As used herein, a "charged moiety" is a chemical moiety that carries a formal electronic charge, e.g., monovalent (+1), divalent (+2), trivalent (+3), etc. The charged moiety may be anionic (i.e., negatively charged) or cationic (i.e., positively charged). Examples of negatively-charged groups or precursors thereof, include carboxylate groups, sulfonate group, sulfate groups, phosphonate groups, phosphate groups, and the like. Examples of positively-charged moieties include amino groups (e.g., primary, secondary, tertiary amines, quaternary amines), carbocation groups (e.g., carbeniums) ammonium groups, pyridinium group, and imidazolium groups. The charge of the charged moiety may vary, in some cases, with the environmental conditions, for example, changes in mass spectrometry may alter the charge of the moiety, and/or cause the moiety to become charged or uncharged.

In some embodiments, one or more reporter ions (e.g., primary reporter ion, secondary reporter ion) comprises one or more stable heavy isotopes (e.g., at least two stable heavy isotopes, at least three stable heavy isotopes, at least five stable heavy isotopes). In some instances, the primary reporter ion comprises at least one stable heavy isotopes. In certain cases, a secondary reporter ion comprises at least one stable heavy isotope. In some cases, one or more stable heavy isotopes in the reporter ion(s) are selected from the group consisting of $^{2}$H, $^{13}$C, $^{15}$N, $^{18}$O, $^{33}$S, and $^{34}$S. In certain cases, one or more stable heavy isotopes in the reporter ion(s) are selected from the group consisting of $^{13}$C, $^{15}$N, and/or $^{18}$O. In some instances, one or more stable heavy isotopes in the reporter ion(s) are selected from the group consisting of $^{13}$C and $^{15}$N. In some cases, the reporter ion(s) comprises one or more $^{13}$C. It should be understood that each reporter ion may comprise the same or different stable heavy isotopes and may comprise the same or a different number of stable heavy isotope. In some embodiments, one or more reporter ion may not comprise a stable heavy isotope.

In some embodiments, the mass spectrometry tag may include a linker region comprising a reactive group. The reactive group may be designed to associate with an analyte. For instance, the reactive group may be capable of reacting with a functional group in the analyte to produce a covalent bond.

In some embodiments, the association between the mass spectrometry tag and the analyte may produce a compound of Formula (II):

wherein:
M is an analyte;
T is a tethering region;
Q is the mass balance region described above; and
R' is the reporter region described above.

In some embodiments, the association between the reactive group in the linker region to the analyte may serve to tether the analyte to the tag and thereby converting the linker region to a tethering region. In general, the tether region refers to the group formed from the association between the reactive group and the analyte. Non-limiting examples of reactive groups which can be used to form the tether include esters, amides, amines, ethers, ureas, carbamates, carbonates, and anhydride moieties.

In some embodiment, a mass spectrometry tag comprises Formula (III):

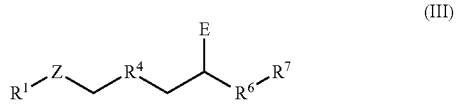

or a isotopic analogue thereof,
wherein:
$R^1$ is selected from the group consisting of optionally substituted alkyl, optionally substituted acyl, optionally substituted aryl, and optionally substituted heteroaryl;
Z is a nucleophilic group;
$R^4$ is absent or selected from the group consisting of optionally substituted alkylene and optionally substituted heteroalkylene;
E is a leaving group;
$R^6$ is selected from the group consisting of optionally substituted alkylene and optionally substituted heteroalkylene; and
$R^7$ is a reactive group.

As used herein, a "leaving group" is given its ordinary meaning in the art of synthetic organic chemistry and refers to an atom or a group of atoms capable of being displaced by a nucleophile during a chemical reaction. Examples of suitable leaving groups include, but are not limited to, halides (such as chloride, bromide, and iodide), thiols, amines (e.g., tertiary amine, quaternary amine), acyl groups, alkoxy groups, alkanesulfonyloxy, arenesulfonyloxy, alkylcarbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. In some embodiments, the leaving group in Formula (III) is selected from the group consisting of optionally substituted thiol, optionally substituted amino, optionally substituted acyl, and optionally substituted heteroalkyl. In certain embodiments, the leaving group is an amine group (e.g., tertiary amine, quaternary amine). Those of ordinary skill in the art would be able to select which leaving groups may be suitable for use in the invention.

As used herein, the terms "nucleophilic group" and "nucleophile" are given their ordinary meaning in the art and refers to a chemical moiety having a reactive pair of electrons. A nucleophilic group may include any species capable of donating electrons, generally resulting in formation of a bond, such as a covalent bond. The nucleophile may comprise, for example, a heteroatom such as oxygen, nitrogen, or phosphorous, or other atoms capable of donating electrons to form a bond. In some cases, the nucleophile may comprise an electron-donating group, such as amino, alkoxy (e.g., methoxy), heteroaryl, and the like. In some cases, the nucleophile may comprise a heteroalkyl or heteroaryl group, optionally substituted. For example, the nucleophilic group in Formula (III) may be —NH—, —O—, or —S—.

In some embodiments, $R^7$ is a reactive group as described herein. As used, herein, the term "reactive group" refers to a group or moiety which is capable of being chemically modified (e.g., via chemical reaction with a compound comprising a functional group). In some embodiments, the reactive group is a group or moiety which is capable of being chemically modified with a functional group of an analyte via formation of a bond (e.g., covalent bond, non-covalent bond, etc.) or interaction (e.g., chemical or biological interaction) between the reactive group and the functional group of an analyte (e.g., amine). In some embodiments, the reactive group may be selected from the group consisting of optionally substituted alkyl (e.g., haloalkyl), optionally substituted heteroalkyl (e.g., alkoxy), substituted cycloheteroalkyl (e.g., succinimides), optionally substituted heteroalkenyl, optionally substituted heteroaryl, alcohol, optionally substituted amino, optionally substituted acyl, and optionally substituted thiol. In certain embodiments, the reactive group may be selected from the group consisting of optionally substituted alkyl (e.g., haloalkyl), optionally substituted heteroalkyl (e.g., alkoxy), substituted cycloheteroalkyl, alcohol, optionally substituted amino, optionally substituted acyl, and optionally substituted thiol. Non-limiting examples of specific reactive groups include amines, hydroxysuccinimides, hydroxysulfosuccinimides, maleimides, thiocyanates, iodoalkanes, ketones, and aldehydes. Reactive groups will be selected readily, by those of ordinary skill in the art, based upon the description provided herein and knowledge in the art.

In some embodiments, the reactive group is a group or moiety which is capable of being chemically modified with a functional group via formation of a covalent bond. For instance, in certain embodiments, the chemical reaction may be a coupling reaction or a substitution reaction. Those of ordinary skill in the art will be aware of suitable chemical reactions between a reactive group and the functional group of an analyte. Non-limiting examples of chemical reactions include addition reactions (including cycloaddition), oxidation reactions, reduction reactions, elimination reactions, substitution reactions, rearrangement reactions, polymerization reactions, transition-metal catalyzed coupling or cross-coupling reactions, and olefin metathesis. It should be understood that covalent bonds may be formed by other types of reactions, as known to those of ordinary skill in the art, using reactive groups described herein.

In some embodiments, the reactive group is a group or moiety which is capable of being chemically modified with a functional group via formation of a non-covalent bond (e.g., via hydrogen-bonds, ionic bonds, dative bonds, Van der Waals interactions, or the like). In some embodiments, the functional group may form a hydrogen-bond with another molecule. Reactive groups capable of forming hydrogen-bonds include hydrogen-bond donors and acceptors. Those of ordinary skill in the art will be able to identify hydrogen-bond donors and acceptors suitable for use in the present invention. For example, a hydrogen-bond donor may comprise at least one hydrogen atom capable of associating with a pair of electrons on a hydrogen-bond acceptor to form the hydrogen bond. In some cases, the reactive groups may comprise one or more hydrogen-bond donor/acceptor moieties. Other examples of reactive groups which may form hydrogen bonds include carbonyl groups, amines, hydroxyls, and the like. In some cases, the reactive groups may comprise an electron-rich or electron-poor moiety may form an electrostatic interaction with another molecule.

In some embodiments, the reactive group is a group or moiety which is capable of being chemically modified with a functional group via a biological binding event (i.e., between complementary pairs of biological molecules). For example, a molecule may include an entity such as biotin that specifically binds to a complementary entity, such as avidin or streptavidin, on the binding partner. Other examples of biological molecules that may form biological bonds between pairs of biological molecules include, but are not limited to, proteins, nucleic acids, glycoproteins, carbohydrates, hormones, and the like. Specific examples include, but are not limited to, an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Biological interactions between a molecule and a binding partner suitable for use in the embodiments described herein can be selected readily, by those of ordinary skill in the art, based upon the description herein as their function, examples of such biological interactions, and knowledge herein and in the art as to simple techniques for identifying suitable chemical interactions.

In some embodiments, $R^1$ in Formula (III) is selected from the group consisting of optionally substituted alkyl, optionally —C(=O)$R^2$, optionally substituted aryl, and optionally substituted heteroaryl, wherein $R^2$ is selected from the group consisting of optionally substituted alkyl, optionally substituted heteroalkyl, optionally substituted aryl, and optionally substituted heteroaryl. In certain embodiments, $R^1$ in Formula (III) is selected from the group consisting of optionally substituted alkyl, optionally substituted —C(=O)$R^2$, optionally substituted aryl, and optionally substituted heteroaryl, wherein $R^2$ is selected from the group consisting of optionally substituted alkyl and optionally substituted heteroalkyl. In some instances, $R^1$ in Formula (III) is selected from the group consisting of optionally substituted alkyl, optionally substituted —C(=O)$R^2$, optionally substituted aryl, and optionally substituted heteroaryl, wherein $R^2$ is selected from the group consisting of optionally substituted alkyl. In certain case, $R^1$ in Formula (III) is selected from the group consisting of optionally substituted alkyl and optionally substituted —C(=O)$R^2$, wherein $R^2$ is selected from the group consisting of optionally substituted alkyl.

In some embodiments, the leaving group in Formula (III) is selected from the group consisting of optionally substituted thiol, optionally substituted amine, optionally substituted acyl, and optionally substituted heteroalkyl (e.g., alkoxy group). In certain embodiments, the leaving group is an optionally substituted amine (e.g., tertiary amine, quaternary amine).

In some embodiments, $R^7$ in Formula (III) is selected from the group consisting of optionally substituted heteroalkyl, substituted cycloheteroalkyl, optionally substituted heteroalkenyl, optionally substituted heteroaryl, alcohol, optionally substituted acyl, and optionally substituted thiol.

In some embodiments, $R^6$ in Formula (III) is selected from the group consisting of optionally substituted alkylene and optionally substituted heteroalkylene, wherein $R^6$ is optionally substituted with oxo. In certain embodiments, $R^6$ in Formula (III) comprises 0-10 substituents and wherein at least some (e.g., all) of the substituents are oxo.

It should be understood that as used herein, alkyl and/or heteroalkyl groups may comprise any suitable number of atoms. For instance, in some embodiments, alkyl and/or heteroalkyl may be $C_{1-10}$ (e.g., $C_{1-5}$, $C_{1-3}$).

In certain embodiment, a mass spectrometry tag of Formula (III) has the structure:

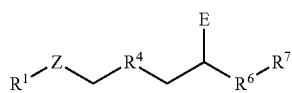

or a isotopic analogue thereof,
wherein:
$R^1$ is selected from the group consisting of optionally substituted alkyl, optionally substituted —C(=O)$R^2$, optionally substituted aryl, and optionally substituted heteroaryl;

$R^2$ is selected from the group consisting of optionally substituted alkyl, optionally substituted heteroalkyl, optionally substituted aryl, and optionally substituted heteroaryl;

Z is selected from the group consisting of —NH—, —O—, and —S—;

$R^4$ is absent or selected from the group consisting of optionally substituted alkylene and optionally substituted heteroalkylene;

E is selected from the group consisting of optionally substituted thiol, optionally substituted amino, optionally substituted acyl, and optionally substituted heteroalkyl;

$R^6$ is selected from the group consisting of optionally substituted alkylene, and optionally substituted heteroalkylene; and $R^7$ is selected from the group consisting of optionally substituted heteroalkyl, substituted cycloheteroalkyl, optionally substituted heteroalkenyl, optionally substituted heteroaryl, alcohol, optionally substituted acyl, and optionally substituted thiol.

In some embodiments, $R^1$ is as described above with respect to a mass spectrometry tag of Formula (III). In some such embodiments, Z is —NH—. In certain embodiments, $R^7$ is selected from the group consisting of optionally substituted heteroalkyl, substituted cycloheteroalkyl, alcohol, optionally substituted acyl, and optionally substituted thiol.

In certain embodiment, a mass spectrometry tag of Formula (III) has the above structure:

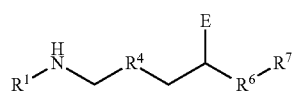

or a isotopic analogue thereof,
wherein:
$R^1$ is selected from the group consisting of optionally substituted alkyl, optionally substituted —C(=O)$R^2$, optionally substituted aryl, and optionally substituted heteroaryl;

$R^2$ is selected from the group consisting of optionally substituted alkyl, optionally substituted heteroalkyl, optionally substituted aryl, and optionally substituted heteroaryl;

$R^4$ is absent or selected from the group consisting of optionally substituted alkylene and optionally substituted heteroalkylene;

E is selected from the group consisting of optionally substituted thiol, optionally substituted amino, optionally substituted acyl, and optionally substituted heteroalkyl;

$R^6$ is selected from the group consisting of optionally substituted alkylene and optionally substituted heteroalkylene; and $R^7$ is selected from the group consisting of optionally substituted heteroalkyl, substituted cycloheteroalkyl, optionally substituted heteroalkenyl, optionally substituted heteroaryl, alcohol, optionally substituted acyl, and optionally substituted thiol.

In some embodiments, $R^1$ is as described above with respect to a mass spectrometry tag of Formula (III). In certain embodiments, $R^7$ is selected from the group consisting of optionally substituted heteroalkyl, substituted cycloheteroalkyl, alcohol, optionally substituted acyl, and optionally substituted thiol.

In certain embodiment, a mass spectrometry tag of Formula (III) has the above structure:

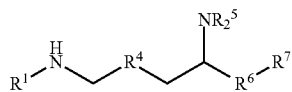

or a isotopic analogue thereof,
wherein:
- $R^1$ is selected from the group consisting of optionally substituted alkyl, optionally substituted —C(=O)$R^2$, optionally substituted aryl, and optionally substituted heteroaryl;
- $R^4$ is absent or selected from the group consisting of optionally substituted alkylene and optionally substituted heteroalkylene;
- each $R^5$ is the same or different and selected from the group consisting of optionally substituted alkyl and optionally substituted heteroalkyl, optionally two $R^5$ may be joined to form a ring;
- $R^6$ is selected from the group consisting of optionally substituted alkylene and optionally substituted heteroalkylene; and
- $R^7$ is selected from the group consisting of optionally substituted heteroalkyl, substituted cycloheteroalkyl, optionally substituted heteroalkenyl, optionally substituted heteroaryl, alcohol, optionally substituted acyl, and optionally substituted thiol.

In some embodiments, $R^1$ is as described above with respect to a mass spectrometry tag of Formula (III). In certain embodiments, $R^7$ is selected from the group consisting of optionally substituted heteroalkyl, substituted cycloheteroalkyl, alcohol, optionally substituted acyl, and optionally substituted thiol.

In some embodiments, a mass spectrometry tag of Formula (III) may have the structure:

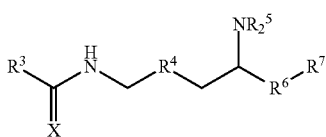

or a isotopic analogue thereof,
wherein:
- $R^3$ is optionally substituted alkyl;
- X is O or N;
- $R^4$ is absent or selected from the group consisting of optionally substituted alkylene and optionally substituted heteroalkylene;
- each $R^5$ is the same or different and selected from the group consisting of optionally substituted alkyl and optionally substituted heteroalkyl, optionally two $R^5$ may be joined to form a ring;
- $R^6$ is selected from the group consisting of optionally substituted alkylene and optionally substituted heteroalkylene; and
- $R^7$ is a reactive group.

In some embodiments, $R^6$ is the mass balance region Q and $R^7$ is the linker region L. In some embodiments, X is O. In some instances, X is N. In certain embodiments, $R^4$ is optionally substituted alkylene. In other instances, $R^4$ is optionally substituted heteroalkylene. In some embodiments, $R^4$ is absent.

In certain embodiments, a mass spectrometry tag of Formula (III) may have the structure:

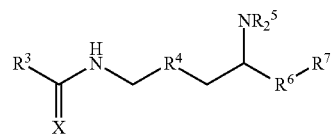

or a isotopic analogue thereof,
wherein:
- $R^3$ is optionally substituted $C_{1-10}$ alkyl;
- X is O or N;
- $R^4$ is absent or selected from the group consisting of optionally substituted $C_{1-5}$ alkylene and optionally substituted hetero $C_{1-5}$ alkylene;
- each $R^5$ is the same or different and is selected from the group consisting of optionally substituted $C_{1-10}$ alkyl and optionally substituted hetero $C_{1-10}$ alkyl, optionally two $R^5$ may be joined to form a ring;
- $R^6$ is selected from the group consisting of optionally substituted $C_{1-10}$ alkylene and optionally substituted hetero $C_{1-10}$ alkylene; and
- $R^7$ is a reactive group.

In some embodiments, X is O. In other instances, X is N. In certain embodiments, $R^4$ is optionally substituted optionally substituted $C_{1-5}$ alkylene. In other instances, $R^4$ is optionally substituted hetero $C_{1-5}$ alkylene. In some embodiments, $R^4$ is absent.

In some embodiments a mass spectrometry tag of Formula (III) may have the structure:

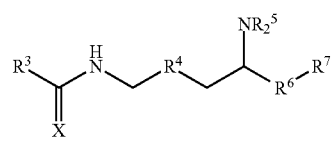

or a isotopic analogue thereof,
wherein:
- $R^3$ is optionally substituted $C_{1-10}$ alkyl;
- X is O or N;
- $R^4$ is absent or $C_{1-5}$ alkylene;
- each $R^5$ is the same or different and is selected from the group consisting of optionally substituted $C_{1-10}$ alkyl and optionally substituted hetero $C_{1-10}$ alkyl, optionally two $R^5$ may be joined to form a ring;
- $R^6$ is selected from the group consisting of optionally substituted $C_{1-10}$ alkylene and optionally substituted hetero $C_{1-10}$ alkylene; and
- $R^7$ is a reactive group.

In some such embodiments, $R^6$ is optionally substituted hetero $C_{1-10}$ alkylene and/or X is O.

In some embodiments, a mass spectrometry tag of Formula (III) may have the structure:

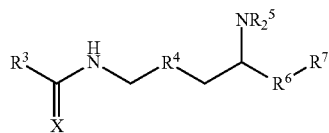

or a isotopic analogue thereof,
wherein:
  $R^3$ is optionally substituted $C_{1-5}$ alkyl;
  X is O or N;
  $R^4$ is absent or $C_{1-5}$ alkylene;
  each $R^5$ is the same or different and is selected from the group consisting of optionally substituted $C_{1-5}$ alkyl and optionally substituted hetero $C_{1-5}$ alkyl, optionally two $R^5$ may be joined to form a ring;
  $R^6$ is optionally substituted hetero $C_{1-10}$ alkylene; and
  $R^7$ is a reactive group.

In some embodiments, the mass spectrometry tag of Formula (III) has a structure selected from the group consisting of:

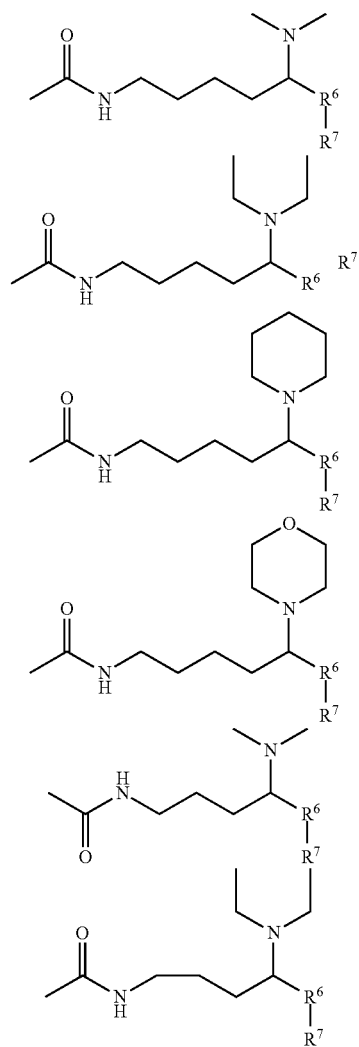

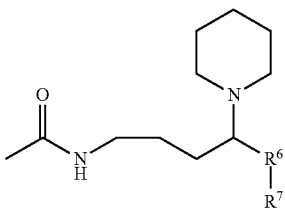

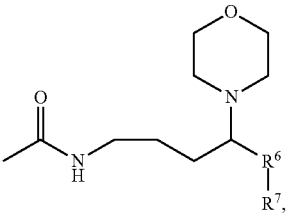

and isotopic isomers thereof,
wherein:
  $R^6$ is selected from the group consisting of optionally substituted alkylene and optionally substituted heteroalkylene, as described herein; and
  $R^7$ is a reactive group, as described herein.

In some embodiments, the mass spectrometry tag of Formula (III) has a structure selected from the group consisting of:

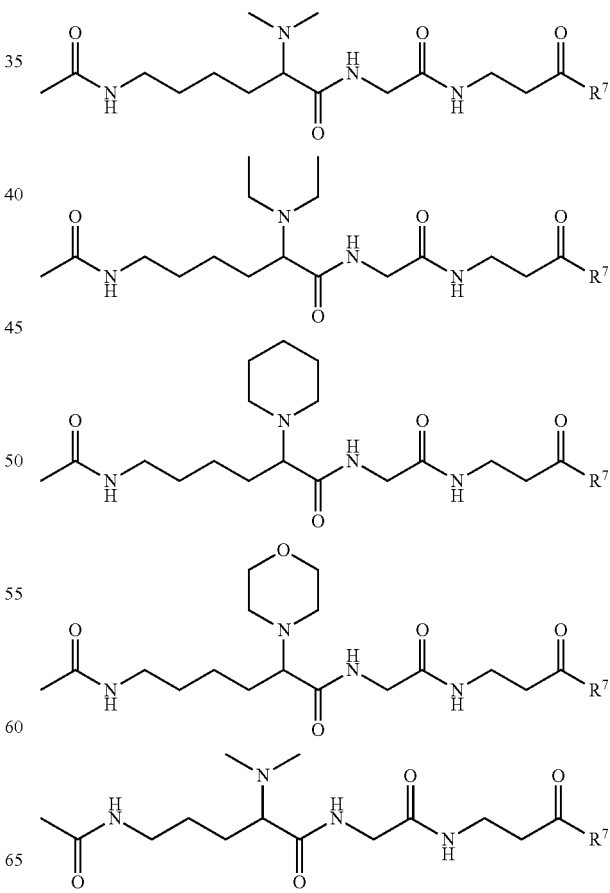

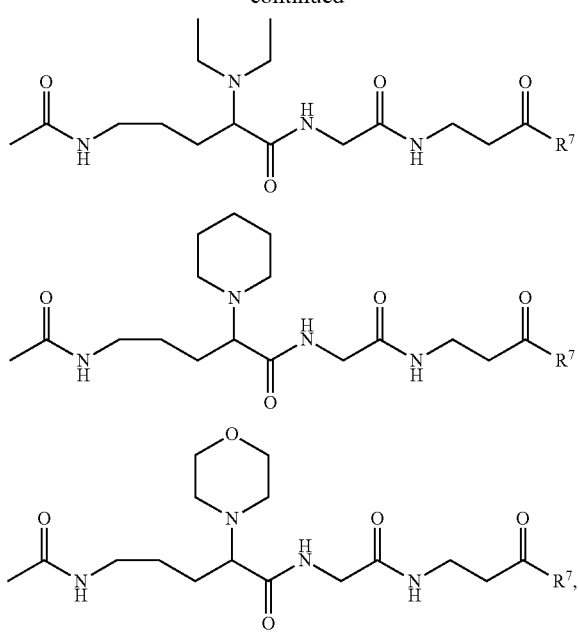

and isotopic analogues thereof, wherein R[7] is a reactive group, as described herein. In some embodiments, R[7] is selected from the group consisting of optionally substituted alkyl (e.g., haloalkyl), optionally substituted heteroalkyl (e.g., alkoxy), substituted cycloheteroalkyl (e.g., succinimides), optionally substituted heteroalkenyl, optionally substituted heteroaryl, alcohol, optionally substituted amino, optionally substituted acyl, and optionally substituted thiol. In some embodiments, R[7] is

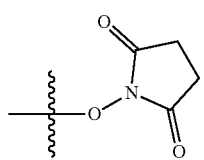 [SMILES: *ON1C(=O)CCC1=O]

or —OH.

In some embodiments, the mass spectrometry tag of Formula (III) has a structure selected from the group consisting of:

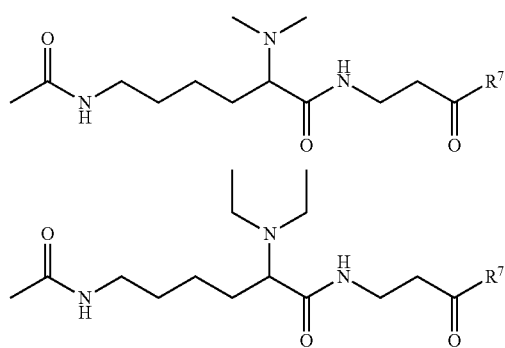

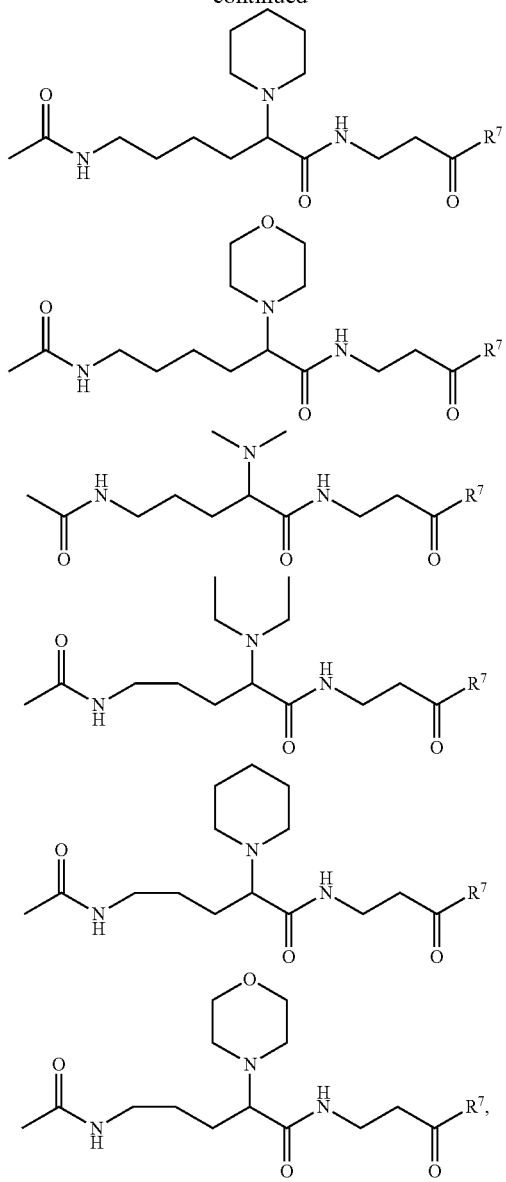

and isotopic analogues thereof, wherein R[7] is a reactive group, as described herein. In some embodiments, R[7] is selected from the group consisting of optionally substituted alkyl (e.g., haloalkyl), optionally substituted heteroalkyl (e.g., alkoxy), substituted cycloheteroalkyl (e.g., succinimides), optionally substituted heteroalkenyl, optionally substituted heteroaryl, alcohol, optionally substituted amino, optionally substituted acyl, and optionally substituted thiol. In some embodiments, R[7] is

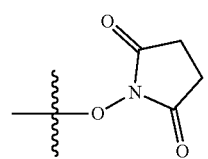 [SMILES: *ON1C(=O)CCC1=O]

or —OH.

In some embodiments, the mass spectrometry tag of Formula (III) has a structure selected from the group consisting of:

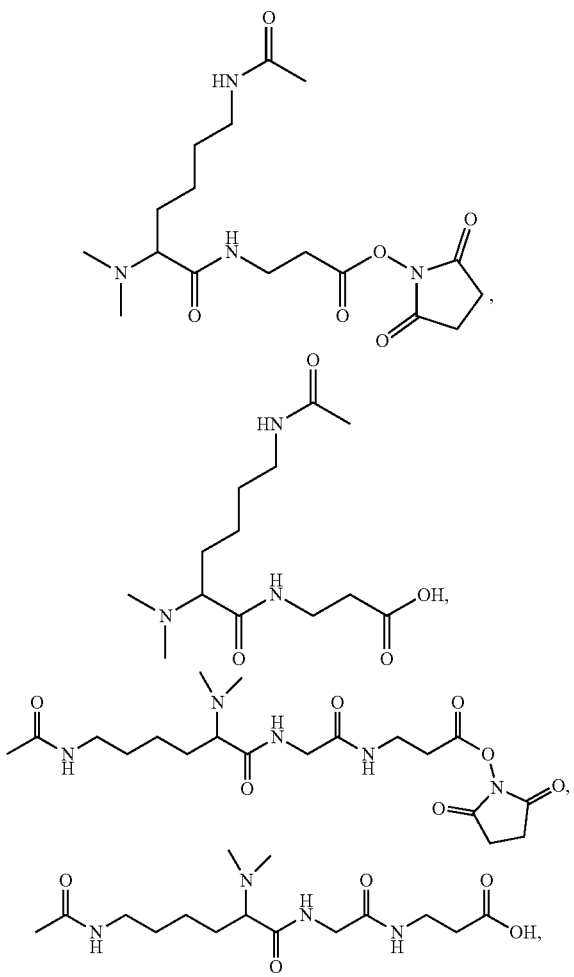

and isotopic isomers thereof.

In some embodiments, a set of mass spectrometry tags, described herein, may be used to form a set for a mass spectrometry labeling system. In some such embodiments, at least a portion of the tags in the set may have the same or a substantially similar (e.g., indistinguishable via mass spectrometry) molecular weight. In certain embodiments, one or more tags (e.g., each tag) of the set are configured to fragment under dissociation conditions to produce at least two reporter ions (e.g., reporter ions). In some embodiments, the ability to produce multiple reporter ions may allow isobaric tags to comprise distinguishable isotopomeric reporter regions and isotopologous reporter regions.

Figure 2A:
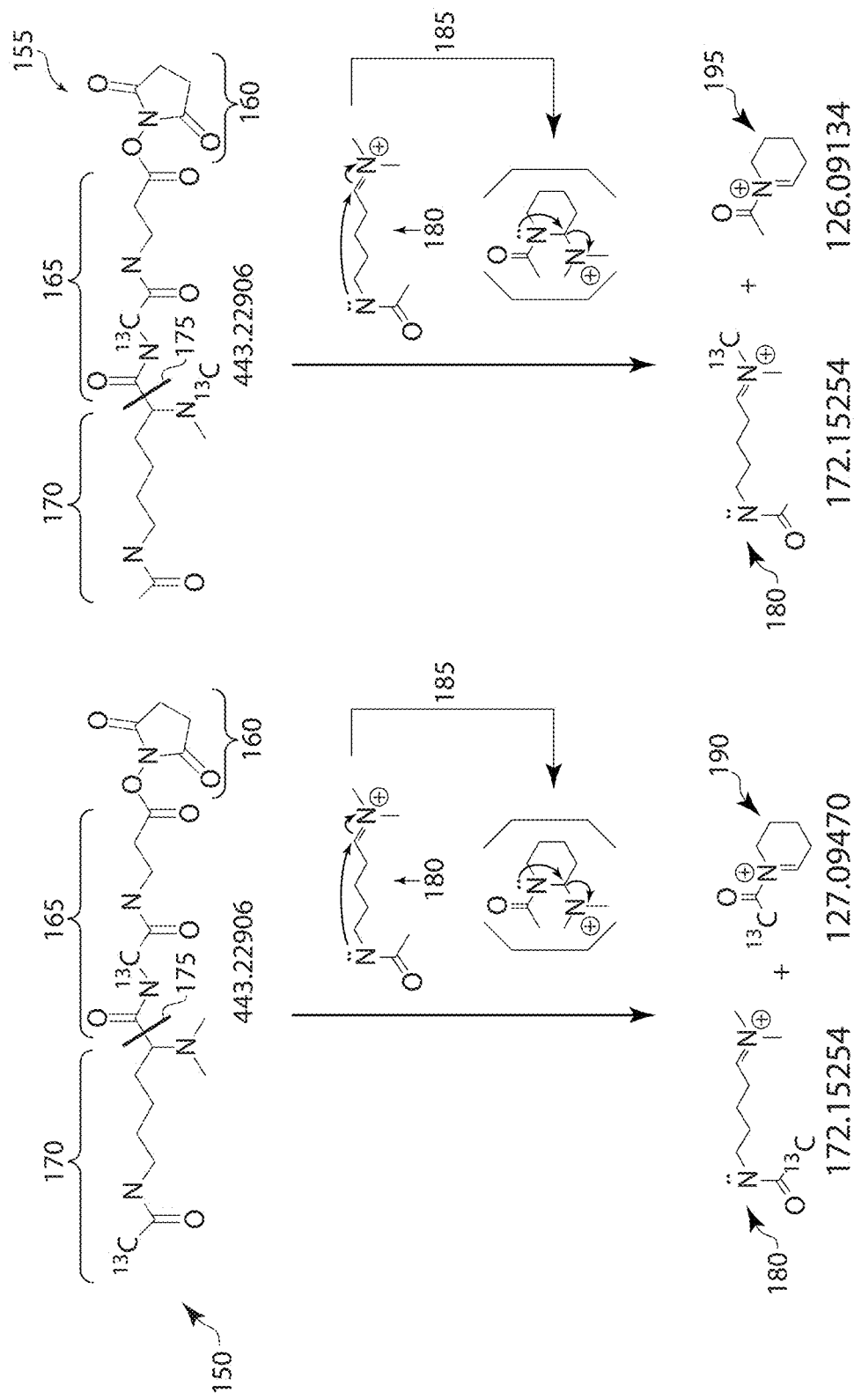
FIG. 2A is a mass spectrometry tag and associated reporter ions, according to one set of embodiments.
Figure 2B:
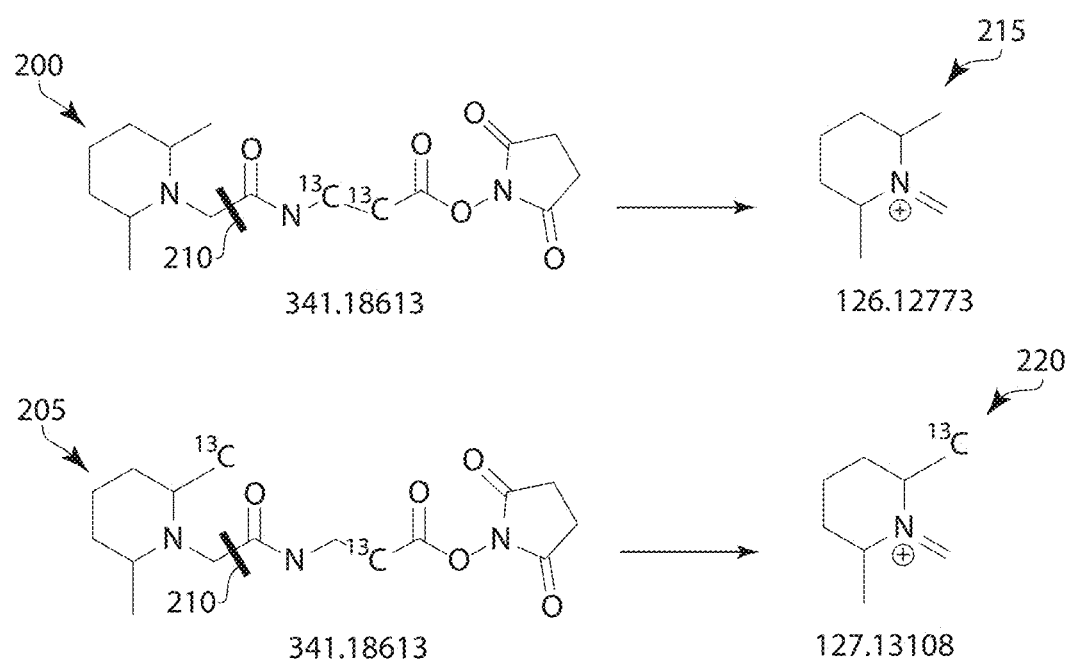
FIG. 2B is a conventional mass spectrometry tag and the reporter ion, according to certain embodiments.

A non-limiting of a set a mass spectrometry tags, described herein, and a non-limiting example of a set of conventional isobaric mass spectrometry tags are shown in FIG. 2A and FIG. 2B, respectively. FIG. 2A shows tag 150 and an isotopic isomer of tag 150, tag 155. Tags 150 and 155 may have the same total molecular weight, reporter region molar weight, and linker region 160, but differ in the position of stable heavy isotopes in the mass balance region 165 and the reporter region 170 as shown in FIG. 2A. Tags 150 and 155 may also comprise bond 175, which is susceptible to cleavage under dissociation conditions. In some embodiments, tags 150 and 155 may undergo the same fragmentation mechanism as illustrated in FIG. 2A. In other embodiments, tags 150 and 155 may undergo different fragmentation schematic mechanisms. In some embodiments, under dissociation conditions, bond 175 may cleave to form primary reporter ion 180 (e.g., primary reporter ion). At least some of the primary reporter ion may undergo a chemical reaction, as indicated by arrow 185, to produce a secondary reporter ion (e.g., secondary reporter ion). In certain embodiments, the secondary reporter ion 190 formed from tag 150 and the secondary reporter ion 195 formed from tag 155 are distinguishable by mass due at least in part to the position of the stable heavy isotopes in tags 150 and 155. As shown in FIG. 2A, secondary reporter ion 190 comprises a heavy stable isotope due to the placement of isotopes in tag 150. Conversely, secondary reporter ion 195 does not comprise a heavy stable isotope due to the placement of isotopes in tag 155. The difference in molecular weight of the secondary reporter ions based on the presence or absence of a stable heavy isotope allows the secondary reporter ions to be distinguished, and accordingly isobaric tags 150 and 155 having isotopic isomeric reporter regions to be distinguished.

A non-limiting example of a set of conventional isobaric mass spectrometry tags are shown in FIG. 2B. FIG. 2B shows isobaric tags 200 and 205. Tags 200 and 205 may have the same molecular weight, but differ in molecular weight of the reporter region as shown in FIG. 2B. Tags 200 and 205 may also comprise bond 210, which is susceptible to cleavage under dissociation conditions. In some embodiments, under dissociation conditions, bond 210 may cleave to form a single reporter ion 215 from tag 200 and 220 from tag 205. Neither tag 200 or 205 undergoes a chemical reaction, as described herein.

As described herein, in some embodiments, the mass spectrometry tags may have a relatively high multiplexing capacity compared to conventional isobaric labeling techniques. For instance, in some exemplary embodiments, the maximum number of distinguishable tags per total number of isotopes when the tag comprises C and N stable heavy isotopes is $((C+1)(N+1)-(2N-1))*RIS-(RIS-1)$, wherein C is the number of carbon stable heavy isotopes, N is the number of nitrogen stable heavy isotopes, and RIS is the number of reporter ion series (e.g., 1—only primary reporter ions, 2—primary and secondary reporter ions, 3—primary, secondary, and tertiary reporter ions), assuming that each heavy isotope can be placed on either the primary or secondary reporter regions and that only two reporter ion series are used for quantification. In some exemplary embodiments in which only carbon and nitrogen stable heavy isotopes are used in a tag, the maximum number of distinguishable tags per total number of isotopes in a tag, described herein, may be $(C+1)(N+1)*2-1$, assuming that all carbon and nitrogen heavy isotopes can be placed on either the primary or secondary reporter ion regions of the tag and that only two reporter ion series are used for quantification. Conversely, the maximum number of distinguishable tags per total number of isotopes in a conventional isobaric tag, such as Tandem Mass Tag™, may be $(C+1)(N+1)$.

In some embodiments, the multiplexing capacity of a set of isobaric mass spectrometry tags may be greater than or equal to about 2.5, greater than or equal to about 3, greater than or equal to about 4, greater than or equal to about 5, greater than or equal to about 6, or greater than or equal to about 8. In some instances, the multiplexing capacity of a set of isobaric mass spectrometry tags is between about 2.5 and about 10, between about 3 and about 10, between about 4 and about 10, between about 3 and about 8, or between about 4 and about 8.

Figure 3A:
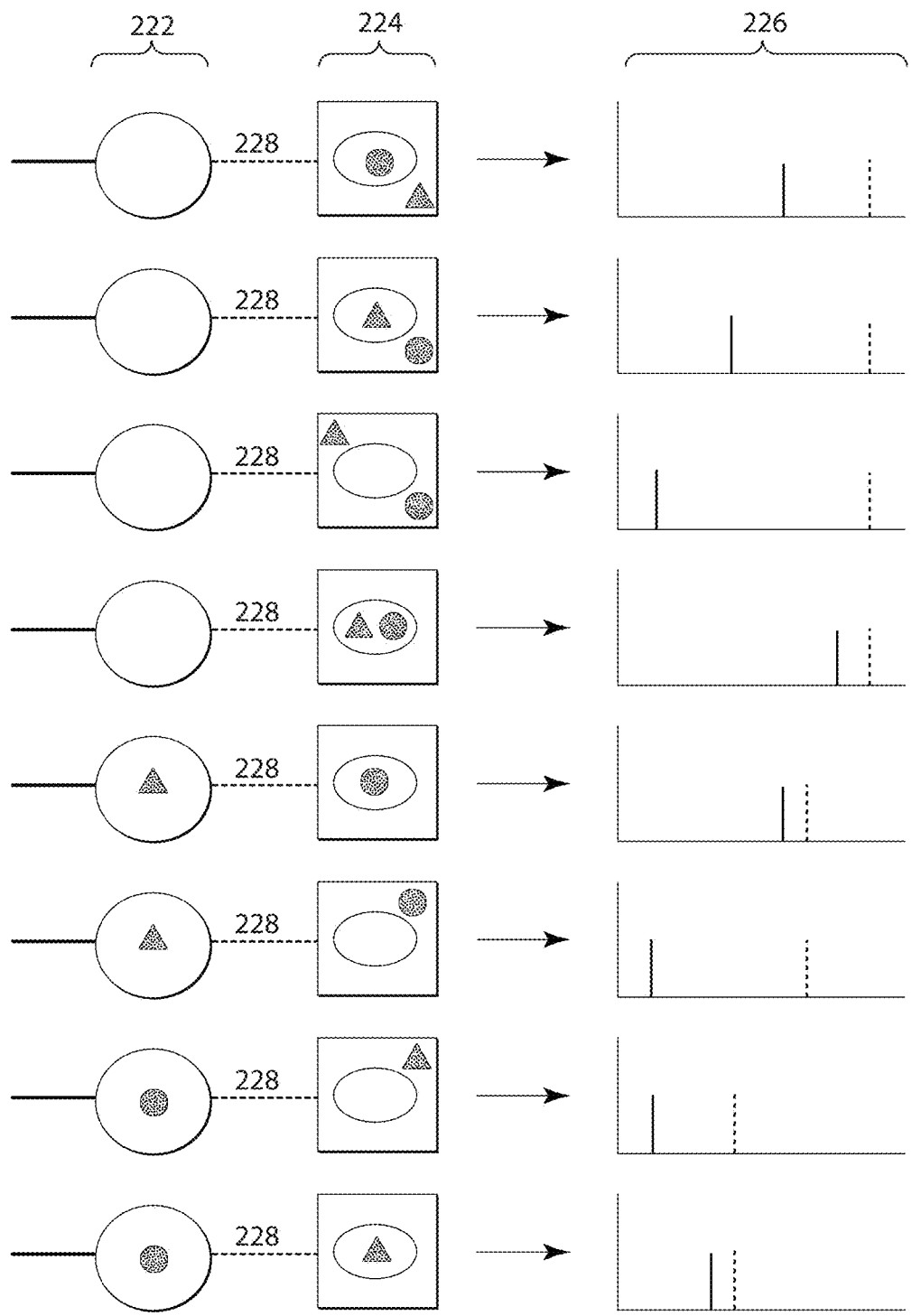
FIG. 3A is a schematic of the multiplexing capacity for a mass spectrometry tag containing two different isotopes, according to one set of embodiments.
Figure 3B:
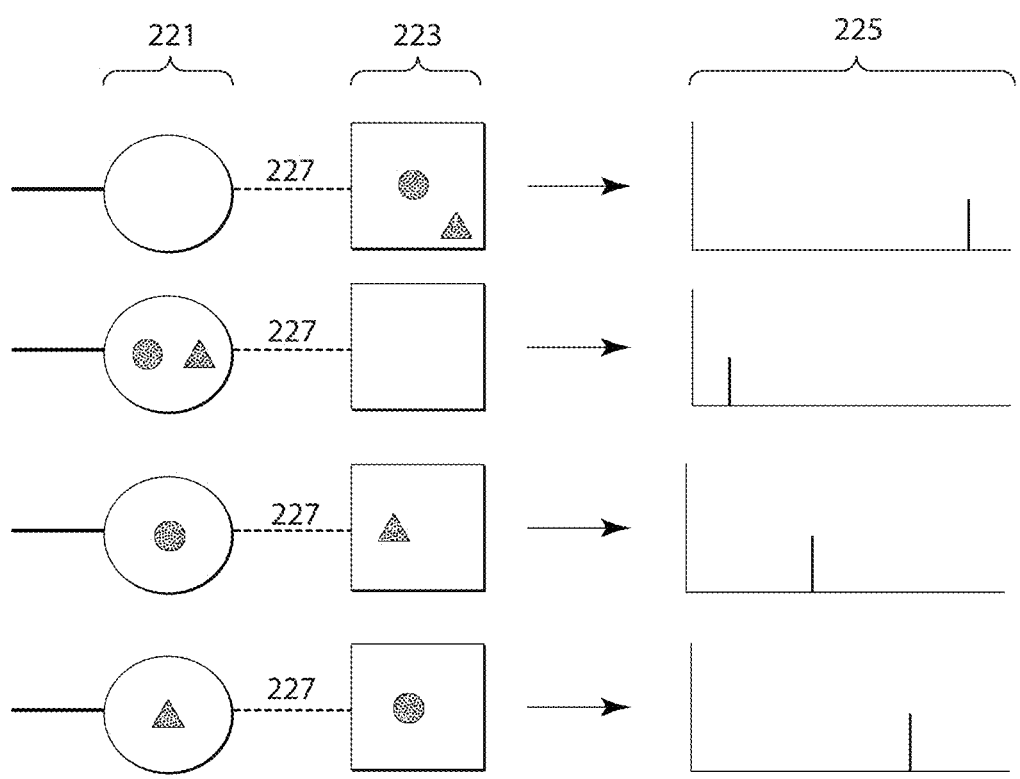
FIG. 3B is a schematic of the multiplexing capacity for a conventional mass spectrometry tag containing two different isotopes, according to one set of embodiments.

A non-limiting example of the difference in multiplexing capacity between the tags described herein and conventional tags are shown in FIGS. 3A-3B. FIG. 3A shows the mass balance 222 regions and reporter regions 224 of the distinguishable tags that can be produced using a stable heavy nitrogen isotope, indicated by the solid triangle, a stable heavy carbon isotope, indicated by the solid circle. The mass spectra 226 shows the primary reporter ion (indicated by a dashed line on the spectra) that is produced by cleavage of bond 228 and the secondary reporter ion (illustrated by the oval within the primary reporter region) and solid line on the spectra. The mass spectrometry system, described herein, was able to produce eight distinguishable tags. FIG. 3B shows the mass balance regions 221 and reporter regions 223 of the distinguishable tags that can be produce using a stable heavy nitrogen isotope (indicated by the solid triangle), a stable heavy carbon isotope (indicated by the solid circle) for a conventional system. The mass spectra 225 showing the sole reporter ion that is produced by cleavage of bond 227. The conventional mass spectrometry system, described herein, was only able to produce four distinguishable tags.

A non-limiting example of a set a mass spectrometry tags, described herein, having a relatively high multiplexing capacity is shown in Table 1. Table 1 shows a set of mass spectrometry tags formed using 4 heavy isotopes per tag with a limit of one heavy nitrogen isotope per tag as well as the resulting primary and secondary reporter ions. The exemplified set in Table 1 comprises distinguishable 16 isotopic isomers (e.g., 16-plex) having distinguishable isotopomeric reporter regions and/or isotopologous reporter regions. In some embodiments, a system may comprise two or more (e.g., four or more, six or more, all) of the mass spectrometry tags in Table 1 or isotopic isomers thereof.

TABLE 1

Set of mass spectrometry tags

| Tag | Primary | Secondary |
|---|---|---|
| 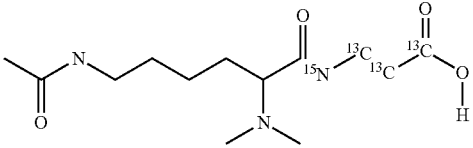<br>Exact Mass: 291.19 | 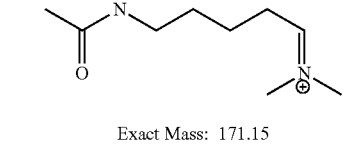<br>Exact Mass: 171.15 | 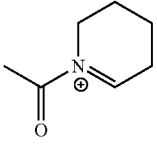<br>Exact Mass: 126.09 |
| 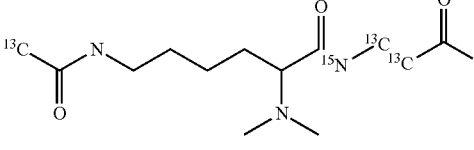<br>Exact Mass: 291.19 | 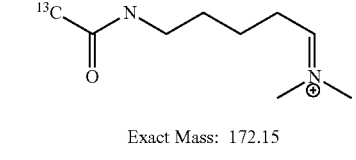<br>Exact Mass: 172.15 | 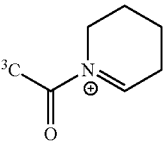<br>Exact Mass: 127.09 |
| 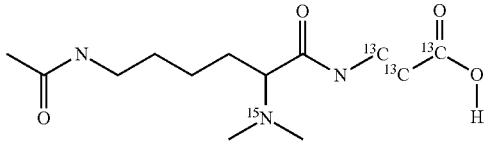<br>Exact Mass: 291.19 | 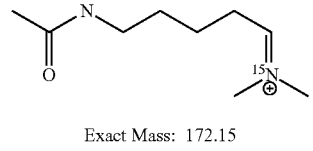<br>Exact Mass: 172.15 | 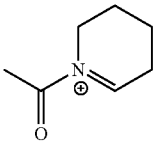<br>Exact Mass: 126.09 |
| 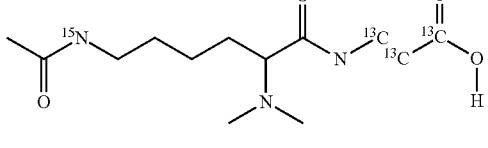<br>Exact Mass: 291.19 | 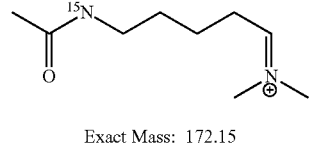<br>Exact Mass: 172.15 | 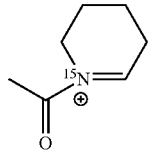<br>Exact Mass: 127.09 |
| 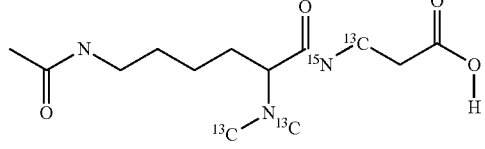<br>Exact Mass: 291.19 | 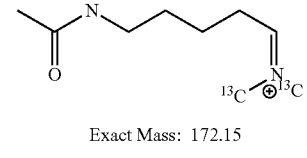<br>Exact Mass: 172.15 | 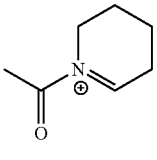<br>Exact Mass: 126.09 |

TABLE 1-continued

Set of mass spectrometry tags

| Tag | Primary | Secondary |
|---|---|---|
| 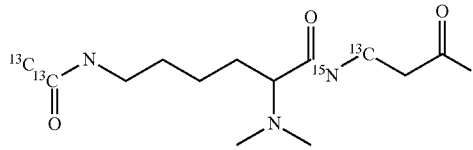<br>Exact Mass: 291.19 | 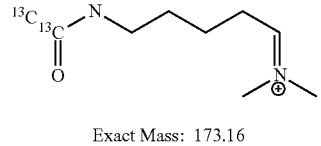<br>Exact Mass: 173.16 | 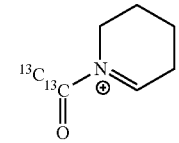<br>Exact Mass: 128.10 |
| 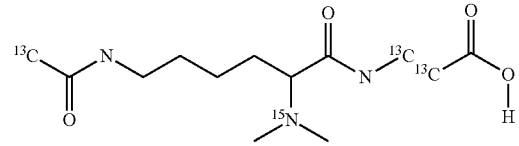<br>Exact Mass: 291.19 | 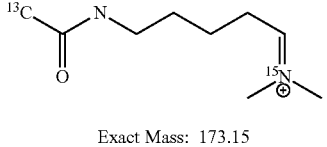<br>Exact Mass: 173.15 | 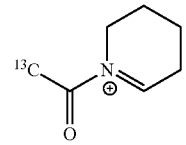<br>Exact Mass: 127.09 |
| 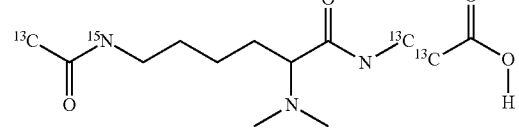<br>Exact Mass: 291.19 | 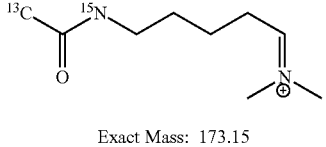<br>Exact Mass: 173.15 | 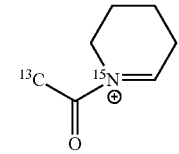<br>Exact Mass: 128.09 |
| 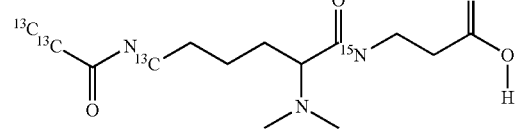<br>Exact Mass: 291.19 | 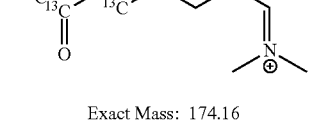<br>Exact Mass: 174.16 | 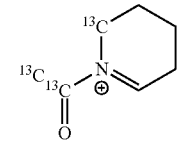<br>Exact Mass: 129.10 |
| 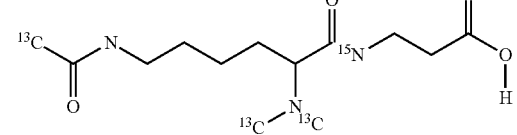<br>Exact Mass: 291.19 | 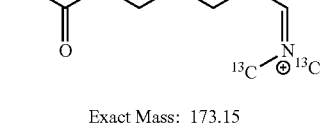<br>Exact Mass: 173.15 | 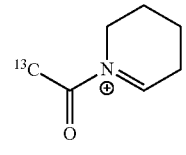<br>Exact Mass: 127.09 |
| 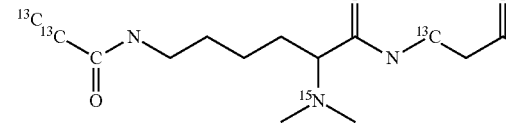<br>Exact Mass: 291.19 | 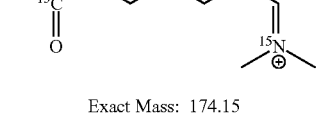<br>Exact Mass: 174.15 | 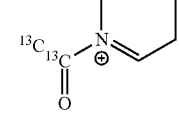<br>Exact Mass: 128.10 |
| 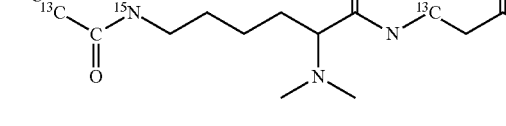<br>Exact Mass: 291.19 | 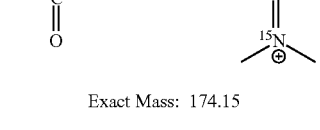<br>Exact Mass: 174.15 | 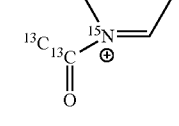<br>Exact Mass: 129.10 |

TABLE 1-continued

Set of mass spectrometry tags

| Tag | Primary | Secondary |
|---|---|---|
| 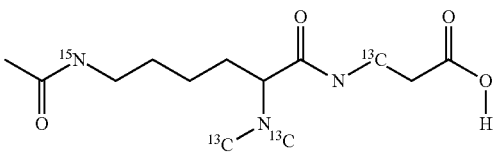 Exact Mass: 291.19 | 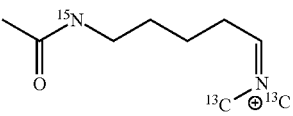 Exact Mass: 173.15 | 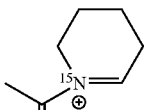 Exact Mass: 127.09 |
| 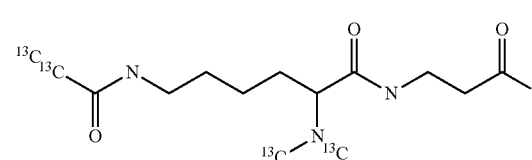 Exact Mass: 291.20 | 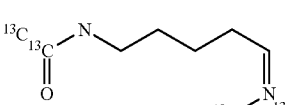 Exact Mass: 174.15 | 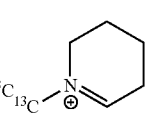 Exact Mass: 128.10 |
| 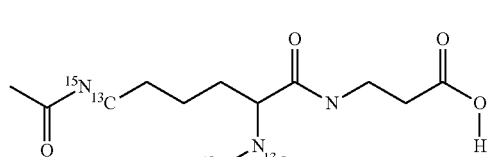 Exact Mass: 291.19 | 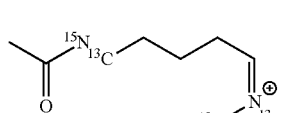 Exact Mass: 175.16 | 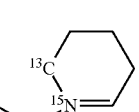 Exact Mass: 128.09 |
| 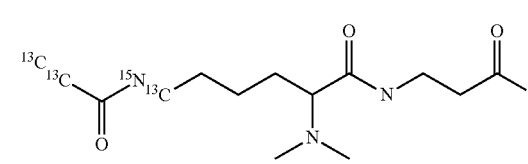 Exact Mass: 291.19 | 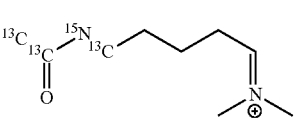 Exact Mass: 175.16 | 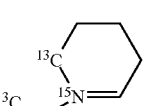 Exact Mass: 130.10 |

Another non-limiting example of a set a mass spectrometry tags, described herein, having a relatively high multiplexing capacity is shown in Table 2. Table 2 shows a set of mass spectrometry tags formed using 4 heavy isotopes per tag with a limit of one heavy nitrogen isotope per tag. The exemplified set in Table 2 comprises distinguishable 27 isotopic isomers. In some embodiments, a system may comprise two or more (e.g., four or more, eight or more, 16 or more) of the mass spectrometry tags in Table 2 or isotopic isomers thereof. In some embodiments, a subset of the distinguishable mass spectrometry tags may be used to form a detection system. For example, in some embodiments, a subset of 17 distinguishable isotopic isomers from the distinguishable isotopic isomers in Table 2 may be used to form a set of mass spectrometry tags. In certain embodiments, a plethora of detection systems may be formed using subsets of a larger set of mass spectrometry tags. For instance, millions of 17-plex detection systems may be formed using the distinguishable 27 isotopic isomers in Table 2.

TABLE 2

Set of mass spectrometry tags

1

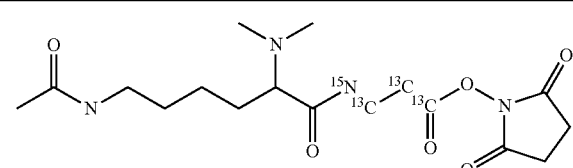

Exact Mass: 388.20798

TABLE 2-continued
Set of mass spectrometry tags
2 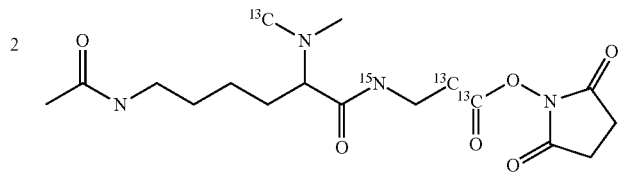
Exact Mass: 388.20798
3 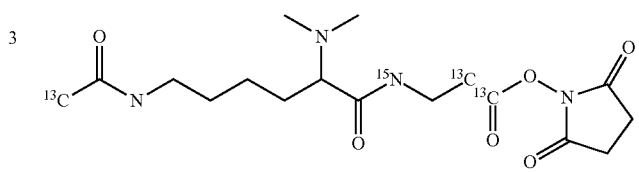
Exact Mass: 388.20798
4 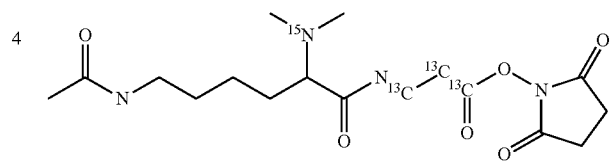
Exact Mass: 388.20798
5 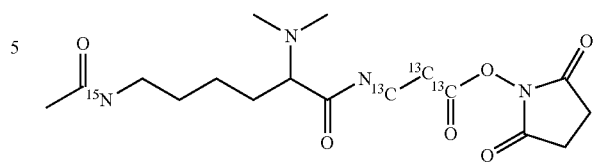
Exact Mass: 388.20798
6 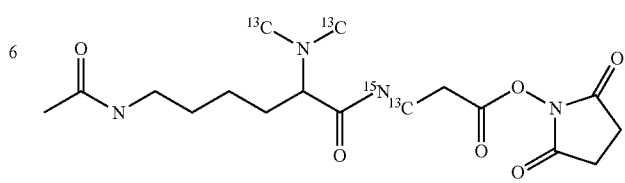
Exact Mass: 388.20798
7 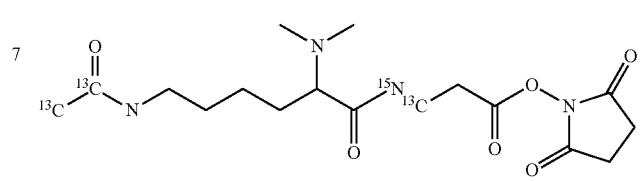
Exact Mass: 388.20798

TABLE 2-continued
Set of mass spectrometry tags
8 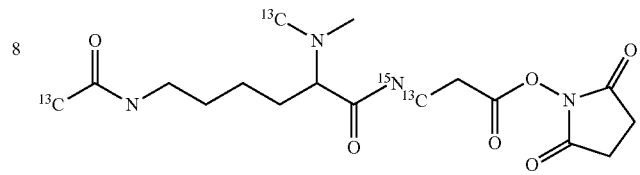
Exact Mass: 388.20798
9 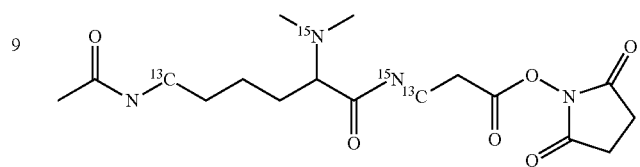
Exact Mass: 388.20166
10 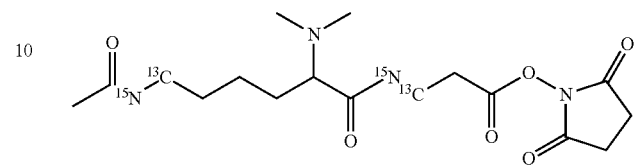
Exact Mass: 388.20166
11 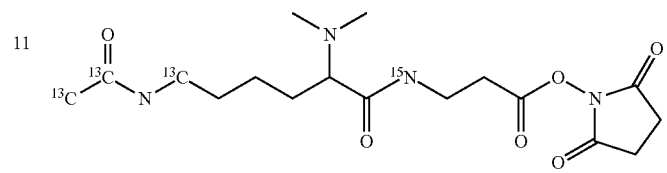
Exact Mass: 388.20798
12 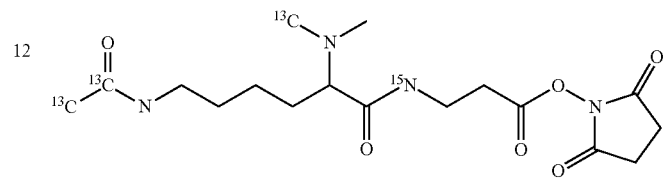
Exact Mass: 388.20798
13 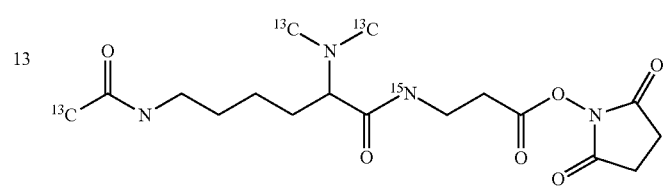
Exact Mass: 388.20798

TABLE 2-continued
Set of mass spectrometry tags
14 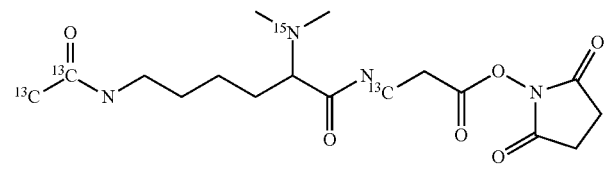
Exact Mass: 388.20798
15 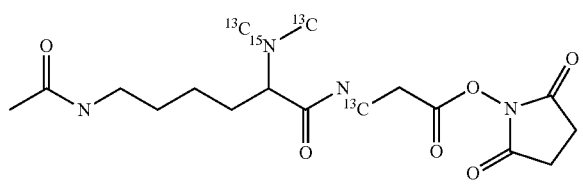
Exact Mass: 388.20798
16 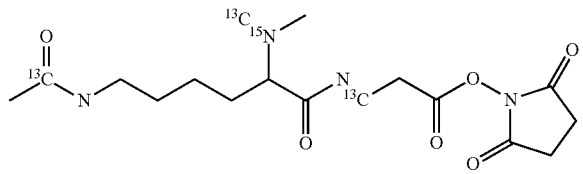
Exact Mass: 388.20798
17 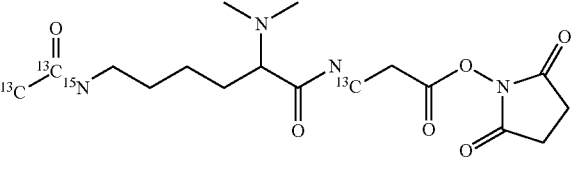
Exact Mass: 388.20798
18 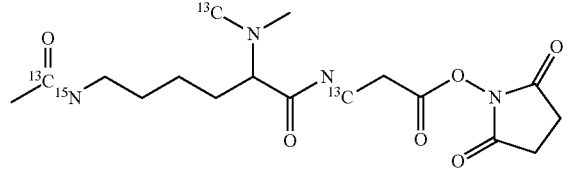
Exact Mass: 388.20798
19 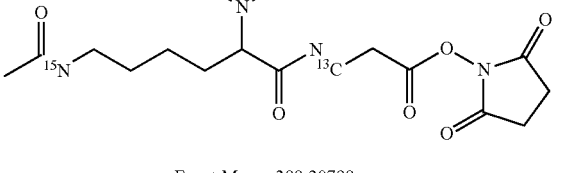
Exact Mass: 388.20798
20 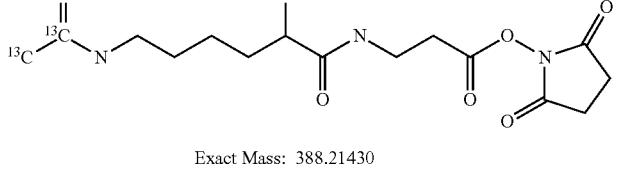
Exact Mass: 388.21430

TABLE 2-continued
Set of mass spectrometry tags
21 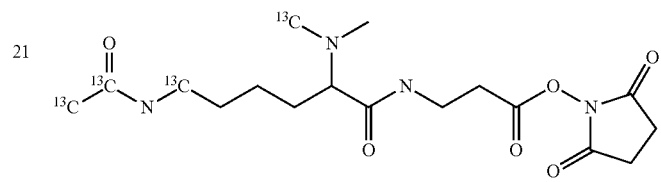
Exact Mass: 388.21430
22 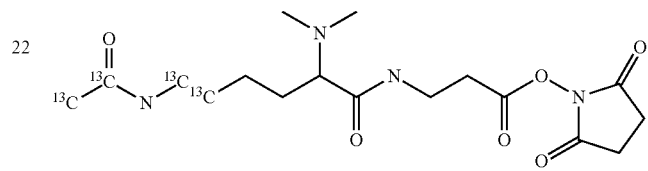
Exact Mass: 388.21430
23 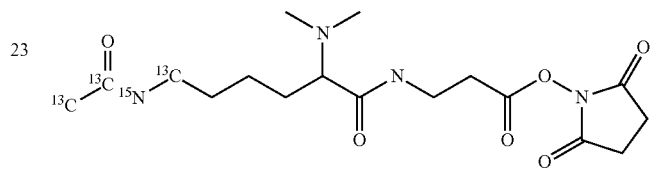
Exact Mass: 388.20798
24 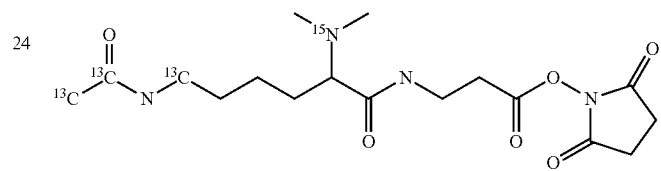
Exact Mass: 388.20798
25 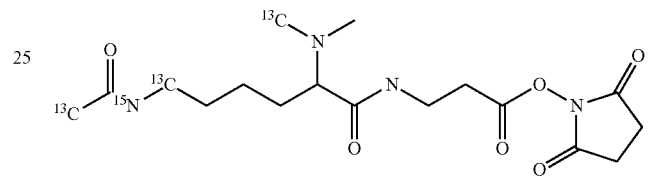
Exact Mass: 388.20798
21 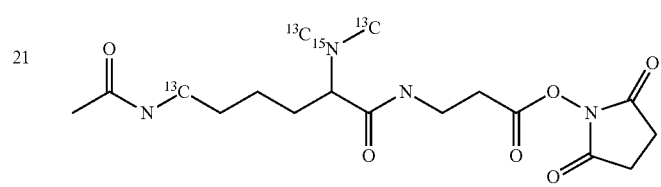
Exact Mass: 388.20798
27 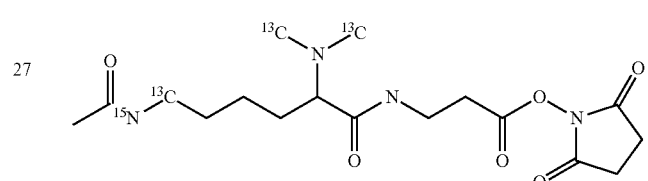
Exact Mass: 388.20798

A non-limiting example of a set a mass spectrometry tags, described herein, and the resulting primary, secondary, and tertiary reporter ions is shown in Table 3. Table 3 shows a set of mass spectrometry tags formed using 3 heavy isotopes per tag. The exemplified set in Table 3 comprises distinguishable 10 isotopic isomers (e.g., 10-plex) having distinguishable isotopomeric reporter regions and/or isotopologous reporter regions. In some embodiments, a system may comprise two or more (e.g., four or more, six or more, all) of the mass spectrometry tags in Table 3 or isotopic isomers thereof.

TABLE 3

Set of mass spectrometry tags

| Tag | Primary | Secondary | Tertiary |
|---|---|---|---|
| 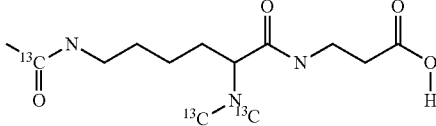<br>Exact Mass: 290.19 | 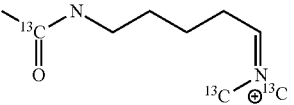<br>Exact Mass: 173.15 | 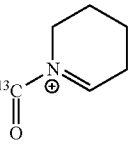<br>Exact Mass: 127.09 | <br>Exact Mass: 84.08 |
| 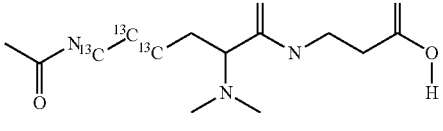<br>Exact Mass: 290.19 | 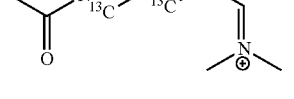<br>Exact Mass: 174.16 | 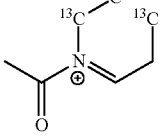<br>Exact Mass: 129.10 | <br>Exact Mass: 87.09 |
| 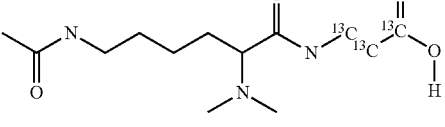<br>Exact Mass: 290.19457 | 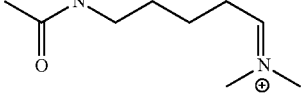<br>Exact Mass: 171.14919 | 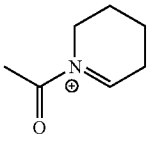<br>Exact Mass: 126.09134 | <br>Exact Mass: 84.08078 |
| 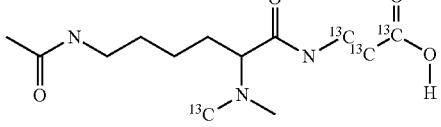<br>Exact Mass: 290.19457 | 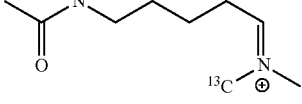<br>Exact Mass: 172.15254 | 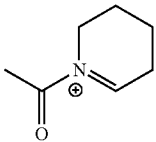<br>Exact Mass: 126.09134 | 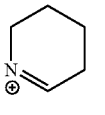<br>Exact Mass: 84.08078 |
| 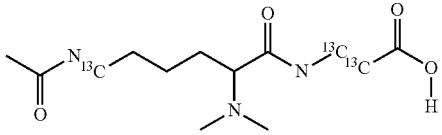<br>Exact Mass: 290.19457 | 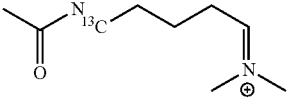<br>Exact Mass: 172.15254 | 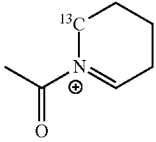<br>Exact Mass: 127.09470 | <br>Exact Mass: 85.08413 |
| 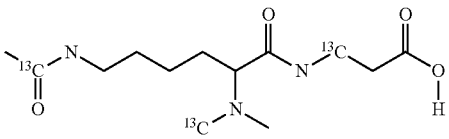<br>Exact Mass: 290.19457 | 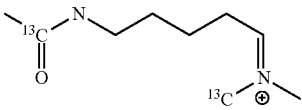<br>Exact Mass: 173.15590 | 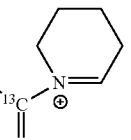<br>Exact Mass: 127.09470 | <br>Exact Mass: 84.08078 |

TABLE 3-continued

Set of mass spectrometry tags

| Tag | Primary | Secondary | Tertiary |
|---|---|---|---|
| 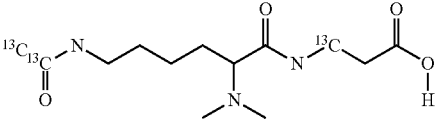 Exact Mass: 290.19457 | 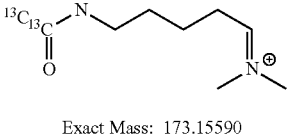 Exact Mass: 173.15590 | 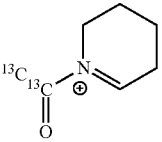 Exact Mass: 128.09805 | 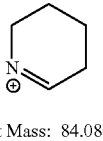 Exact Mass: 84.08078 |
| 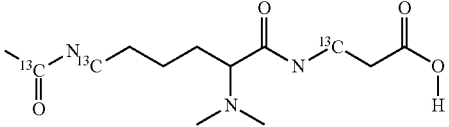 Exact Mass: 290.19457 | 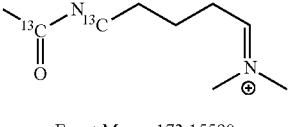 Exact Mass: 173.15590 | 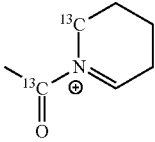 Exact Mass: 128.09805 | 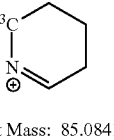 Exact Mass: 85.08413 |
| 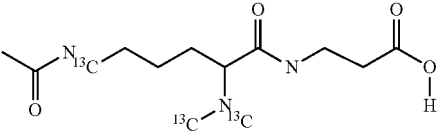 Exact Mass: 290.19457 | 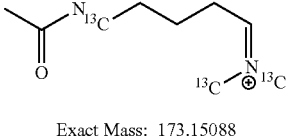 Exact Mass: 173.15088 | 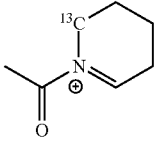 Exact Mass: 127.09470 | 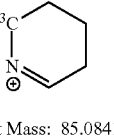 Exact Mass: 85.08413 |
| 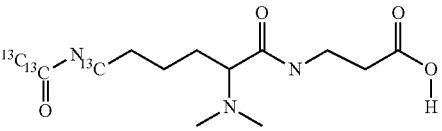 Exact Mass: 290.19457 | 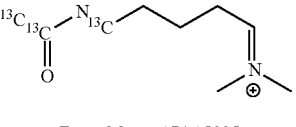 Exact Mass: 174.15925 | 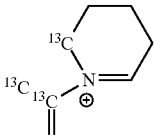 Exact Mass: 129.10140 | 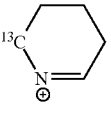 Exact Mass: 85.08413 |

A non-limiting example of a set a mass spectrometry tags, described herein, having a relatively high multiplexing capacity as well as a tertiary reporter ion series is shown in Table 4. The exemplified set in Table 4 comprises distinguishable 30 isotopic isomers (e.g., 30-plex) having distinguishable isotopomeric reporter regions and/or isotopologous reporter regions. In some embodiments, a system may comprise two or more (e.g., four or more, eight or more, 16 or more) of the mass spectrometry tags in Table 4 or isotopic isomers thereof.

TABLE 4

Set of mass spectrometry tags

| Tag | Primary | Secondary | Tertiary |
|---|---|---|---|
| 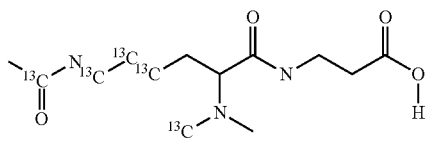 Exact Mass: 292.20 | 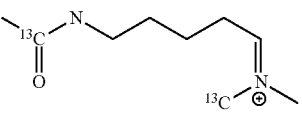 Exact Mass: 173.16 | 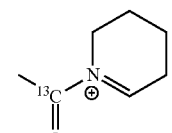 Exact Mass: 127.09 | 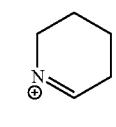 Exact Mass: 84.08 |

TABLE 4-continued

Set of mass spectrometry tags

| Tag | Primary | Secondary | Tertiary |
|---|---|---|---|
| Exact Mass: 292.19 | Exact Mass: 173.16 | Exact Mass: 128.09 | Exact Mass: 85.08 |
| Exact Mass: 292.20 | Exact Mass: 172.15 | Exact Mass: 127.09 | Exact Mass: 84.08 |
| Exact Mass: 292.19 | Exact Mass: 174.16 | Exact Mass: 129.10 | Exact Mass: 85.08 |
| Exact Mass: 292.19 | Exact Mass: 175.16 | Exact Mass: 129.10 | Exact Mass: 85.08 |
| Exact Mass: 292.19 | Exact Mass: 174.16 | Exact Mass: 128.10 | Exact Mass: 84.08 |
| Exact Mass: 292.19496 | Exact Mass: 171.14919 | Exact Mass: 126.09134 | Exact Mass: 84.08078 |
| Exact Mass: 292.19496 | Exact Mass: 172.15254 | Exact Mass: 126.09134 | Exact Mass: 84.08078 |

TABLE 4-continued

Set of mass spectrometry tags

| Tag | Primary | Secondary | Tertiary |
|---|---|---|---|
| 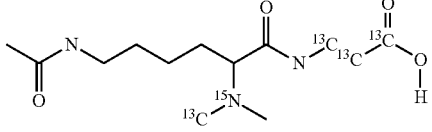 Exact Mass: 292.19496 | 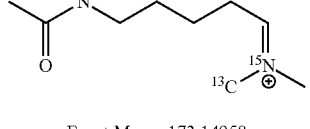 Exact Mass: 173.14958 | 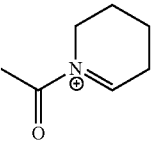 Exact Mass: 126.09134 | 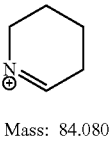 Exact Mass: 84.08078 |
| 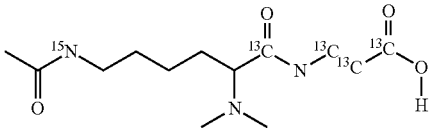 Exact Mass: 292.19496 | 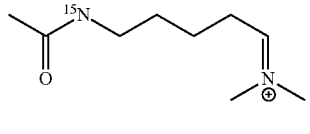 Exact Mass: 172.14622 | 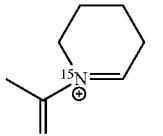 Exact Mass: 127.08838 | 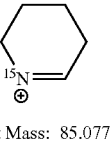 Exact Mass: 85.07781 |
| 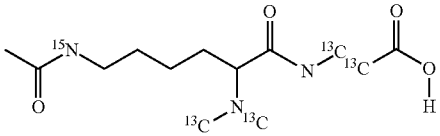 Exact Mass: 292.19496 | 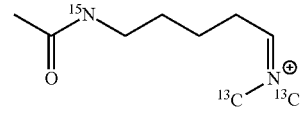 Exact Mass: 174.15293 | 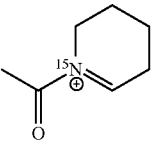 Exact Mass: 127.08838 | 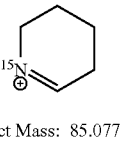 Exact Mass: 85.07781 |
| 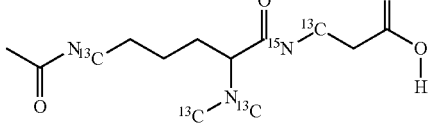 Exact Mass: 292.19496 | 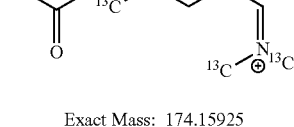 Exact Mass: 174.15925 | 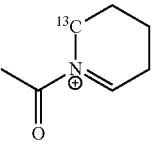 Exact Mass: 127.09470 | 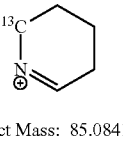 Exact Mass: 85.08413 |
| 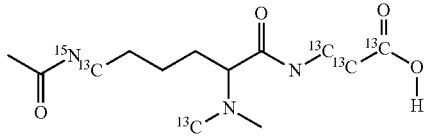 Exact Mass: 292.19496 | 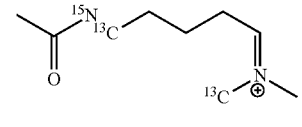 Exact Mass: 174.15923 | 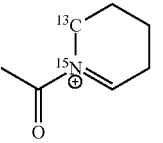 Exact Mass: 128.09173 | 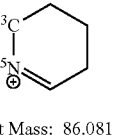 Exact Mass: 86.08117 |
| 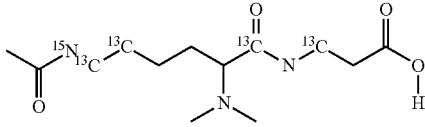 Exact Mass: 292.19496 | 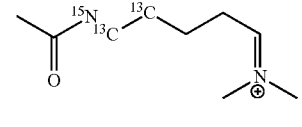 Exact Mass: 174.15923 | 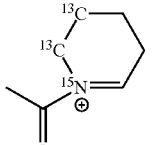 Exact Mass: 129.09509 | 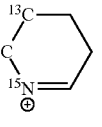 Exact Mass: 87.08452 |
| 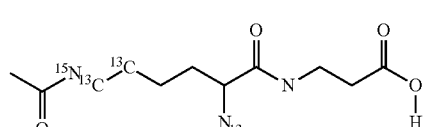 Exact Mass: 292.19496 | 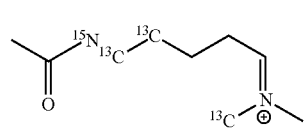 Exact Mass: 175.15629 | 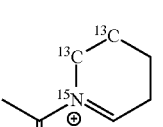 Exact Mass: 129.09509 | 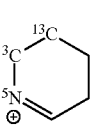 Exact Mass: 87.08452 |

TABLE 4-continued

Set of mass spectrometry tags

| Tag | Primary | Secondary | Tertiary |
|---|---|---|---|
| 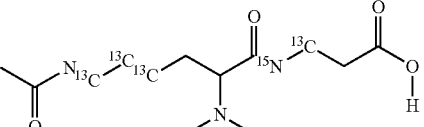 Exact Mass: 292.19496 | 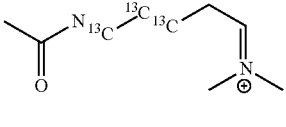 Exact Mass: 174.15925 | 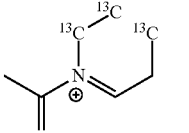 Exact Mass: 129.10140 | 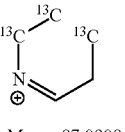 Exact Mass: 87.09084 |
| 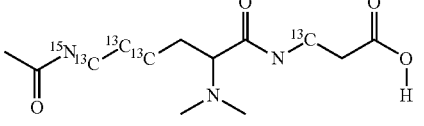 Exact Mass: 292.19496 | 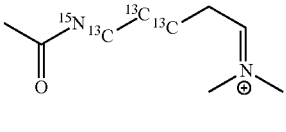 Exact Mass: 175.15629 | 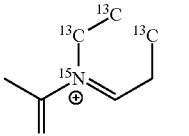 Exact Mass: 130.09844 | 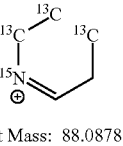 Exact Mass: 88.08788 |
| 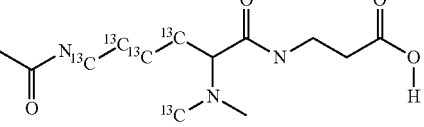 Exact Mass: 292.20128 | 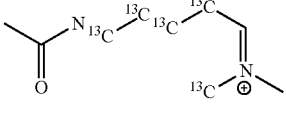 Exact Mass: 176.16596 | 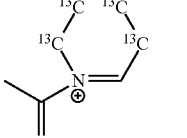 Exact Mass: 130.10476 | 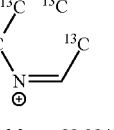 Exact Mass: 88.09420 |
| 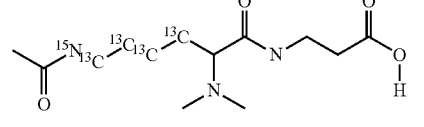 Exact Mass: 292.19496 | 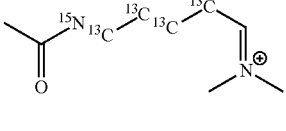 Exact Mass: 176.15964 | 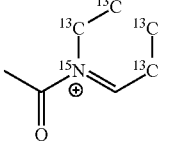 Exact Mass: 131.10179 | 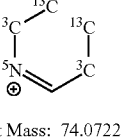 Exact Mass: 74.07223 |
| 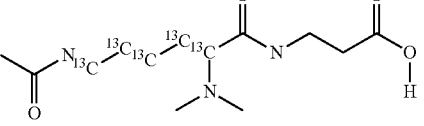 Exact Mass: 292.20128 | 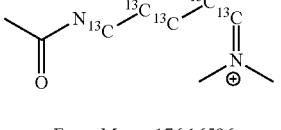 Exact Mass: 176.16596 | 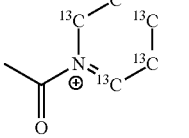 Exact Mass: 131.10866 | 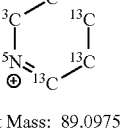 Exact Mass: 89.09755 |
| 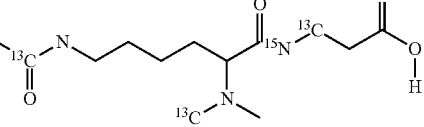 Exact Mass: 291.19161 | 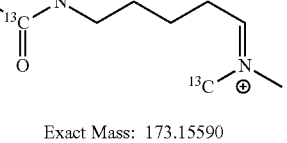 Exact Mass: 173.15590 | 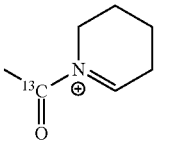 Exact Mass: 127.09470 | 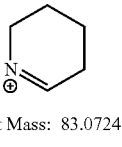 Exact Mass: 83.07240 |
| 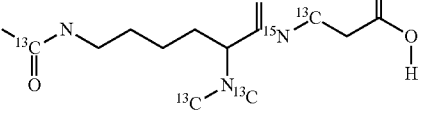 Exact Mass: 292.19496 | 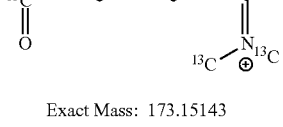 Exact Mass: 173.15143 | 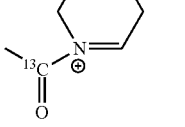 Exact Mass: 127.09470 | 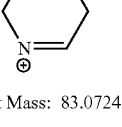 Exact Mass: 83.07240 |

TABLE 4-continued

Set of mass spectrometry tags

| Tag | Primary | Secondary | Tertiary |
|---|---|---|---|
| 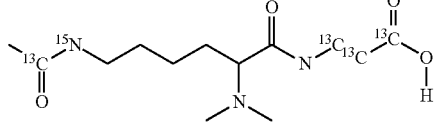<br>Exact Mass: 292.19496 | 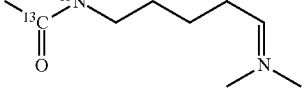<br>Exact Mass: 173.15013 | 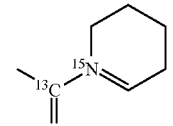<br>Exact Mass: 128.09228 | 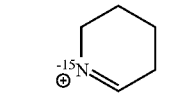<br>Exact Mass: 84.07053 |
| 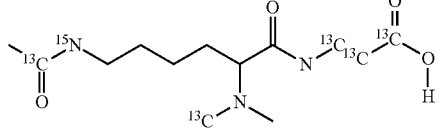<br>Exact Mass: 292.19496 | 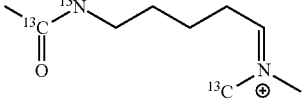<br>Exact Mass: 174.15348 | 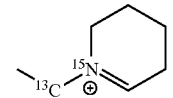<br>Exact Mass: 128.09228 | 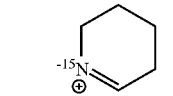<br>Exact Mass: 84.07053 |
| 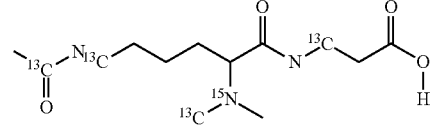<br>Exact Mass: 292.19496 | 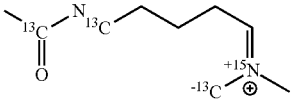<br>Exact Mass: 173.15629 | 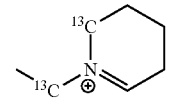<br>Exact Mass: 128.09860 | 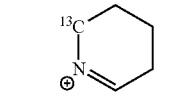<br>Exact Mass: 84.07685 |
| 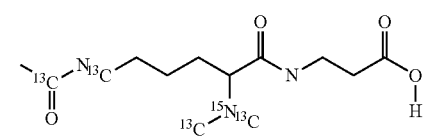<br>Exact Mass: 292.19496 | 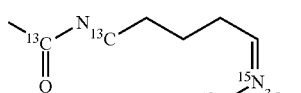<br>Exact Mass: 176.16019 | 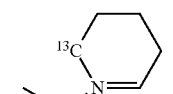<br>Exact Mass: 128.09805 | 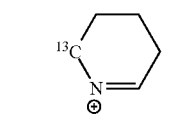<br>Exact Mass: 85.08413 |
| 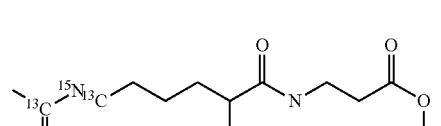<br>Exact Mass: 292.19496 | 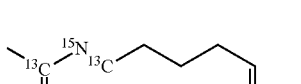<br>Exact Mass: 176.15964 | 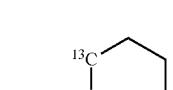<br>Exact Mass: 129.09563 | 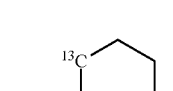<br>Exact Mass: 85.07389 |
| 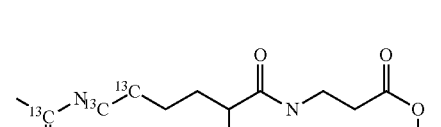<br>Exact Mass: 292.19496 | 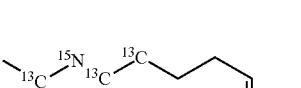<br>Exact Mass: 176.15964 | 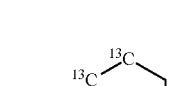<br>Exact Mass: 129.10140 | 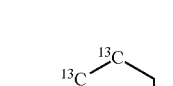<br>Exact Mass: 85.08021 |
| 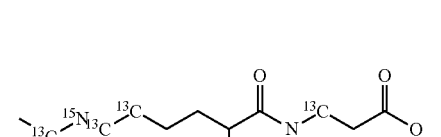<br>Exact Mass: 292.19496 | 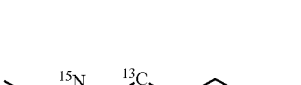<br>Exact Mass: 175.15684 | 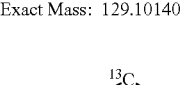<br>Exact Mass: 130.09899 | 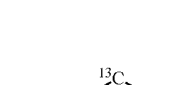<br>Exact Mass: 86.07724 |

TABLE 4-continued

Set of mass spectrometry tags

| Tag | Primary | Secondary | Tertiary |
|---|---|---|---|
| Exact Mass: 292.19496 | Exact Mass: 175.16316 | Exact Mass: 130.10476 | Exact Mass: 87.09084 |

Figure 4:
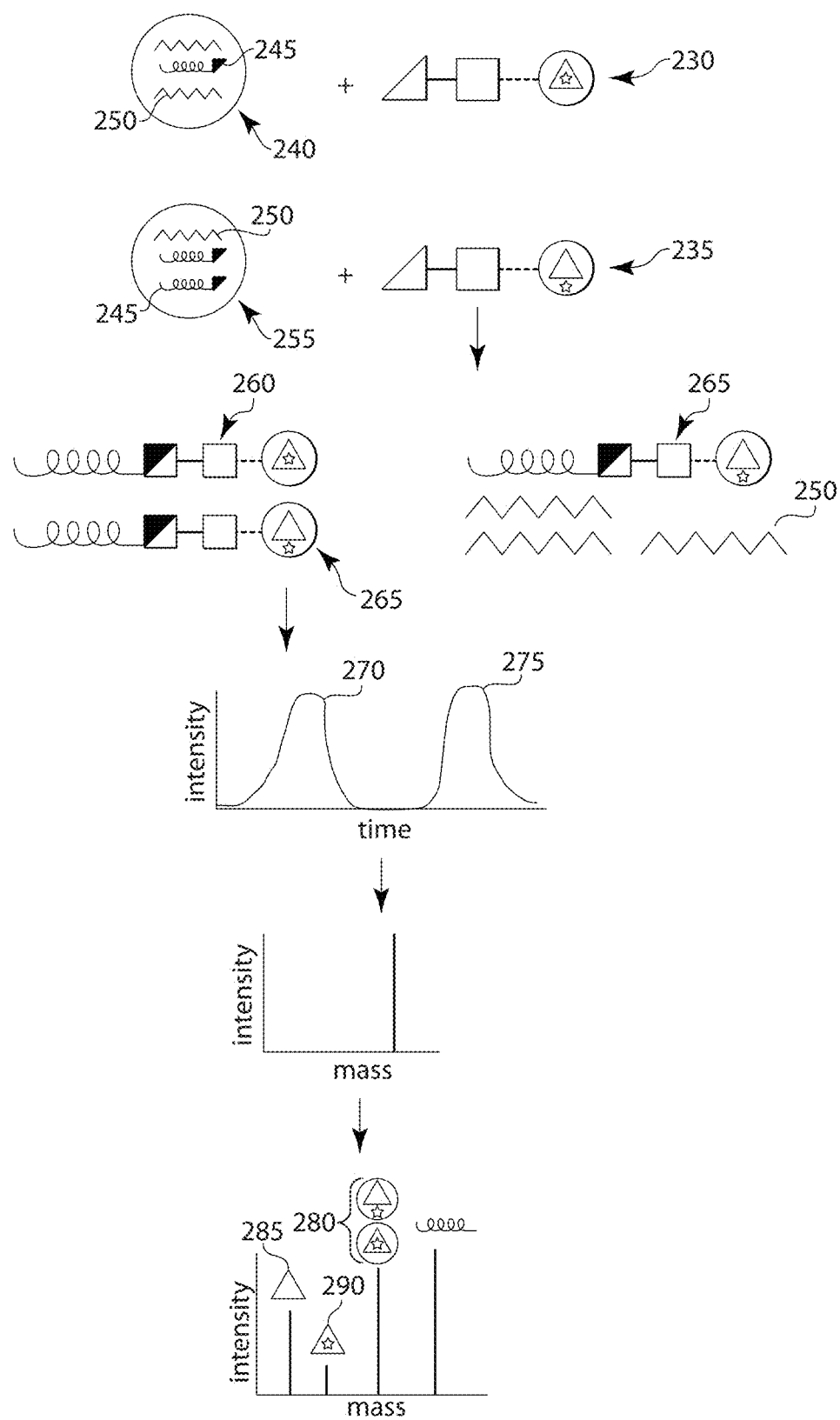
FIG. 4 is a schematic of a mass spectrometry approach for the quantitative determination of an analyte in various samples using a mass spectrometry tag, according to certain embodiments.

In general, a system comprising a set of mass spectrometry tags, as described herein, may be used for a variety of applications. In some embodiments, the labeling systems, described herein, may be used to determine an analyte using tandem mass spectrometry. For instance, a set of mass spectrometry tags may be used to determine the relative abundance of an analyte in a variety of samples that are processed in a single stream. A non-limiting example of such an application is shown in FIG. 4. FIG. 4 shows a schematic of a method of quantitatively determining an analyte using two mass spectrometry tags, described herein. Tags 230 and 235 may be isobaric and have reporting regions that are isotopic isomers. In some embodiments, tag 230 may be placed into sample 240 comprising a certain amount of analyte 245 and ion 250. Tag 235 may be placed into sample 255 comprising a certain amount of analyte 245 and ion 250. The linker regions in tags 230 and 235 may comprise a reactive group that is capable of associating with analyte 245. Tags 230 and 235 may associate with analyte 245 in their respective samples to formed labeled analyte 260 and 265, respectively. Samples 240 and 255 may be combined and subject to chromatographic separation. Labeled analyte 260 and 265 may co-migrate, such that the chromatogram includes a peak 270 for ion 250 and a peak 275 for the labeled analyte. Peak 275 may be analyzed using a tandem mass spectrometry detection system. The first mass spectrometer may not employ dissociation conditions and labeled analyte may not be distinguishable based on the mass spectrum. The second mass spectrum may utilize dissociation conditions, which cause tags 230 and 235 to fragment. The primary reporter ion 280 from tags 230 and 235 may be the same as illustrated in FIG. 4. In some such embodiments, peak(s) attributable to the primary reporter ion on the mass spectrum may be the same for tags 230 and 235 and the intensity of the peak(s) may be proportional to the total concentration of the analyte in the combined samples. In certain embodiments, the secondary reporter ions 290 produced from tag 230 and 285 produced from tag 235 appear at different locations on the mass spectrum. In some instances, the intensity of the secondary reporter ions is proportional to the relative amount of the analyte in the tag's corresponding sample.

In another aspect, methods for enhancing the accuracy of mass spectrometry measurements using the mass spectrometry tags described herein are provided. In some such embodiments, a complementary ion may be analyzed instead of the respective tag's reporter ion. The complementary ion may be a high-mass counterpart to each reporter ion that carries a mass-balancing group of the chemical tag as well as a portion or the entirety of the tether region and/or analyte. An analysis of the complementary ions may benefit from a dynamic isolation waveform because a plurality of MS2 product ions may be selected for analysis in an efficient manner. Additional details of the use of high-mass complementary ion analysis in multiplexed MS may be found in WO 2014066284, entitled "Accurate and Interference-Free Multiplexed Quantitative Proteomics Using Mass Spectrometry" and filed Oct. 22, 2013, which is herein incorporated by reference in its entirety. It has been discovered that mass spectrometry tags of Formula (I) and/or (III) perform better than conventional isobaric tags in complement ion analysis due at least in part to the increase in more signal for the complement ion. In some embodiments, the mass spectrometry tags of Formula (I) and/or (III) produce the complement ion with increased signal for a greater proportion of labelled analytes compared to conventional isobaric reagents (e.g., TMT).

In some embodiments, methods for using the tags for multiplexed MS are provided. It is known to analyze proteins, peptides or other large molecules in a multistep process. In the example of a protein analysis, in a first portion of the process, the protein may be broken into smaller pieces, such as peptides. Certain of these peptides may be selected for further processing. Because the peptides are ions—or may be ionized by known processes such as electrospray ionization (ESI), matrix-assisted laser desorption/ionization (MALDI), or any other suitable process—selection, manipulation, and analysis may be performed using an ion trap. Depending on their frequency of oscillation, ions of different mass-to-charge ratios (m/z—where m is the mass in atomic mass units and z is the number of elemental charges) may be excited by an excitation signal with sufficient energy to escape the ion trap. What remains in the trap following excitation are ions that did not have a mass-to-charge ratio corresponding to the excitation signal. To isolate ions with a particular mass-to-charge ratio, the ion trap may be excited with a signal that includes a range of frequencies except the frequency that excites the ions of interest. Such an excitation signal, also referred to as an isolation waveform, is said to have a frequency "notch" corresponding to the target ion that is to be isolated.

The selected ions remaining in the trap may be again broken into smaller pieces, generating smaller ions. These ions may then be further processed. Processing may entail selecting and further breaking up the ions. The number of stages at which ions are selected and then broken down again may define the order of the mass spectrometry analysis, such as MS2 (also referred to as MS/MS) or MS3. Regardless of the order, at the end stage, the mass-to-charge distribution of the ions may be measured, providing data from which properties of the compound under analysis may be inferred. The ions prior to a fragmentation are sometimes called "precursor" ions and the ions resulting from a fragmentation are sometimes called "product ions." The massto-charge distribution may be acquired for any group of product ions. Moreover, all or a subset of product ions from one stage of MS may be used as precursor for a subsequent stage of MS.

The above multistep process may be time consuming. It is known to increase the throughput of a mass spectrometry facility by analyzing multiple scans at the same time, which is sometimes referred to as "multiplexing" the scans. In traditional multiplexed MS analysis, each precursor ion being isolated is typically isolated one at a time in a serial manner, one after the other. An isolation waveform is applied with a single isolation notch to isolate a particular precursor ion. Then, the resulting precursor ion population is moved to an intermediate storage vessel. This process is repeated serially with single notch waveforms until the intermediate vessel contained the desired number of precursor ions. Following accumulation of the plurality of precursor ions, the entire ensemble is fragmented and the resulting fragment ions are analyzed. In another implementation, each precursor ion is fragmented individually and then the resulting fragment ions are moved to the intermediate ion storage vessel.

In another implementation, "multiplexing" can include the use of specially designed tags, as described herein, which provided the ability to perform multiplexed quantitation of a plurality of samples simultaneously. Performing multiplexed quantitation allows the relative quantities of particular proteins or peptides between samples to be determined. For example, multiplexed quantitation may be used to identify differences between two tissue samples, which may comprise thousands of unique proteins.

The tags are included in reagents used to treat peptides as part of sample processing. A different tag may be used for each sample. The intensity of the reporter ion signal for a given tag is indicative of the amount of the tagged protein or peptide within the sample. Accordingly, multiple samples may be tagged with different tags and simultaneously analyzed to directly compare the difference in the quantity of particular proteins or peptides in each sample.

It has been recognized and appreciated that when analyzing complex mixtures, peptides selected for fragmentation are typically contaminated by co-eluting ions. Reporter ions may therefore originate from both target and interfering ions, which cause a distortion of the quantification. In this case, determining the quantity of the tagged target peptide is difficult due to the reporter ions of the target peptides being indistinguishable from the reporter ions of interfering ions. Accordingly, any interfering ion that was co-isolated with the target peptide destroyed the ability to accurately determine the relative quantity of the target peptide in the sample.

It has been recognized and appreciated that, though the isobaric chemical tags may be designed to quantify the relative abundance of molecules in a complex sample using the low-mass reporter ions, the problem of co-isolated peptides may be remedied by measuring the intensity of each high-mass complementary ion associated with each labeled peptide, instead of quantifying the amount of each differentially labeled peptide based on reporter ion intensities. The fragmentation mechanism for labeled peptides is such that, concurrent with the formation of the low-mass reporter ions, high-mass complementary ions are formed as well. The high-mass complementary ions carry most of the mass-balancing group of the tag. Accordingly, information regarding the relative abundances of the labeled samples may be obtained by measuring the relative abundances of the complementary ions.

It has been recognized and appreciated that, in contrast to the use of low m/z reporter ions, the m/z values of these complementary ions are precursor specific. The risk that a complementary ion of a target molecule will have a spectral envelope at exactly the same location in the MS2 spectrum as a complementary ion for an interfering molecule is very low. Accordingly, interfering peptides have a much smaller effect on the measurement of the tag complement ion of interest. Furthermore, should other peptides interfere with the tag complement ion cluster, it is unlikely that the interfering peptides would result in an ion cluster which could be generated only by the peptide of interest. By comparing the observed ion-clusters with theoretical ion-clusters, peptides with inaccurate quantitation can be filtered out and inaccurate quantification further reduced. Using complementary ions to quantify relative abundances may be implemented on a wide range of mass spectrometers—e.g. quadrupole time-of-flight (Q-TOF), quadrupole Orbitrap instruments (QExactive), hybrid quadrupole ion trap Orbitrap mass spectrometers, and Fourier-transform ion cyclotron resonance analyzers (FT-ICRs). This complementary ion technique not only provides higher accuracy in the quantification of labeled molecules, but also maintains the parallelization of the multiplexed tags; hence, it has the potential to multiply the number of distinct peptides that can be quantified in a given time frame.

It has been recognized and appreciated that, unlike some techniques that require analyzing an $MS^3$ spectrum, or that utilize a proton transfer reaction, embodiments of the present application do not require any additional gas-phase purification steps and may therefore result in higher sensitivity and faster data acquisition. It has been recognized and appreciated that the high mass accuracy and resolution mass-spectrometers allow the quantification of peptides using tag complement ions. As an alternative to using the low m/z reporter ions in the $MS^2$ spectrum, embodiments quantify differences between the various samples based on tag complement ions. The complementary ions carry the equivalent quantitative information about the relative levels of the differentially labeled peptides as the low m/z reporter ions, but are minimally affected by interfering peptide ions. While the low-mass m/z reporter ions are isomeric and therefore undistinguishable regarding their origin from target or contaminating ions, the resulting tag complement ions from target and contaminating ions are expected to show differences in their m/z values, which makes them distinguishable using modern mass spectrometry.

It has also been recognized and appreciated that, though the observed quantities of the complementary ions do not directly give relative abundance information, this information may be extracted from the data based on a data analysis that uses details about the tags and the labeled molecule.

Analysis of complementary ions may be performed as described in WO 2014066284, entitled "Accurate and Interference-Free Multiplexed Quantitative Proteomics Using Mass Spectrometry" and filed Oct. 22, 2013, except the tags described herein are used.

In some embodiments, the mass balance region and/or at least a portion of complement ion 80 may be used as the complement ion. In some such embodiments, the mass balance region may be configured to fragment in a mass spectrometer under dissociation conditions to produce multiple complement ions. The mass balance region may fragment via the same mechanisms as described above with respect to the reporter region. In certain embodiments, the mass balance region of the tag may be configured to produce at least two complement ions (e.g., a primary complement ion, a secondary complement ion) via fragmentation. In certain embodiments, the mass balance region may be configured to fragment and the reporter region may be designed to fragment as described above. In other embodiments, only one region (e.g., mass balance region, reporter region) is configured to fragment to produce distinguishable ions.

In some embodiments, the dissociation energy of the bonds within the tag may be configured such that the fragments produced under dissociation conditions may comprise at least two reporter ions (e.g., primary reporter ions and secondary reporter ions) and/or at least one complement ions (e.g., at least two complement ions), as described in more detail below. For instance, cleavage of the Q-R' bond may produce a primary reporter ion (e.g., primary reporter ion) and at least a portion of the primary reporter ions may further react and/or fragment under the conditions in the mass spectrometer to produce a secondary reporter ion and, optionally, a tertiary reporter ion. In another example, cleavage of the L-Q bond may produce a primary complement ion (e.g., primary complement ion) and at least a portion of the primary complement ions may further react and/or fragment under the conditions in the mass spectrometer to produce a secondary complement ion and, optionally, a tertiary complement ion.

In one example, the mass balance region may fragment to produce fragments comprising at least two complement ions. In some embodiments, the fragments may primarily be formed via cleavage of susceptible bonds, as described above with respect to the reporter region. In some such embodiments, a bond (e.g., bond 30) may be broken thereby releasing the mass balance region to form a free mass balance region. At least a portion of the mass balance region may fragment to from ions. In some embodiments, the mass balance region may serve as a primary complement ion and the other ions may serve as additional complement ions. In certain embodiments, the mass balance region or one of the other ions may not be a complement ion.

In some embodiments, the fragments may be formed via cleavage of susceptible bonds and one or more chemical reaction of the mass balance region, as described above, e.g., with respect to the reporter region. In some such embodiments, a bond (e.g., bond 30) is cleaved to form a free mass balance region. At least some of the free mass balance region may undergo one or more chemical reaction to form ions. In some instances, a free mass balance region may undergo one or more chemical reaction that comprises an elimination step, which reduces its molecular weight and produces a secondary ion. In such cases, a tertiary ion may be the eliminated portion of the free mass balance region. In some embodiments, the mass balance region may serve as a primary complement ion and the other ions may serve as additional complement ions. In certain embodiments, the mass balance region 25 or one of the other ions may not be a complement ion.

As used herein "dissociation conditions" refer to conditions that induce fragmentation of a molecule. Dissociation conditions may be produced by using collision induced dissociation (CID), proton transfer reaction (PTR), infrared multi-photon dissociation (IRMPD), ultraviolet photon dissociation (UVPD), electron transfer dissociation (ETD), electron capture dissociation (ECD), high energy beam type dissociation (HCD), surface induced dissociation (SID), and/or pulsed-q dissociation (PQD). In some embodiments, the energy produced during dissociation conditions that is used to fragment a molecule is between about 100 eV and about 10 keV, about 500 eV and about 10 keV, about 1 keV and about 10 keV, about 2 keV and about 10 keV, or about 3 keV and about 10 keV. Embodiments are not limited to any particular process of fragmentation.

In another aspect, deconvolution methods are provided. In some embodiments, isotopic envelope contributions in the mass spectrometry data from each tag to RI intensities may be corrected via deconvolution. To remove interferences to the measurement from reagent isotopic envelopes in cases where more than one reagent contributes to the signal of one or more reporter ion, an estimation of the contributions of each reagent to each reporter ion may be deconvoluted using the methods described herein without considering isotopic envelope contributions to the reporter ion signals. This estimation may be used to calculate an approximate contribution of the isotopic envelope impurities of each reagent to the reporter ion signal, which may then be used to refine the estimated contribution of each reagent to the reporter ion intensities. The refined contributions are used to estimate a refined contribution of the isotopic envelopes of each reagent, which may then be used to calculate a further updated deconvolution of the contributions of each reagent to their respective reporter ion intensities. This cycle may be repeated until the refined calculation is not significantly different than the refined calculation from the previous iteration, or until a maximum number of iterations are reached. As a next step (e.g., final), the refined contributions of each reagent to their respective reporter ion intensities is normalized to the fraction of each reagent's most abundant isotopic peak within its respective isotopic envelope.

As used herein, a "stable heavy isotope" has its ordinary meaning in the art and may refer to non-radioactive elemental variant that contains one or more additional neutrons than the predominant form found in nature.

In general, an analyte may be any molecule of diagnostic value. For instance, in some embodiments, the analyte may be a nucleic acid, a biomarker, a gene, a protein, a peptide, supramolecular structure, a small molecule (e.g., therapeutics, toxin, metal, metabolite, cofactor, metal containing compound, ligand) macromolecule, receptor, biological cell, biological cell cluster, single-cell organism, or a multicellular organism.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer, or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of*

*Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$— or $^{14}C$-enriched carbon are within the scope of the disclosure. Such compounds are useful, for example, as analytical tools or probes in biological assays.

The term "reactive group," as used herein, refers to a group or moiety which is capable of being chemically modified (e.g., via chemical reaction with a compound comprising a functional group). In some embodiments, the functionalizable group is a group or moiety which is capable of being chemically modified with a functional group via formation of a bond (e.g., covalent bond, non-covalent bond, etc.) or interaction (e.g., chemical or biological interaction) between the functionalizable group and the functional group. Functionalizable groups will be selected readily, by those of ordinary skill in the art, based upon the description provided herein and knowledge in the art.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, nitrido, imino, thionitrido, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6, or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —(CH$_2$)$_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

In certain other embodiments, the alkyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl groups employed in the invention contain 1-6 aliphatic carbon atoms. In yet other embodiments, the alkyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, nitrido, imino, thionitrido, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

In some embodiments, the aryl group is a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepanyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. In certain embodiments, the aryl group is an unsubstituted $C_{6-14}$ aryl. In certain embodiments, the aryl group is a substituted $C_{6-14}$ aryl. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, and —C(=O)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen.

As used herein, the term, "amino" or "amine" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "halo" or "halogen" refers to fluorine (fluoro, —F), chlorine (chloro, —Cl), bromine (bromo, —Br), or iodine (iodo, —I).

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("C$_{1-8}$ haloalkyl"). In some embodiments, the haloalkyl moiety has 1 to 6 carbon atoms ("C$_{1-6}$ haloalkyl"). In some embodiments, the haloalkyl moiety has 1 to 4 carbon atoms ("C$_{1-4}$ haloalkyl"). In some embodiments, the haloalkyl moiety has 1 to 3 carbon atoms ("C$_{1-3}$ haloalkyl"). In some embodiments, the haloalkyl moiety has 1 to 2 carbon atoms ("C$_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —CF$_3$, —CF$_2$CF$_3$, —CF$_2$CF$_2$CF$_3$, —CCl$_3$, —CFCl$_2$, —CF$_2$Cl, and the like.

As used herein, the term "oxo" refers to the group =O, and the term "thiooxo" refers to the group =S.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, aryl, aryloxy, perhaloalkoxy, aralkoxy, heteroaryl, heteroaryloxy, heteroarylalkyl, heteroaralkoxy, azido, amino, halide, alkylthio, nitrido, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

Example 1

Figure 5:
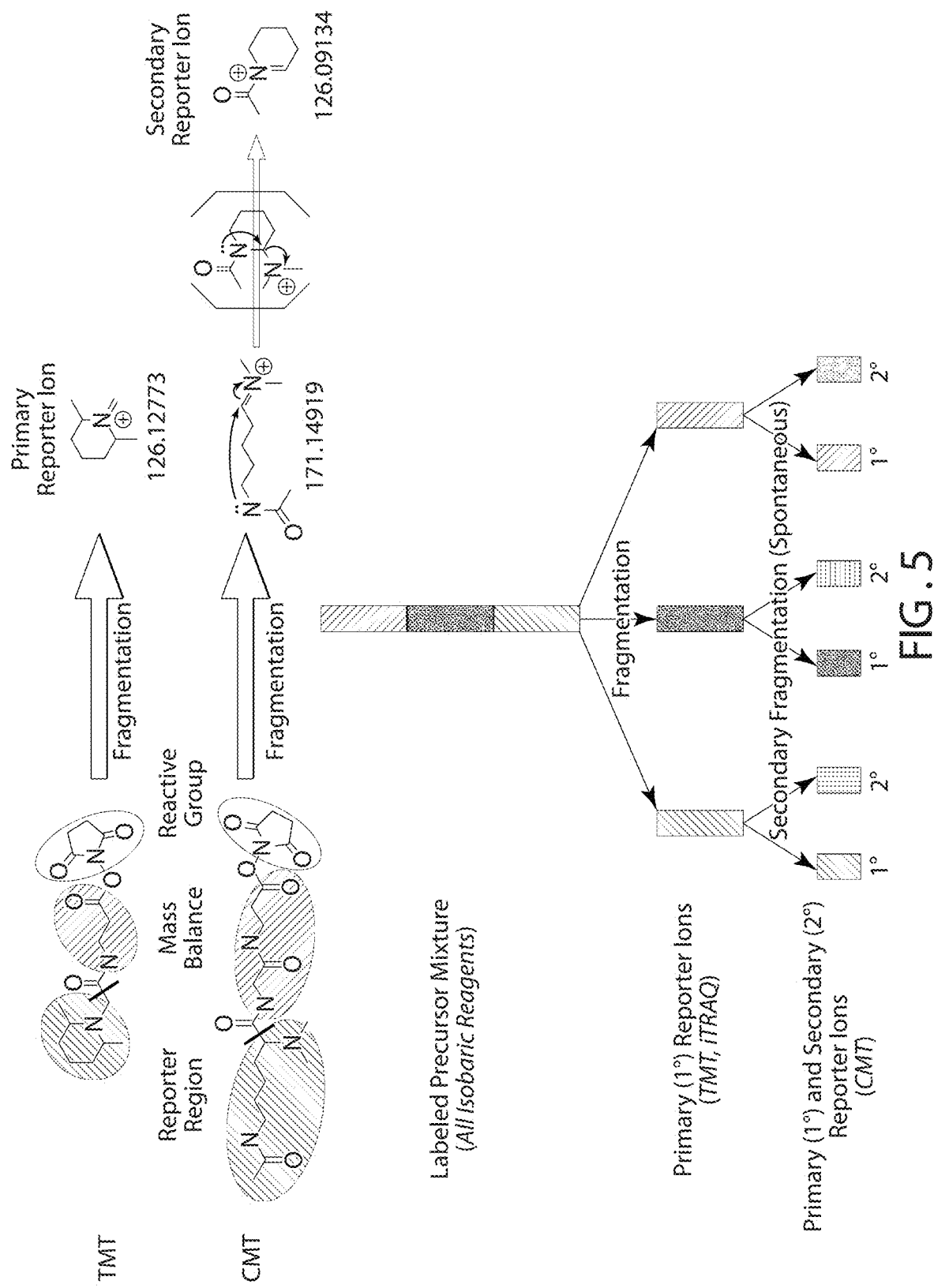
FIG. 5 is a schematic of the fragmentation of a conventional mass spectrometry tag and a mass spectrometry tag, described herein, according to certain embodiments.
Figure 6A:
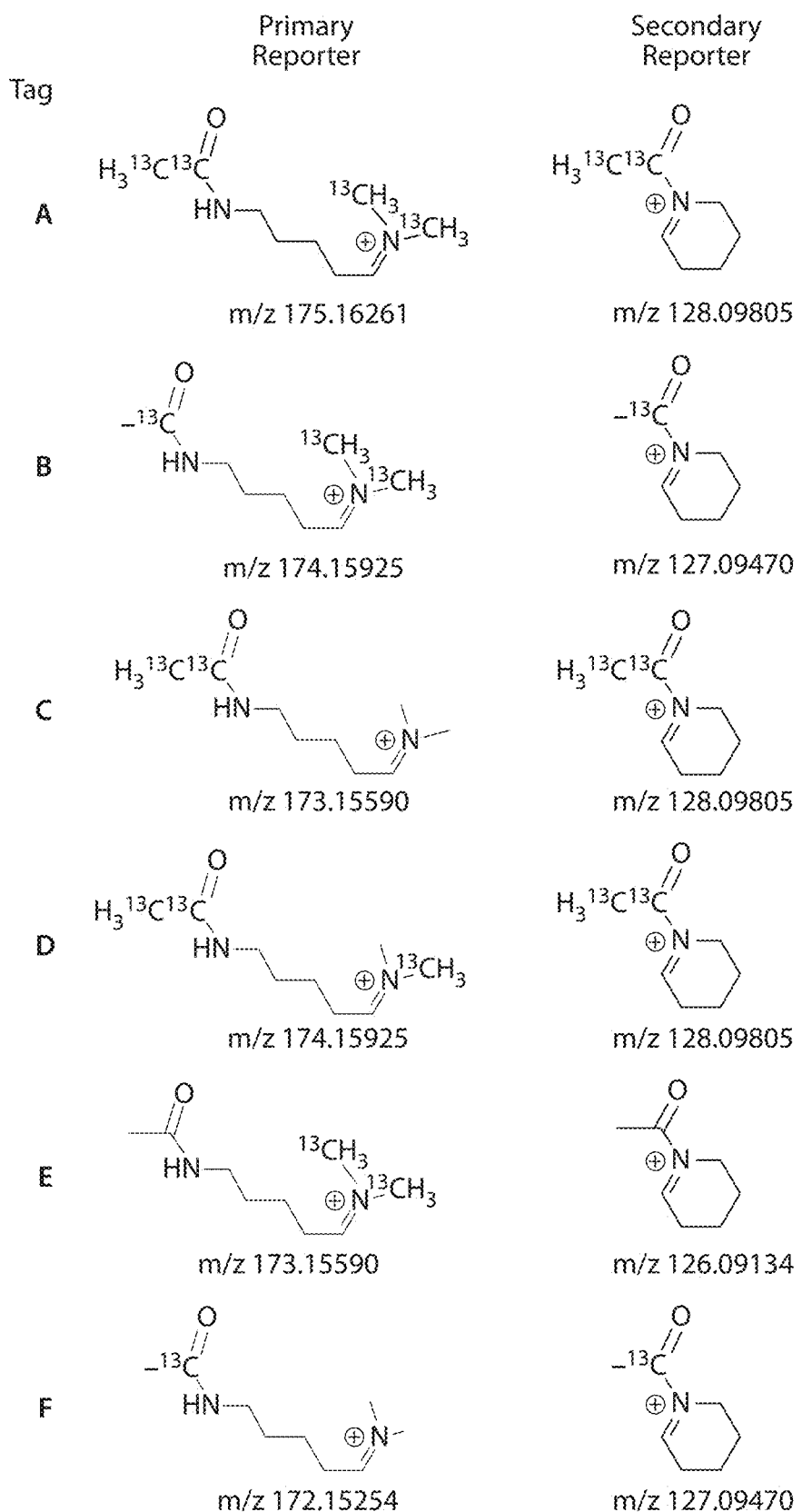
FIG. 6A is a schematic of primary and secondary reporter ions, according to one set of embodiments.

This example describes a novel isobaric labeling architecture called Combinatorial isobaric Mass Tags (CMTs) that allows a unique method for increasing the multiplexing density and capacity of isobaric reagents as shown in FIG. 5. This new tag structure uniquely undergoes dual fragmentation to release two sets of reporter ions that can both be used to obtain quantitative information. The mass shift of each reporter fragment is dependent on both the number of isotopes, and their placement, within the reporter region of the tag molecule (FIG. 6A). This dual dependence on both the number and position of isotopes within the reporter region of the molecule increases the number of unique isobaric labels that can be generated for a given number of isotopes present in the isobaric tag (FIG. 6A-E). The resulting reagents have the potential for several fold improvement in multiplexing capacity over current methods All LC-MS data were searched using the SEQUEST algorithm on a software platform developed in-house. Peptide spectral matches (PSM) were filtered to a false discovery rate (FDR) of 1% using linear discriminant analysis2. The filtered peptide list was subsequently collapsed to a final protein-level FDR of 2%. The principles of parsimony were used to guide protein assembly. Unless otherwise specified, for peptide and protein quantification, all spectra were discarded which did not meet a summed reporter ion intensity threshold of 200 (TMT) or 233 (CMT), and for which at least 80% of the signal in the MS2 isolation window did not derive from the precursor of interest. For mouse experiments, quantitative data was normalized such that the sum signal/noise across all proteins was equal for each isobaric tag. For Hierarchical clustering and principle component analysis, reporter ion intensities were further normalized within proteins such that the total sum signal/noise per protein was equal to 100. This enabled direct comparison between CMT and TMT datasets. Hierarchical clustering (Ward method) and principle component analysis were performed using the statistical analysis software JMP 11 Pro.

Figures 6B, 6C:
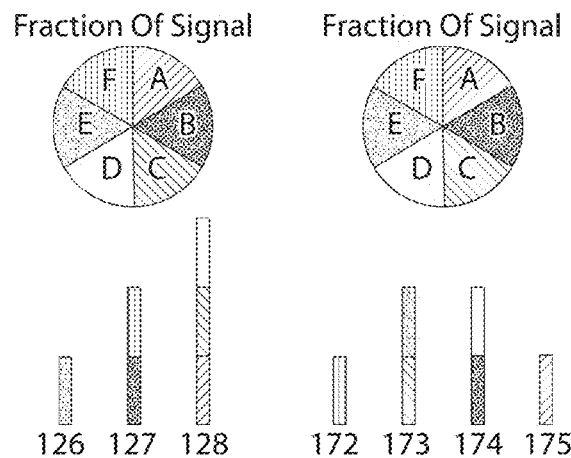
FIG. 6B is a schematic of the expected reporter ion intensities of a sample mixed with equal amounts of different tags, according to certain embodiments.
FIG. 6C shows exemplary linear equations used to determine the fraction of the reporter ion intensity originating from each mass spectrometry tag, according to one set of embodiments.

All reporter ion signal deconvolution was achieved algebraically through application of the system of linear equations presented in FIG. 6C. Isotopic envelopes for the reporter ions generated by each CMT tag were experimentally determined by analyzing samples labeled individually with each tag and extracting reporter ion intensities. Isotopic envelopes were defined as the median intensities of all reporter ion intensities observed within a 2 Da range on either side of the predominant primary and secondary reporter ions for each tag. A small c++ command line application deconvolutes each spectrum where the fractional contribution of each tag is calculated from the peak heights of the reporter ions, and the tag values are scaled with the total peak intensity to produce the intensity of each tag. The tag intensities are adjusted for isotopoc impurities with a three-step iterative method: First the tag intensities are calculated, then the fraction of spillover in the reporter ions is estimated from the tags using user-provided values for isotopic impurities, and finally the original peak heights are adjusted by this amount. This process is repeated until the tag intensities do not change or a maximum number of iterations is reached. Finally, converged deconvoluted RI intensities were normalized with respect to the known fraction of the monoisotopic peak for each tag. Signal to noise values use the noise extracted from the RAW file from the most intense peak produced by the tag.

The initial motivation behind developing in-house isobaric reagents originated from a desire for having relatively easy and fast access to customizable tags for specialized workflows. In accordance with this, the purpose was to leverage the wide availability of amino acid isotopomers and the multitude of established methods for solid phase synthesis and modification of peptide oligomers. It was reasoned that a small number of amino acid building blocks, combined with derivatization by relatively inexpensive isotopologues of acetic acid and formaldehyde would enable the rapid synthesis of a set of isobaric reagents in a relatively simple and potentially automated procedure. Pre-loaded Fmoc-bAla Wang resin was coupled first to Fmoc-glycine, followed by one of two orthogonally protected versions of lysine, and subsequent lysine epsilon amine acylation using standard Fmoc/HATU deprotection and coupling protocols on an automated peptide synthesizer. Depending on methylation state of the final product, resins were either cleaved with TFA, or mono-methylated prior to cleavage from the resin. Cleaved compounds were reductively methylated, and reacted with N,N'-Disuccinimidyl carbonate to obtain the NHS activated esters. Yields of 77% (260 µmol scale) and 87% (225 µmol scale) of CMT free acid for the homo- and hetero-dimethylation synthetic routes based on Fmoc-β Ala resin loading using this protocol were achieved.

Figures 6D, 6E:
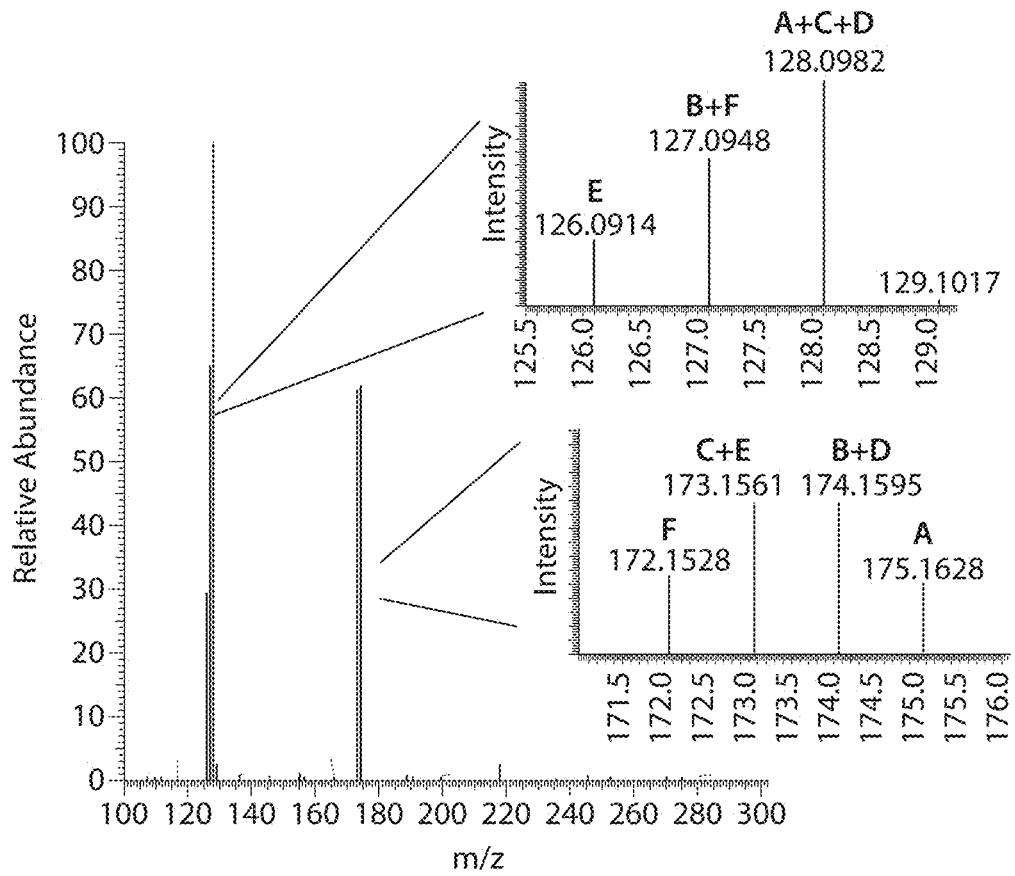
FIG. 6D is a schematic of a mass spectrum of the reporter ion distribution of a 1:1:1:1:1:1 mixture of labeled peptide, according to certain embodiments.
FIG. 6E is a comparison of the multiplexing capacity of a conventional label system and the multiplexing capacity of the mass spectrometry tags described herein, according to one set of embodiments.

To test the performance of CMT reagents for reporter ion based quantification, yeast whole cell lysate (YWCL) tryptic digest and analyzed reporter ion fragmentation via nano-LC-MS/MS were labeled. Unexpectedly, in addition to the predicted reporter ion series corresponding to fragmentation of the Lysine α/β bond, it was observed a second ion arising from cyclization of the expected RI and loss of dimethylamine (FIG. 5A). Essentially a second level of isobaricity, it was reasoned that the information contained in this secondary reporter ion series could be used to extract quantitative information from multiple tags with the same primary reporter ion isotope composition. To evaluate this strategy, a sixplex CMT reagent set (FIG. 6A) with two series of overlapping reporter ions (FIG. 6B, FIG. 6D) was synthesized. To deconvolute the contributions of each tag in the presence of overlapping reporter ions, a system of linear equations (FIG. 6C) was developed. Since these equations scale with increasing amounts of isotopes per tag, this combinatorial reporter ion strategy has the potential to significantly increase multiplexing density (FIG. 6E)

Before evaluating the effectiveness of the CMT approach, the fragmentation characteristics of labeled YWCL peptides was first analyzed by surveying HCD collision energy (CE) on an Orbitrap Fusion instrument. It was demonstrated that CMT labelled samples generate robust reporter ion (RI) signal over a range of CE, with median combined (primary+ secondary RI) signal intensity observed to be maximal at a CE 30. It was also found that secondary reporter ion intensity increased with increasing collision energy.

To evaluate the utility of the CMT approach for quantitative proteomics studies, YWCL tryptic digest was labeled with each of our sixplex reagents along with those of a commercial sixplex reagent. When compared to YWCL samples labelled with TMT (Proteome Sciences), CMT labelled samples performed similarly in terms of number of peptides identified, and estimated labeling percentage (>97% in all cases). For duplex mixing, it was found that both the primary and secondary reporter ion series of CMT reagents faithfully reported mixing ratios across an order of magnitude with similar accuracy to measurements made with TMT labeled samples. It was observed that while both CMT reporter ion series accurately reflected mixing ratios, the reporter ion splitting ratio was influenced by the presence or absence of a highly mobile proton on the labeled precursor peptide.

For samples containing mixtures of all six CMT reagents, a series of mathematical steps were required to arrive at CMT tag contributions to the overall RI signals observed. In addition to the series of linear equations, isotopic envelope contributions from each tag to RI intensities must also be corrected. While such corrections are also necessary with traditional isobaric reagents, the combinatorial nature of CMT necessitated a revision of established methods. Since reporter ions shared by two or more CMT tags can have tag specific isotopic envelopes (arising from differences in the isotopic purities of synthetic precursors of each reagent), relative contributions of each CMT reagent to overall signal must be established before deisotoping algorithms can be used. However since these relative contributions cannot be precisely known until deisotoping is achieved, a crude estimate of the fractional contribution of each tag to the reporter ion signal was calculated using the equations described in FIG. 6C. These crude values were then used to estimate the relative contributions to the signal arising from isotopic impurities in each reagent, and these values are used to obtain a better estimate of the true relative CMT reagent contributions to the overall RI signal. This process was iterated until the input and updated CMT reagent contributions converge to the true value.

Importantly, no significant difference was observed between the two reagent systems in terms of number of peptides identified or quantified, demonstrating the applicability of the CMT approach to complex samples with peptide concentrations varying by several orders of magnitude. Importantly, the way in which CMT tags were mixed did not significantly affect measurement accuracy in sixplex mixtures, although mixing arrangement did affect convergence time for the iterative deisotoping process.

Next, the ability of the CMT system to accurately and quantitatively distinguish differences between complex samples was explored. Liver homogenate tryptic digests from 3 different inbred mouse strains were labelled with both CMT and TMT tags. Then the ability of these two isobaric reagent sets to accurately measure differences between two strains in triplicate, as well as between both male and female specimens derived from all three strains using a single measurement per sample, was compared. Importantly, peptide and protein identification rates were comparable between the two labeling strategies. Hierarchical clustering and principle component analysis (PCA) was used to evaluate the effectiveness of each labeling system at quantitatively distinguishing between sample types. In the triplicate experiments, both CMT and TMT effectively distinguished samples based on strain. It was found quantitative accuracy between triplicate measurements to be similar at both the peptide and protein level. This lead to triplicate measurements associating tightly with each other by both hierarchical clustering and principle component analysis.

In the second experiment, both reagent systems reliably quantified differences between gender, strain, and evolutionary separation between strains. A striking demonstration of the quantitative similarity between the two reagent systems is observed by PCA, where quantitative results obtained by the two methods were indistinguishable over 5 principle components. As evidenced by hierarchical clustering, the liver proteomes were well differentiated by both reagent systems. In particular, the laboratory strain (B6) is clearly differentiated from the two wild-derived strains (CAST/PWK), while the wild-derived strains themselves form distinct clusters.

High throughput mass spectrometry-based quantitative proteomics is emerging as a powerful strategy for uncovering biological mechanisms, biomarker discovery and for understanding disease states. Although advances in instrumentation are continually increasing the speed and depth at which samples can be analyzed, increases in isobaric multiplexing density would be beneficial for several reasons, regardless of improvements in instrument speed.

First, mass spectrometry based proteomics experiments often operate in data-dependent mode, where ions are chosen for MS2 sequencing based on a prior MS1 scan and a set of selection rules. As a result, while the number of peptides identified from run to run is relatively constant for similar samples, the stochastic nature of peak picking results in an imperfect overlap in peptide identifications from run to run. Therefore, only those peptides or proteins that are reliably detected across all mass spectrometry runs can be compared when the sample number exceeds the multiplexing capacity of the quantitative strategy. Since reproducible identification is correlated with protein abundance, the practical consequence of this is that often only the most abundant proteins in the proteome of interest are quantifiable across all samples in large studies. This establishes a crippling paradox in certain experimental settings. For instance, large sample numbers are needed in order to statistically identify with confidence important biomarkers or to uncover proteomic differences associated with phenotypic or disease states. However, these proteins of interest are frequently of low abundance within the proteome, and therefore are prone to irreproducible quantification across multiple mass spectrometry experiments. Increasing multiplexing capacity is therefore critical for in-depth high throughput proteomics (such as clinical proteomics) of large sample numbers.

Second, a principle advantage of isobaric labeling is the ability to mix samples early in the sample preparation workflow. This not only increases sample preparation throughput, but eliminates variability associated with inconsistent sample treatment. Additionally, simultaneous measurement of multiplexed reporter ions allows direct comparison of relative abundance across mixed samples under instrument conditions that are necessarily identical. The magnitude of these advantages should increase with increasing multiplexing capacity of isobaric tags. Finally, any increases in multiplexing capacity will directly lead to the ability to analyze more samples in a given amount of time regardless of instrument speed. In order for large scale quantitative proteomics studies to be routinely feasible, both instrument speed and multiplexing capacity will likely need to improve.

While the multiplexing capacity of all isobaric labeling strategies can be increased by increasing the size of the isobaric tag, the CMT strategy has intrinsically higher multiplexing density for a given number of isotopes per tag than conventional isobaric reagents. For instance, with the current reagent structure, 25-Plex CMT is possible using only 5 isotopes per reagent, more than a two-fold improvement over TMT (FIG. 6E). Theoretically, the influence of the tag on the chromatographic and ionization properties of labeled peptides should increase with increasing tag size. This may partially explain why increasing isobaric reagent size has been shown to negatively impact protein identification rates.

An additional benefit of the CMT scaffold reported herein is its relatively quick, easy, and high yielding synthesis. The predominantly solid-phase nature of the synthesis enables a significant amount of automation and parallelization on standard peptide synthesizers, and eliminates laborious purification of intermediates. Indeed, with all protected amino acid groups in-hand, parallel synthesis and purification of multiple CMT free-acid isotopologues can be completed in approximately 1 week. Further, the ready availability of lysine, acetic acid, and formaldehyde isotopologues should allow for rapid, cost effective, large scale synthesis of CMT isobaric tags, potentially enabling large scale isobaric labeling of samples prior to enrichment for post-translational modifications.

When evaluating the quantitative performance of CMT, it is clear that in its current implementation CMT quantitative precision different than to that of TMT. An approximately 2 fold higher CV was consistently observed for CMT measurements across a variety of instruments and experimental designs. Several potential explanations exist for the increased variability of CMT measurements in comparison to those made with TMT. These include variability introduced by the iterative deisotoping process, amine-reactive impurities in the CMT reagents, variability inherent to dual reporter ion fragmentation, RI interference by coincidentally isobaric peptide side chain fragment ions, increased susceptibility to co-isolation interference, or variability introduced by the deconvolution of CMT signal.

Importantly, the same approximately 2-fold increase in measurement variability was observed over that of TMT in YWCL duplex mixing experiments with 2 Da reporter ion spacing and no requirement for signal deconvolution. This suggests that CMT signal deconvolution and iterative deisotoping do not significantly contribute to increased CMT measurement variability. Since co-isolation interference does not exist when identical proteomes are differentially labeled, these experiments also rule out increased susceptibility to interference as a potential source of decreased measurement precision. Most likely this effect is due to minor impurities present in the CMT sixplex reagents.

This example clearly demonstrate that combinatorial utilization of multiple reporter ion series can accurately convey quantitative differences between complex proteomes, theoretically enabling significant improvements in the multiplexing capacity of isobaric reagents. While the current structure is limited to two differential 13C and a single differential 15N between primary and secondary reporter ions, architectures that would allow for more differential 13C and 15N should enable rapid expansion of multiplexing capacity to levels compatible with high throughput screening.

Figure 7:
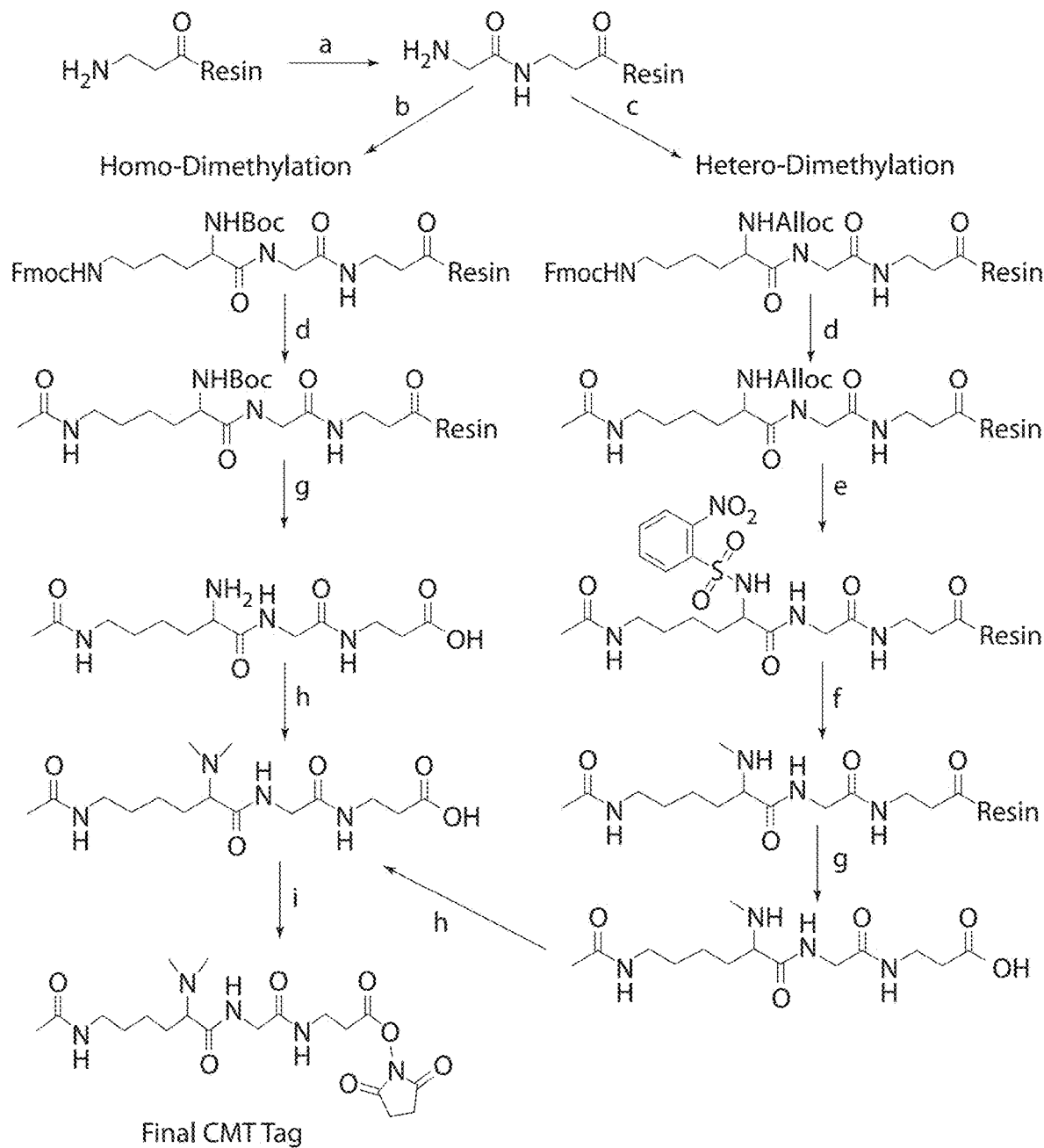
FIG. 7 is a synthetic scheme for a mass spectrometry tag, according to certain embodiments.

FIG. 7 shows the synthesis of CMT Isobaric Tags, wherein: A)(i) Fmoc-bAla-OH (2 eq), HATU (2 eq), DIPEA (4 eq) (ii) Piperidine:DMF 3:7 B) (i) Boc-Lys(Fmoc)-OH (2 eq), HATU (2 eq), DIPEA (4 eq) (2) Piperidine:DMF 3:7 C) (i) Alloc-Lys(Fmoc)-OH (2 eq), HATU (2 eq), DIPEA (4 eq) (2) Piperidine:DMF 3:7 D) (i) AcOH (2 eq), HATU (2 eq), DIPEA (4 eq) E) (i) tetrakis(thriphenylphosphine)palladium (0) (0.5 eq), CHCl3:AcOH:NMM 37:2:1 (ii) 2-nitrophenylsulfonyl chloride (4 Eq), 2,4,6-trimethylpyridine (10 Eq) F) (i) 1-methyl-1,3,4,6,7,8-hexahydro-2H-pyramido[1,2-a]pyrimidine (4 Eq), methyl-4-nitrobenzoate (4 Eq) (ii) 2-mercaptoethanol (5 Eq), 1,8-diazabicycloundec-7-ene (10 Eq) G) Trifluoroacetic acid:water:triisopropylsilane 95:2.5:2.5 and H) Formaldehyde (4 Eq), NaCNBH3 (10 Eq) i) N,N'-Disuccinimyidyl carbonate, DIPEA, ACN.

Figure 8A:
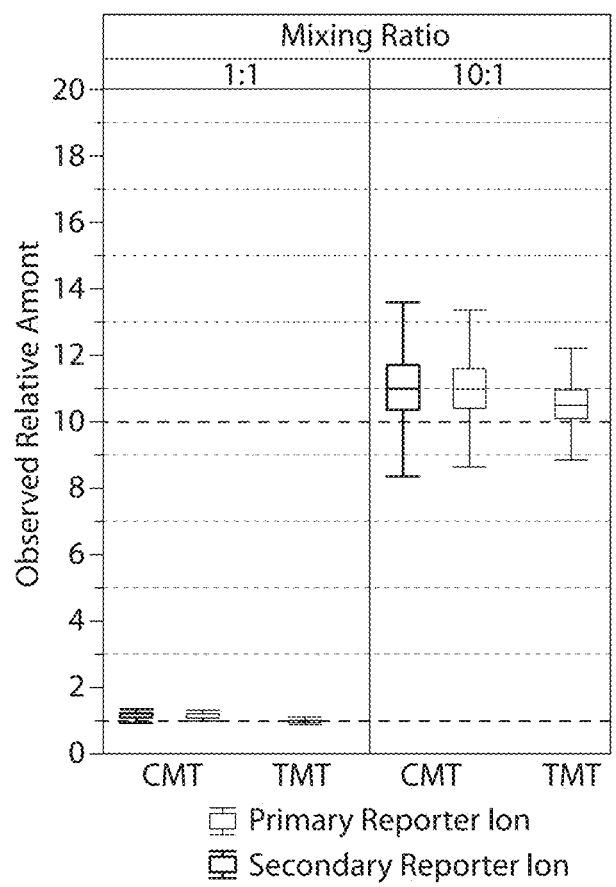
FIG. 8A is a plot of observed relative amount per mixing ratio for a conventional tag and a tag, described herein, according to certain embodiments.
Figure 8B:
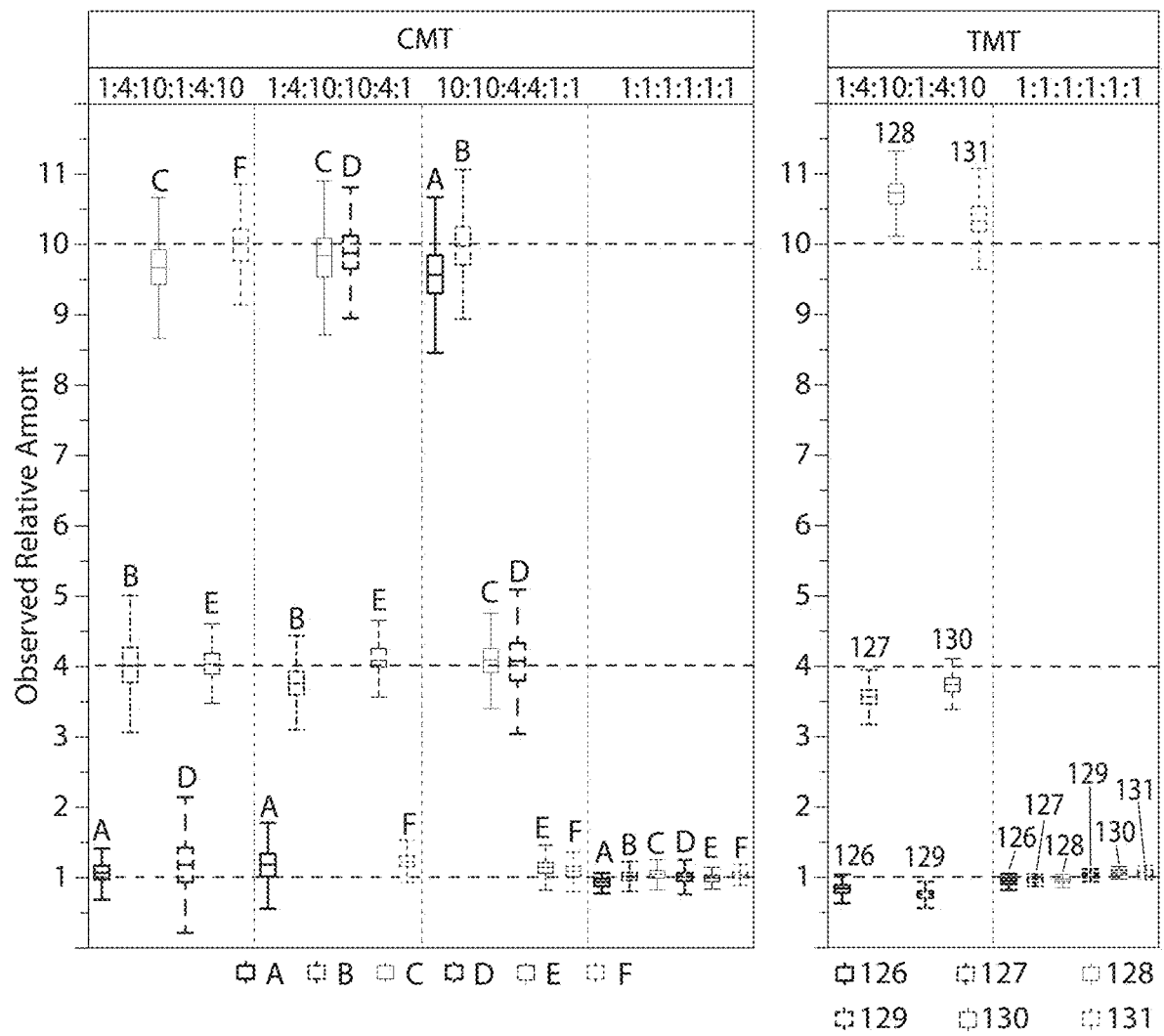
FIG. 8B is a plot of observed relative amount per mixing ratio for a conventional tag and a tag, described herein, according to one set of embodiments.
Figure 8C:
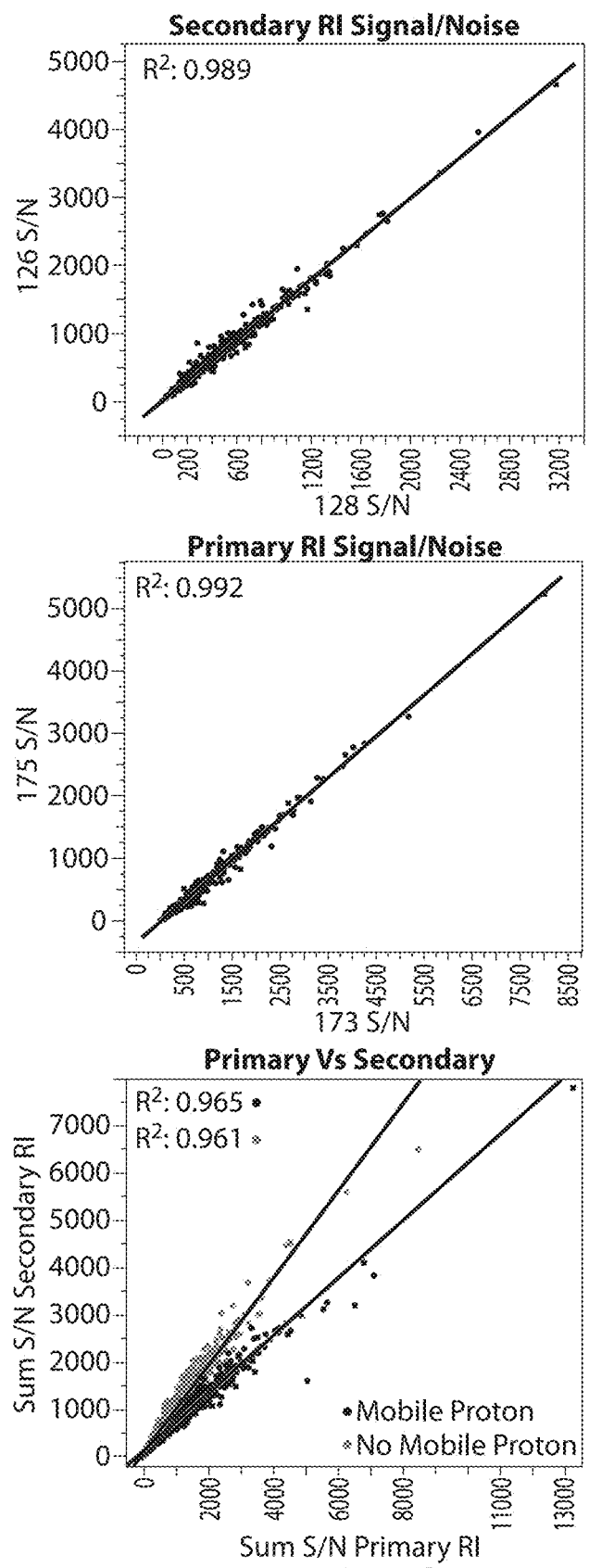
FIG. 8C is signal to noise ratio plots for various signals, according to certain embodiments.

FIG. 8 shows the iterative process for CMT isotopic envelope correction used for deconvolution. FIG. 8A shows the isotopic envelopes correction is achieved with CMT reporter ion signals in a two-step process. When computing fractional tag contribution in a sample of unknown mixing ratio, approximate relative tag contributions to the signal are computed as in FIG. 6C based on measured raw reporter ion intensities. From these computed CMT tag contributions, isotopic envelope distortion is estimated based on previously measured values for individual tags, and the raw reporter ion intensities are corrected based on this estimated distortion. This process is iterated until the calculations converge. Converged values are then normalized based on the fraction of the isotopic envelope contributed by the monoisotopic peak.

FIG. 8B shows a graphical representation of iterative deisotoping on idealized mixtures. Based on measured isotopic impurities for each tag, expected raw relative reporter ion intensities were calculated for theoretical sixplex mixing ratios of 1:1:1:1:1:1 (left), and 1:4:10:1:4:10 (right). Iterative deisotoping of the theoretical signal intensities and the results after each iteration of the process are shown, as well as the final normalization step.

Figure 9A:
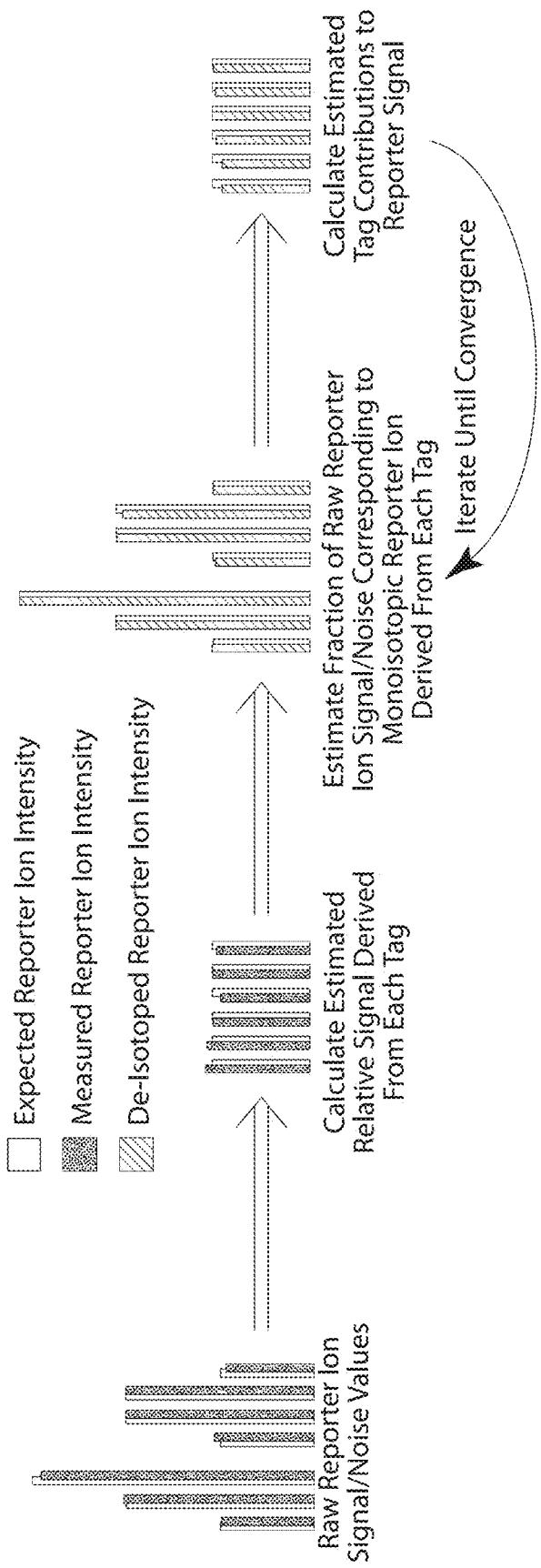
FIG. 9A is a schematic of a deconvolution method, according to one set of embodiments.

FIG. 9A shows a CMT and TMT YWCL mixing experiments that demonstrated accurate determination of input mixing ratios over an order of magnitude. FIG. 9A shows box and whisker plots that demonstrate that CMT and TMT labeling systems have comparable variability of measurement over mixing ratios spanning an order of magnitude. CMT reagents A and B, along with TMT 129 and 131, were used to label YWCL tryptic digests. Labeled samples were mixed at both equal and 10:1 mixing ratios, and analyzed on a Q Exactive instrument. Ratios between samples were determined by comparing the ratios between 126/128 (CMT Secondary), 175/173 (CMT Primary), and 129/131 (TMT).

Figure 9B:
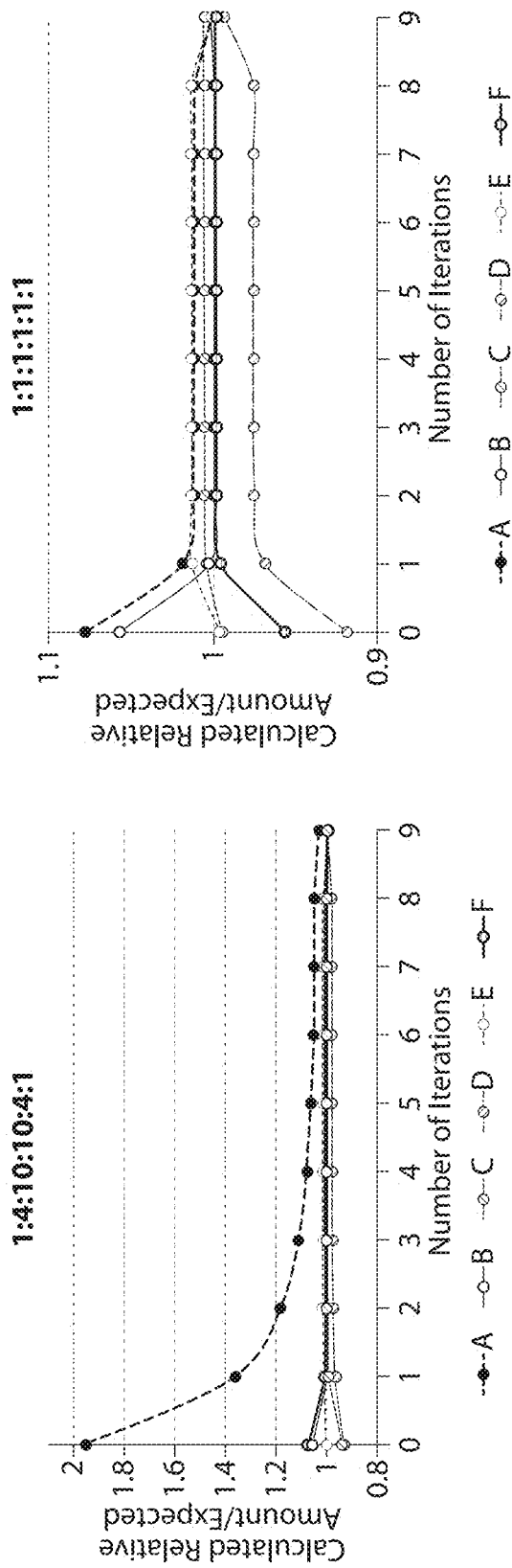
FIG. 9B is a graphical representation of iterative deconvolution on idealized mixtures, according to certain embodiments.

FIG. 9B shows the TMT sixplex reagents that were used to label YWCL tryptic digests. Labeled samples were mixed at combinations of 1:4:10 ratios, as well as equal mixing ratios, and analyzed on a Q Exactive instrument. Contributions of individual CMT labels to overall signal were calculated from the equations in FIG. 6C.

FIG. 9C shows the duplex mixing data demonstrating that ratios within reporter ion series, but not between them, are reliably reproducible. The splitting ratio between primary and secondary reporter ions is correlated to the presence or absence of a highly mobile protein on the labeled precursor peptide.

Example 2

This example described the materials and method used in Example 1.

Reagents: Aloc-Lys(Fmoc)-OH was obtained from Advanced Chemtech. Fmoc-βAla-Wang resin (RFX-1344-PI) was from Peptides International. 1-[Bis(dimethylamino)methylene]-1H-1,2,3-triazolo[4,5-b]pyridinium 3-oxid hexafluorophosphate (HATU) was purchased from Accela Chembio Inc. Dimethylformamide (DMF) and dichlormethane (DCM) were obtained from VWR. All other reagents were obtained from Sigma-Aldrich. All reagents were used without further purification. Mouse liver samples were obtained from the Jackson Laboratory.

Fmoc-Gly-OH synthesis: Glycine-1-$^{13}$C—OH, Glycine-$^{13}$C2—OH, and Glycine-$^{13}$C2$^{15}$N—OH were Fmoc-protected using Fmoc-Chloride according to the method of Cruz and co-workers.

CMT Synthesis: Isobaric tags were synthesized via solid phase synthesis (Wang Resin), using a combination of automated and manual methods. Automation was achieved with a Symphony X peptide synthesizer (Protein Technologies Inc.).

Fmoc Deprotection: 5 mL of a 30% (v/v) solution of piperidine in dimethylformamide (DMF) was added to the reaction vessel, and the resin was agitated for 10 minutes with nitrogen bubbling. Resin was subsequently washed 3 times with 5 mL of DMF.

Amide coupling reactions: All reagents were dissolved in N-methyl-2-pyrolidone (NMP). 1.5 mL of a 0.2 M solution of carboxylic acid and 1.5 mL of a 0.195 M solution of 1-[Bis(dimethylamino)methylene]-1H-1,2,3-triazolo[4,5-b] pyridinium 3-oxid hexafluorophosphate (HATU) were added to the preactivation vessel, followed by 1.5 mL of a 0.4 M solution of Diisopropylethylamine (DIPEA). After mixing via nitrogen bubbling for 30 seconds, the coupling solution was transferred to the reaction vessel containing 150 moles of free amine. Resin was agitated for 20 minutes with nitrogen bubbling, washed once with 5 mL of DMF, and the coupling cycling was repeated 1 additional time.

Aloc Deprotection: 0.2 equivalents of Tetrakis(triphenylphosphine)palladium(0) were suspended in 5 mL of a 37:2:1 mixture of chloroform, acetic acid, and N-methylmorpholine, added to the reaction vessel, and agitated with nitrogen bubbling for 1 hour, followed by a DCM wash. This deprotection reaction was repeated an additional 2 times, and finally the resin was rinsed 5 times each with 5 mL of 0.5% DIPEA in DMF and 0.5% sodium diethylthiocarbamate in DMF.

NBS Protection: NBS protection and methylation were done in accordance with the methods published by Biron[20] and Miller[21]. Briefly, 4 eq. of 2-nitrobenzenesulfonyl chloride was dissolved in 5 mL of NMP, and 10 eq of 2,4,6-trimethylpyrisine were added. The protection mixture was added to the reaction vessel with nitrogen agitation for 15 minutes, followed by washing with DMF 3 times.

Monomethylation: 4 eq. of methyl 4-nitrobenzenesulfonate in 4 mL of DMF were added to the reaction vessel, followed by 4 equivalents of neat 1-methyl-1,3,4,6,7,8-hexahydro-2H-pyrimido[1,2-a]pyrimidine. The mixture was agitated for 30 minutes with nitrogen bubbling, and washed three times with DMF. This reaction was repeated 1 additional time.

NBS Deprotection: A solution of 2-mercaptoethanol (10 eq.) and 1,8-Diazabicycloundec-7-ene (5 eq.) in NMP (5 mL) was mixed in the reaction vessel for 5 minutes, drained and rinsed with NMP. The deprotection was repeated 1 additional time.

Decanoic Acid Capping

Following any stage involving acylation of an amino group, any unreacted amine was capped by coupling with 10 molar equivalents of decanoic acid using the standard amino acid coupling protocol.

Resin Cleavage: Resins were agitated for 3 hours in trifluoroacetic acid (TFA) containing 2.5% each of water and triisopropylsilane. Cleavage reactions were filtered into glass vials, and resin was washed 2 times with 2 mL of cleavage buffer. Cleaved solutions were evaporated to dryness under a stream of nitrogen gas, resuspended in a 1:1 mixture of acetonitrile and water, frozen and lyophilized overnight.

Reductive Methylation: Compounds were dissolved in citrate buffer (pH 5.5), and formaldehyde (4 eq.) was added, followed by dropwise addition of 10 eq of sodium cyanoborohydride (5 M in 1 M NaOH). The reaction was stirred for 2 hours, quenched with 1% TFA to a final pH of 2.5, and stirred for an additional 2 hours. Methylated compounds were purified by solid phase extraction on SEP-PAK C18 cartridges, with washes of 0.1% TFA in water and elution in 0.1% TFA/5% Acetonitrile. Eluted compounds were frozen and lyophilized overnight.

NHS-Activation: 10 eq of disuccinimidyl carbonate was dissolved in anhydrous acetonitrile and added to 1 eq of tag free acid. 4 eq of DIPEA was added, and the reaction was allowed to proceed overnight. Crude reaction mixture was directly purified via HPLC-MS (Agilent 12 Series) on a semi-preparative C18 column (Agilent) using mass-triggered fractionation over a linear gradient from 100% buffer A (1% Acetonitrile, 0.1% TFA) to 10% Buffer B (0.1% TFA in Acetonitrile).

Peptide labeling: To peptide solutions in 0.1 M EPPS (pH 8.0) was added 4 equivalents by weight of NHS activated tag (10 ug/uL in anhydrous acetonitrile). Labeling reactions were incubated for 2 hours at room temperature, quenched with 5% hydroxylamine (0.5% final) for 15 minutes, and finally 0.1% TFA was added to adjust the pH to 2.5. Samples were desalted via C18 STAGE tips.

Labelled samples were separated on a fused silica column packed in-house with C18 resin using a Nano-UPLC (Thermo), and analyzed on Orbitrap Fusion, or Q Exactive mass spectrometers, operating in data-dependent mode. For Orbitrap Fusion experiments MS3 spectra[10] were acquired using a multi-notch strategy[9] and HCD fragmentation using an activation energy of 30 for CMT experiments, and 50 for TMT experiments. For Q-Exactive experiments, step-wise HCD activation at energy equal to 20, 35, and 30 were performed for CMT experiments, and 25, 30 and 40 for TMT experiments.

Yeast Whole Cell Lysate Digest Preparation: The yeast strain was BY4742 MAT α, derived from S288c. The yeast minimal media was comprised of yeast nitrogenous base with amino acids, ammonium sulfate, and 2% glucose. Three starter cultures were grown in raffinose-containing minimal media overnight from individual colonies. Cultures were grown to reach an optical density (OD) of 0.6 and then harvested.

Yeast cultures were harvested by centrifugation, washed two times with ice cold deionized water, and resuspended at 4° C. in a buffer containing 50 mM HEPES pH 8.5, 8 M urea, 75 mM NaCl, protease (complete mini, EDTA-free), and phosphatase (PhosphoStop) inhibitors (Roche). Cells were lysed using the MiniBeadbeater (Biospec) in microcentrifuge tubes at maximum speed for three cycles of 60 sec each, with 3 min pauses between cycles to avoid overheating of the lysates. After centrifugation, lysates were transferred to new tubes. The protein concentration was determined in the lysate using the bicinchoninic acid (BCA) protein assay (Thermo Fisher Scientific).

Proteins were subjected to disulfide reduction with 5 mM tris(2-carboxyethyl)phosphine (TCEP), (room temperature, 25 min) and alkylation with 10 mM iodoacetamide (room temperature, 30 min in the dark). Excess iodoacetamide was quenched with 15 mM dithiothreitol (room temperature, 15 min in the dark). Methanol-chloroform precipitation was performed prior to protease digestion. In brief, four parts neat methanol was added to each sample and vortexed, one part chloroform was added to the sample and vortexed, and three parts water was added to the sample and vortexed. The sample was centrifuged at 4000 RPM for 15 min at room temperature and subsequently washed twice with 100% acetone, prior to air-drying.

Samples were resuspended in 8 M urea, 50 mM HEPES, pH 8.5. The protein extract was then diluted to 1 M urea with 50 mM HEPES pH 8.5 and digested at room temperature for 16 hrs with LysC protease at a 100:1 protein-to-protease ratio. Trypsin was then added at a 100:1 protein-to-protease ratio and the reaction was incubated 6 hrs at 37° C.

Mouse Liver Extract Digest Preparation: Liver tissue was homogenized in 1 ml of lysis buffer (1% SDS, 50 mM Tris (pH 8.8) and Roche complete protease inhibitors). Samples were reduced with 5 mM dithiothreitol for 30 minutes at 37° C. followed by alkylation with 15 mM for 30 minutes at room temperature in the dark. The alkylation reaction was quenched by adding 5 mM dithiothreitol for 15 minutes at room temperature in the dark. A 500 uL aliquot was then methanol/chloroform precipitated. Firstly, 2 ml of ice cold methanol was added to the sample and vortexed. Next, 500 uL ice cold chloroform was added and then vortexed. Lastly, 1.5 ml of cold water was added and vortexed. The samples were then centrifuged at 4000 rpm for 20 minutes. The top layer above the protein pellet was removed and additional methanol was added before overtaxing. Samples were centrifuged at 4000 rpm for 10 minutes and the supernatant was removed. The protein pellets were washed a further two times with cold methanol. The samples were allowed to air dry before resuspending the samples in 1 ml of 8 M urea and 50 mM Tris (pH 8.8) before diluting the urea concentration down to ~1.5 M urea with 50 mM Tris. Proteins were quantified using a BCA assay. Protein was then digested using a combination of Lys-C/trypsin at an enzyme-to-protein ratio of 1:100. Firstly, protein was digested overnight with Lys-C followed by 6 hour digestion with trypsin all at 37° C. Samples were then acidified using formic acid to approximately pH 3. Samples were then desalted using a SepPak column. Elutes were then dried using a vacuum centrifuge.

General Formulae for the Maximum Multiplicity of a Given Reagent Architecture

In order to deconvolute reporter ion signal algebraically, the number of resolvable isobaric channels (uniquely resolvable tags per isobaric set) is equal to one less than the sum of the amount of unique primary and secondary reporter ions that can be distinguished. For the tag architecture presented, the number of unique (primary and secondary) reporter ions that can be distinguished can be calculated algebraically. The generalized formula can be written for any system of primary and secondary reporter ions (not limited to the structures presented in this manuscript). Assuming all 13C and 15N isotopes can be differentially positioned on either of the primary and secondary reporter ions series, where C and N define the maximum number of 13C and 15N that can be labeled (in both ion series), the number of distinguishable reporter ions (Z) is described as $$Z = (N+1)(C+1)*2 - 1$$

For isobaric reagents such as TMT, which only generate a single reporter ion series, the maximal number of distinguishable channels Z can be written as:

$$Z = (N+1)(C+1)$$

The equations listed in FIG. 6C assume a limitation to the number of solvable isobaric tags of one less than the number of unique reporter ions that can be generated. This limitation arises from the fact that each reporter ion series are considered in isolation for these calculations, resulting in an underdetermined system when the number of tags is equal to the number of unique reporter ions. Theoretically, one could generate an additional equation relating primary to secondary reporter ion intensity based on an IF statement to separate those peptides with and without highly mobile protons, which would enable a number of tags equal to the number unique reporter. Since the reporter ion splitting ratio, while highly correlated to the presence or absence of highly mobile protons, is a less precise measurement that those between reporter ions within a series, the choice was made to not take advantage of this effect to increase the multiplicity of our reagents. More generally, in cases where the number of equations exceeds the number of encoded isobaric the square difference between observed ion pattern c and predicted ion pattern $\hat{c}^{33}$ reagent can also be minimized. The ratio of the channel mixing r was varied and Diff was minimized.

$$\min_r Diff(c, \hat{c}(\hat{r})) = \min_r \sum_i (\hat{c}_i(\hat{r}) - c_i)^2 \text{ with } \sum_i \hat{c}_i = 1 \text{ and } \sum_i c_i = 1$$

Searching for the mixing proportions which minimize the ion envelop similarity function is a standard multivariate optimization problem. Diff is defined as quadratic similarity function. An instance of convex optimization was therefore obtained and could solve the optimization problem with a simple local search solver as implemented by the fmincon function in MATLAB.

Example 3

This example describes the synthesis of mass spectrometry tags in Tables 1 and 2. This is a prophetic example. In general, the mass spectrometry tags in Tables 1 and 2 may be synthesized as outlined in Scheme 1, and described below, provided that the appropriate isotopic reagents are utilized.

Scheme 1: Synthesis of a mass spectrometry tag

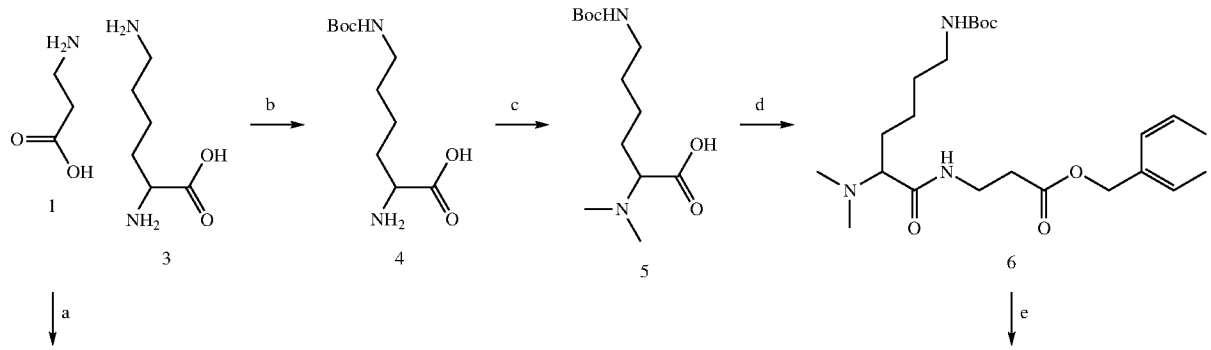

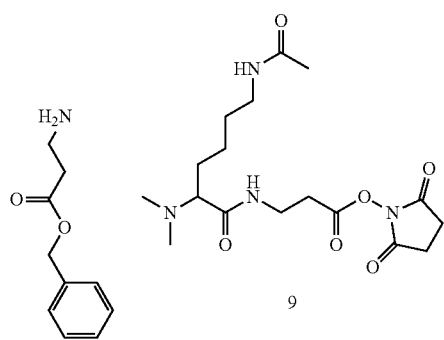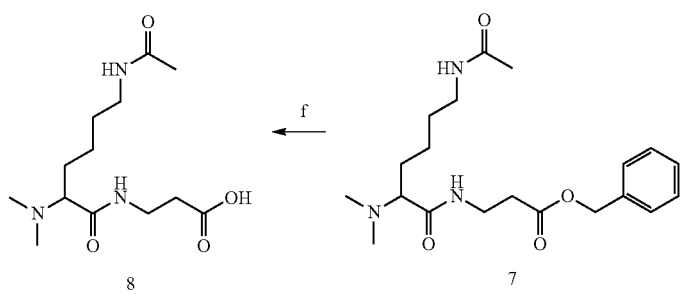

Scheme 1: Second-Generation CMT Solution Phase Synthesis Strategy. a) pTsOH, BnOH b) CuSO4, Boc2O, NaCHO3, c) Formaldehyde, NaBH4 d) (2), TMP, COMU e) (i) TFA (ii) TEA, AcCl f) H2, Pd/C g) Disuccinimidyl carbonate, DIPEA benzyl 3-aminopropanoate (2) and isotopic isomers thereof. To a solution of 3-aminopropionic acid (1) (4 g, 43.92 mMol) in toluene (50 mL) and benzyl alcohol 30 mL (288 mMol) was added p-toluenesulfonic acid monohydrate (10.02 g, 52.8 mMol). The solution was refluxed overnight under Dean-Stark conditions, after which the reaction was cooled to room temperature. Crude product was precipitated by addition of diethyl ether, and isolated by filtration. The retentate was washed two times with diethyl ether, followed by three washed with ethyl acetate and air dried to afford 2 as a white powder. Yield 12.1 g (78%)

benzyl 3-(amino-15N)propanoate 4-methylbenzenesulfonate (2b). To a solution of 3-(amino-15N)propionic acid (1b) (2 g, 22.20 mMol) in toluene (30 mL) and benzyl alcohol 15 mL (144 mMol) was added p-toluenesulfonic acid monohydrate (5.01 g, 26.4 mMol). The solution was refluxed overnight under Dean-Stark conditions, after which the reaction was cooled to room temperature. Crude product was precipitated by addition of diethyl ether, and isolated by filtration. The retentate was washed two times with diethyl ether, followed by three washed with ethyl acetate and air dried to afford 2b as a white powder. Yield 7.05 g (90%)

benzyl 3-(amino-15N)propanoate-1-13C4-methylbenzenesulfonate (2c). To a solution of 3-(amino-15N)propionic-1-13C acid (2 g, 21.96 mMol) in toluene (30 mL) and benzyl alcohol 15 mL (144 mMol) was added p-toluenesulfonic acid monohydrate (5.01 g, 26.4 mMol). The solution was refluxed overnight under Dean-Stark conditions, after which the reaction was cooled to room temperature. Crude product was precipitated by addition of diethyl ether, and isolated by filtration. The retentate was washed two times with diethyl ether, followed by three washed with ethyl acetate and air dried to afford 2c as a white powder. Yield 6.92 g (88%)

N6-(tert-butoxycarbonyl)lysine (4). N6-(tert-butoxycarbonyl)lysine was synthesized from Lysine hydrochloride (3) via the copper chelate according to the methods of Wiejak and co-workers. Lysine hydrochloride (3) (2 g, 11.01 mMol) was dissolved in 20 mL aqueous sodium bicarbonate (1.1 mM). CuSO4 pentahydrate (1.375 g, 5.51 mMol) in water (20 mL) was added under stirring, after which sodium bicarbonate (0.925 g, 11.01 mMol) was added. A solution of di-tert-butyl-dicarbonate (3.12 g, 14.31 mMol) in acetone (20 mL) was added dropwise, and the mixture was stirred for 24 hours, after which methanol (20 mL) was added, and the solution stirred for 12 hours. Ethyl acetate (25 mL), and water (25 mL) were added, and crude [Lys(Boc)]2Cu collected by filtration. The rentate was washed several times with water and air dried to yield a blue powder (2.4 g, 79%) The air-dried filtrate (2.4 g) was added to a stirred solution of 8-quinolinol (1.635 g, 11.26 mMol) in water (50 mL), and stirred for 5 h, following which copper (II) quinolinolate was removed via filtration and the retentate washed with water several times. The filtrates were extracted 3 times with ethyl acetate, and the aqeuous phase concentrated to dryness via rotary evaporation to yield (4) (2 g, 94%).

It should be understood that in certain embodiment (e.g., compounds in Table 3) that require mono-13C methylation of the alpha amine of lysine the following reaction may be used:

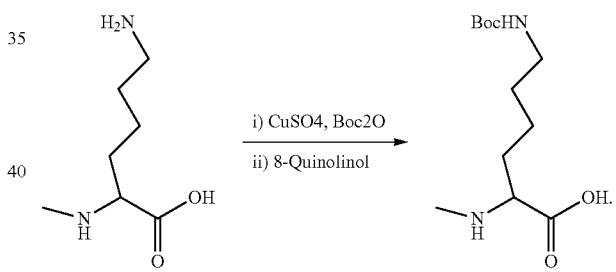

N6-(tert-butoxycarbonyl)-N2,N2-dimethyllysine (5a). Synthesis of (5a) was carried out according to a procedure adapted from that of Tajbakhsh and co-workers. To a stirred solution of H-Lys(Boc)-OH (16) (2.61 g, 10.6 mMol) and 37% (aq) formaldehyde (1.58 mL, 21.2 mMol) in trifluoroethanol (15 mL) was added NaBH4 (802 mg, 21.2 mMol). Starting at 30 minutes after addition of NaBH4, and every 30 minutes thereafter, reaction progress was followed by reversed phase LC-MS. When successive LC-MS runs showed no increase in reaction progress, 1 mMol of each of the formaldehyde solution and NaBH4 were added, and reaction progress was monitored as before. These additions were repeated until complete dimethylation of lysine was obtained. Upon complete conversion of (4a) to its dimethylated form (5a), the reaction was quenched with 1% acetic acid (50 mL), and solvents removed in vacuo. The crude product was resuspended in 1% acetic acid, and purified by reversed phase flash chromatography. Fractions containing pure product were combined and lyophilized to yield 2.29 g of a white crystalline material (79%).

N6-(tert-butoxycarbonyl)-N2,N2-di(methyl-13C)lysine (5b). Synthesis of (5b) was carried out according to a procedure adapted from that of Tajbakhsh and co-workers[34]. To a stirred solution of H-Lys(Boc)-OH (4) (1 g, 4.06 mMol) and 20% (aq) 13C-formaldehyde (1.259 □L, 812 mMol) in trifluoroethanol (15 mL) was added NaBH$_4$ (307 mg, 8.12 mMol). Starting at 30 minutes after addition of NaBH$_4$, and every 30 minutes thereafter, reaction progress was followed by reversed phase LC-MS. When successive LC-MS runs showed no increase in reaction progress, 0.4 mMol of each of the formaldehyde solution and NaBH$_4$ were added, and reaction progress was monitored as before. These additions were repeated until complete dimethylation of lysine was obtained. Upon complete conversion of (4) to its dimethylated form (5b), the reaction was quenched with 1% acetic acid (30 mL), and solvents removed in vacuo. The crude product was resuspended in 1% acetic acid, and purified by reversed phase flash chromatography. Fractions containing pure product were combined and lyophilized to yield 890 mg of a white crystalline material (79%).

benzyl 3-(6-((tert-butoxycarbonyl)amino)-2-(dimethylamino)hexanamido)propanoate (6a). To a heterogenous mixture of (5a) (391 mg, 1.425 mMol) and anhydrous dimethylformamide (DMF) (5 mL) stirred at 0° C. was added a solution of (1—Cyano-2-ethoxy-2-oxoethylidenaminooxy)dimethylamino-morpholino-carbenium hexafluorophosphate (COMU) (610 mg, 1.425 mMol) in anhydrous DMF. After complete dissolution of (6a) to form a yellow solution, 2,2,6,6-tetramethylpiperidine was added (481 □L, 2.85 mMol) and the solution was stirred for 30 seconds. A solution of (2a) (501 mg, 1.425 mMol) in anhydrous DMF (5 mL) was added, and the reaction was stirred for 10 minutes at 0° C. followed by 50 minutes at room temperature. Upon confirmation of complete consumption of (2a) by reversed phase LC-MS, the reaction was quenched by the addition of water (25 mL). The crude reaction mixture was purified directly by C18 chromatography (Buffer A–Water+0.1% acetic acid, Buffer B–Acetonitrile+0.1% acetic acid). Pure fractions were pooled and evaporated to dryness via lyophilization to provide (6a) as a white crystalline solid. 459 mg (65%).

benzyl 3-(6-((tert-butoxycarbonyl)amino)-2-(di(methyl-13C)amino)hexanamido)propanoate acetate (6b). To a heterogenous mixture of (5b) (524 mg, 1.91 mMol) and anhydrous dimethylformamide (DMF) (5 mL) stirred at 0° C. was added a solution of (1-Cyano-2-ethoxy-2-oxoethylidenaminooxy)dimethylamino-morpholino-carbenium hexafluorophosphate (COMU) (818 mg, 1.91 mMol) in anhydrous DMF. After complete dissolution of (5b) to form a yellow solution, 2,2,6,6-tetramethylpiperidine was added (587 μL, 3.48 mMol) and the solution was stirred for 30 seconds. A solution of (2a) (671 mg, 1.91 mMol) in anhydrous DMF (5 mL) was added, and the reaction was stirred for 10 minutes at 0° C. followed by 50 minutes at room temperature. Upon confirmation of complete consumption of (2a) by reversed phase LC-MS, the reaction was quenched by the addition of water (25 mL). The crude reaction mixture was directly applied to a reversed column purified by C18 chromatography (Buffer A–Water+0.1% acetic acid, Buffer B–Acetonitrile+0.1% acetic acid). Pure fractions were pooled and evaporated to dryness via lyophilization to provide (6b) as a white crystalline solid. 316 mg (34%).

benzyl 3-(6-(acetamido)-2-(dimethylamino)hexanamido)propanoate 2,2,2-trifluoroacetate (7a). A 1:1 solution of dichloromethane:trifluoroacetic acid (20 mL) was added to (6a) (615 mg, 1.241 mMol), and the solution was stirred at room temperature. Reaction progress was checked by reversed phase LC-MS, and upon complete removal of the boc protecting group, the solvent was removed by rotary evaporation. The reaction product was redissolved in water and evaporated to dryness by lyophilization. To a stirred solution of the crude product in anhydrous acetonitrile was added pyridine (0.201 mL, 2.482 mMol), and acetyl chloride (0.132 mL, 1.861 mMol), and the mixture was stirred at room temperature. Reaction progress was monitored by reversed phase LC-MS, and additional acetic anhydride added as needed to drive the reaction to completion. Upon completion, the reaction mixture was diluted with water, and evaporated to dryness in vacuo. The crude product was purified by reversed phase flash chromatography (Buffer A–Water+0.1% TFA, Buffer B–Acetonitrile+0.1% TFA). Fractions containing pure (7a) were pooled and dried by lyophilization to afford a clear oil (400 mg, 66%).

benzyl 3-(6-(acetamido-13C2)-2-(dimethylamino)hexanamido)propanoate (7b). A 1:1 solution of dichloromethane:trifluoroacetic acid (20 mL) was added to (6a) (459 mg, 927 mMol), and the solution was stirred at room temperature. Reaction progress was checked by reversed phase LC-MS, and upon complete removal of the boc protecting group, the solvent was removed by rotary evaporation. The reaction product was redissolved in water and evaporated to dryness by lyophilization. To a stirred solution of the crude product in anhydrous acetonitrile was added anhydrous pyridine (150 uL, 1.86 mMol), and acetyl 13C2 chloride (112 mg, 1.39 mMol), and the mixture was stirred at room temperature. Reaction progress was monitored by reversed phase LC-MS, and additional acetic anhydride added as needed to drive the reaction to completion. Upon completion, the reaction mixture was diluted with water, and evaporated to dryness in vacuo. The crude product was purified by reversed phase flash chromatography (Buffer A–Water+0.1% TFA, Buffer B–Acetonitrile+0.1% TFA). Fractions containing pure (7b) were pooled and dried by lyophilization to afford a clear oil (160 mg).

benzyl 3-(6-acetamido-2-(di(methyl-13C)amino)hexanamido)propanoate (7c). A 1:1 solution of dichloromethane:trifluoroacetic acid (20 mL) was added to (6b) (316 mg, 636 μMol), and the solution was stirred at room temperature. Reaction progress was checked by reversed phase LC-MS, and upon complete removal of the boc protecting group, the solvent was removed by rotary evaporation. The reaction product was redissolved in water and evaporated to dryness by lyophilization. To a stirred solution of the crude product in anhydrous acetonitrile was added anhydrous pyridine (103 uL, 1.27 mMol), and acetic anhydride (90 uL, 954 uMol), and the mixture was stirred at room temperature. Reaction progress was monitored by reversed phase LC-MS, and additional acetic anhydride added as needed to drive the reaction to completion. Upon completion, the reaction mixture was diluted with water, and evaporated to dryness in vacuo. The crude product was purified by reversed phase flash chromatography (Buffer A–Water+0.1% TFA, Buffer B–Acetonitrile+0.1% TFA). Fractions containing pure (7b) were pooled and dried by lyophilization to afford a clear oil (100 mg, 32%).

3-(6-acetamido-2-(dimethylamino)hexanamido)propanoic acid (8a). Me2-Lys(Ac)-bAla-Obn trifluoroacetate (7a) (400 mg, 0.824 mMol) was exchanged to its hydrochloride salt by solid phase extraction using an Oasis HLB cartridge (Waters). Bound (7a) was washed with 0.05% HCl, and eluted with 60% acetonitrile in 0.05% HCl. Eluted (7a) hydrochloride salt was dried via lyophilization, and used in the proceeding step without further purification. To a round bottom flask equipped with a stir bar, isopropanol, (7a), and Pd/C (10% w/w) were added, and the flask was repeatedly evacuated and back-filled with nitrogen gas several times.

The flask was evacuated a final time, and a balloon containing approximately 4l of hydrogen gas was affixed to the top of the flask. The reaction was intensely stirred for several hours, and reaction progress was monitored by reversed phase LC-MS. When complete conversion to the free carboxylic acid (8a) was achieved, the reaction mixture was filtered and the filtrate evaporated to dryness via speedvac. The product (8a) was obtained as a crystalline solid that was used without further purification (200 mg, 84%)

2,5-dioxopyrrolidin-1-yl 3-(6-acetamido-2-(di(methyl-13C)amino)hexanamido)propanoate formate (9b). Me2-Lys(Ac)-Ala-Obn trifluoroacetate (7b) (32 mg, 66 uMol) was exchanged to its hydrochloride salt by solid phase extraction using an Oasis HLB cartridge (Waters). Bound (7b) was washed with 0.05% HCl, and eluted with 60% acetonitrile in 0.05% HCl. Eluted (7b) hydrochloride salt was dried via lyophilization, and used in the proceeding step without further purification. To a round bottom flask equipped with a stir bar, isopropanol, (7b), and Pd/C (10% w/w) were added, and the flask was repeatedly evacuated and backfilled with nitrogen gas several times. The flask was evacuated a final time, and a balloon containing approximately 4l of hydrogen gas was affixed to the top of the flask. The reaction was intensely stirred for several hours, and reaction progress was monitored by reversed phase LC-MS. When complete conversion to the free carboxylic acid (8b) was achieved, the reaction mixture was filtered and the filtrate evaporated to dryness via speedvac. The product (8b) was obtained as a clear oil that was treated with disuccinimidyl carbonate (50.6 mg, 0.198 mMol) and anhydrous pyridine (10.7 uL, 132 uMol) and stirred overnight. After 12 hours, the directly purified via preparative HPLC-MS (Buffer A–Water+0.1% formic acid, Buffer B–Acetonitrile+0.1% formic acid) using mass-triggered fractionation. Purified fractions were snap frozen in liquid nitrogen as they eluted from the column, and pooled purified fractions were dried via lyophilization to yield (9b) as a clear oil (15.5 mg, 61% yield).

2,5-dioxopyrrolidin-1-yl 3-(6-(acetamido-13C2)-2-(dimethylamino)hexanamido)propanoate formate (9c). Me2-Lys(Ac)-Ala-Obn trifluoroacetate (7c) (24 mg, 49 uMol) was exchanged to its hydrochloride salt by solid phase extraction using an Oasis HLB cartridge (Waters). Bound (7c) was washed with 0.05% HCl, and eluted with 60% acetonitrile in 0.05% HCl. Eluted (7c) hydrochloride salt was dried via lyophilization, and used in the proceeding step without further purification. To a round bottom flask equipped with a stir bar, isopropanol, (7c), and Pd/C (10% w/w) were added, and the flask was repeatedly evacuated and backfilled with nitrogen gas several times. The flask was evacuated a final time, and a balloon containing approximately 4l of hydrogen gas was affixed to the top of the flask. The reaction was intensely stirred for several hours, and reaction progress was monitored by reversed phase LC-MS. When complete conversion to the free carboxylic acid (20c) was achieved, the reaction mixture was filtered and the filtrate evaporated to dryness via speedvac. The product (8c) was obtained as a clear oil that was treated with disuccinimidyl carbonate (38 mg, 0.148 mMol) and anhydrous pyridine (7.8 uL, 0.099 mMol) and stirred overnight. After 12 hours, the directly purified via preparative HPLC-MS (Buffer A–Water+0.1% formic acid, Buffer B–Acetonitrile+0.1% formic acid) using mass-triggered fractionation. Purified fractions were snap frozen in liquid nitrogen as they eluted from the column, and pooled purified fractions were dried via lyophilization to yield (9c) as a clear oil (13.5 mg, 71% yield).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A compound of Formula (III):

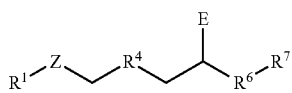
(III)

or an isotopic analogue thereof,
wherein:
- $R^1$ is selected from the group consisting of optionally substituted alkyl, optionally substituted acyl, optionally substituted aryl, and optionally substituted heteroaryl;
- Z is a nucleophilic group;
- $R^4$ is absent or selected from the group consisting of optionally substituted alkylene and optionally substituted heteroalkylene;
- E is a leaving group;
- $R^6$ is selected from the group consisting of optionally substituted alkylene and optionally substituted heteroalkylene; and
- $R^7$ is a reactive group.

2. The compound of claim 1, wherein:
- $R^1$ is selected from the group consisting of optionally substituted alkyl, optionally substituted —C(=O) $R^2$, optionally substituted aryl, and optionally substituted heteroaryl;
- $R^2$ is selected from the group consisting of optionally substituted alkyl, optionally substituted heteroalkyl, optionally substituted aryl, and optionally substituted heteroaryl;
- Z is selected from the group consisting of —NH—, —O—, and —S—;
- $R^4$ is absent or selected from the group consisting of optionally substituted alkylene and optionally substituted heteroalkylene;
- E is selected from the group consisting of optionally substituted thiol, optionally substituted amino, optionally substituted acyl, and optionally substituted heteroalkyl;
- $R^6$ is selected from the group consisting of optionally substituted alkylene and optionally substituted heteroalkylene; and
- $R^7$ is selected from the group consisting of optionally substituted heteroalkyl, substituted cycloheteroalkyl, optionally substituted heteroalkenyl, optionally substituted heteroaryl, alcohol, optionally substituted acyl, optionally substituted thiol, hydroxysuccinimide, and hydroxysulfosuccinimide.

3. The compound of claim 1, wherein the compound has the structure:

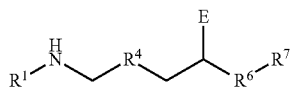

or an isotopic analogue thereof,
wherein:
- $R^1$ is selected from the group consisting of optionally substituted alkyl, optionally substituted —C(=O) $R^2$, optionally substituted aryl, and optionally substituted heteroaryl;
- $R^2$ is selected from the group consisting of optionally substituted alkyl, optionally substituted heteroalkyl, optionally substituted aryl, and optionally substituted heteroaryl;
- $R^4$ is absent or selected from the group consisting of optionally substituted alkylene and optionally substituted heteroalkylene;
- E is selected from the group consisting of optionally substituted thiol, optionally substituted amino, optionally substituted acyl, and optionally substituted heteroalkyl;
- $R^6$ is selected from the group consisting of optionally substituted alkylene and optionally substituted heteroalkylene; and
- $R^7$ is selected from the group consisting of optionally substituted heteroalkyl, substituted cycloheteroalkyl, optionally substituted heteroalkenyl, optionally substituted heteroaryl, alcohol, optionally substituted acyl, optionally substituted thiol, hydroxysuccinimide, and hydroxysulfosuccinimide.

4. The compound of claim 1, wherein the compound has the structure:

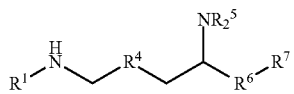

or an isotopic analogue thereof,
wherein:
- $R^1$ is selected from the group consisting of optionally substituted alkyl, optionally substituted —C(=O) $R^2$, optionally substituted aryl, and optionally substituted heteroaryl;
- $R^2$ is selected from the group consisting of optionally substituted alkyl, optionally substituted heteroalkyl, optionally substituted aryl, and optionally substituted heteroaryl;

R⁴ is absent or selected from the group consisting of optionally substituted alkylene and optionally substituted heteroalkylene;

each R⁵ is the same or different and selected from the group consisting of optionally substituted alkyl and optionally substituted heteroalkyl, optionally two R⁵ may be joined to form a ring;

R⁶ is selected from the group consisting of optionally substituted alkylene and optionally substituted heteroalkylene; and R⁷ is selected from the group consisting of optionally substituted heteroalkyl, substituted cycloheteroalkyl, optionally substituted heteroalkenyl, optionally substituted heteroaryl, alcohol, optionally substituted acyl, optionally substituted thiol, hydroxysuccinimide, and hydroxysulfosuccinimide.

5. The compound of claim 1, wherein the compound has the structure:

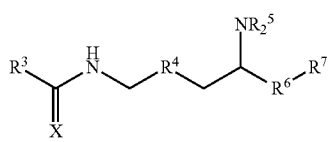

or an isotopic analogue thereof, wherein:
R³ is optionally substituted alkyl;
X is O or N;
R⁴ is absent or selected from the group consisting of optionally substituted alkylene and optionally substituted heteroalkylene;
each R⁵ is the same or different and selected from the group consisting of optionally substituted alkyl and optionally substituted heteroalkyl, optionally two R⁵ may be joined to form a ring;
R⁶ is selected from the group consisting of optionally substituted alkylene and optionally substituted heteroalkylene; and
R⁷ is a reactive group.

6. The compound of claim 1, wherein the compound has the structure:

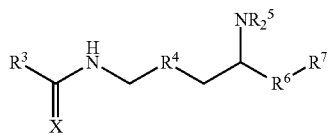

or an isotopic analogue thereof, wherein:
R³ is optionally substituted $C_{1-10}$ alkyl;
X is O or N;
R⁴ is absent or selected from the group consisting of optionally substituted $C_{1-5}$ alkylene and optionally substituted hetero $C_{1-5}$ alkylene;
each R⁵ is the same or different and is selected from the group consisting of optionally substituted $C_{1-10}$ alkyl and optionally substituted hetero $C_{1-10}$ alkyl, optionally two R⁵ may be joined to form a ring;
R⁶ is selected from the group consisting of optionally substituted $C_{1-10}$ alkylene and optionally substituted hetero $C_{1-10}$ alkylene; and
R⁷ is a reactive group.

7. The compound of claim 6, wherein:
R³ is optionally substituted $C_{1-10}$ alkyl;
X is O or N;
R⁴ is absent or $C_{1-5}$ alkylene;
each R⁵ is the same or different and is selected from the group consisting of optionally substituted $C_{1-10}$ alkyl and optionally substituted hetero $C_{1-10}$ alkyl, optionally two R⁵ may be joined to form a ring;
R⁶ is selected from the group consisting of optionally substituted $C_{1-10}$ alkylene and optionally substituted hetero $C_{1-10}$ alkylene; and
R⁷ is a reactive group.

8. The compound of claim 6, wherein:
R³ is optionally substituted $C_{1-5}$ alkyl;
X is O or N;
R⁴ is absent or $C_{1-5}$ alkylene;
each R⁵ is the same or different and is selected from the group consisting of optionally substituted $C_{1-5}$ alkyl and optionally substituted hetero $C_{1-5}$ alkyl, optionally two R⁵ may be joined to form a ring;
R⁶ is optionally substituted hetero $C_{1-10}$ alkylene; and
R⁷ is a reactive group.

9. The compound of claim 6, wherein the compound is selected from the group consisting of:

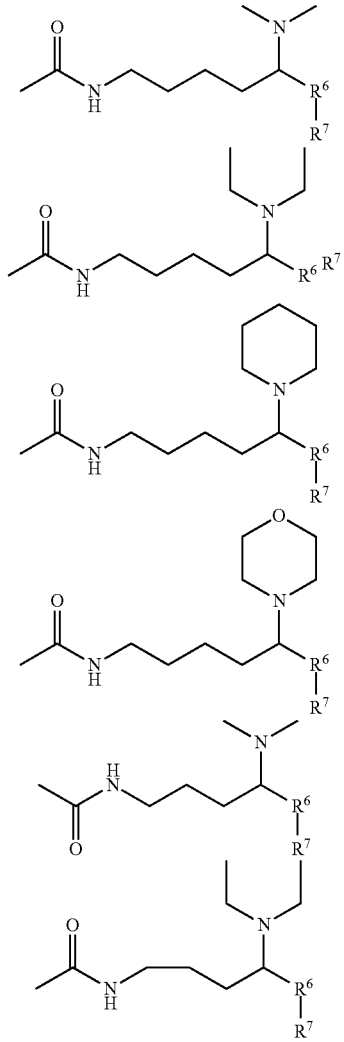

-continued

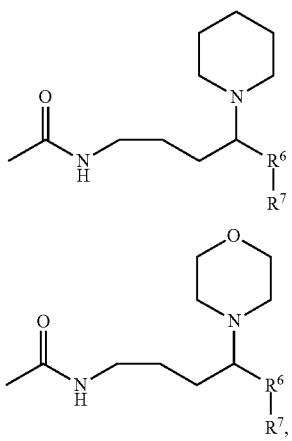

and isotopic isomers thereof.

10. The compound of claim 6, wherein the compound is selected from the group consisting of:

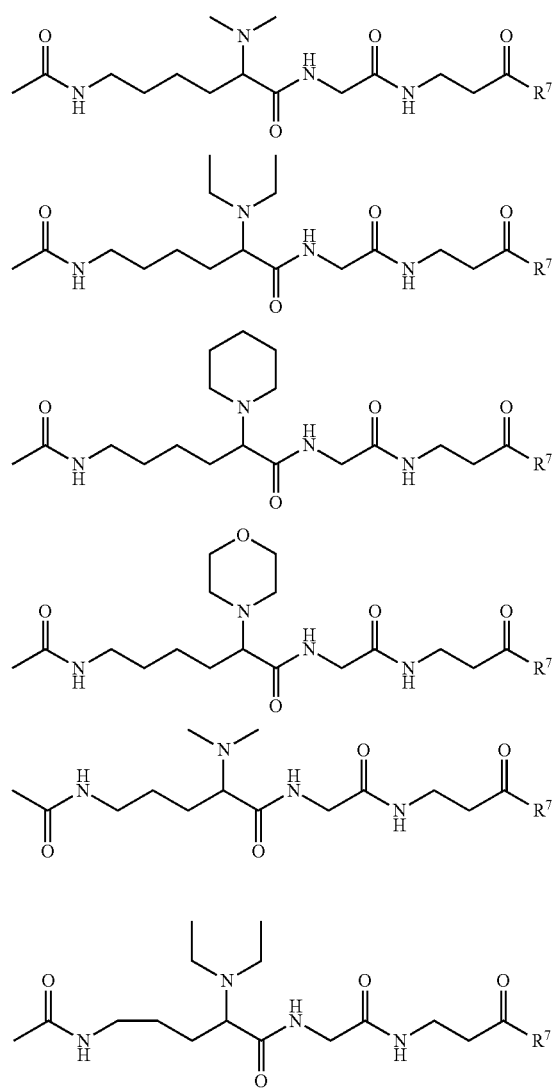

-continued

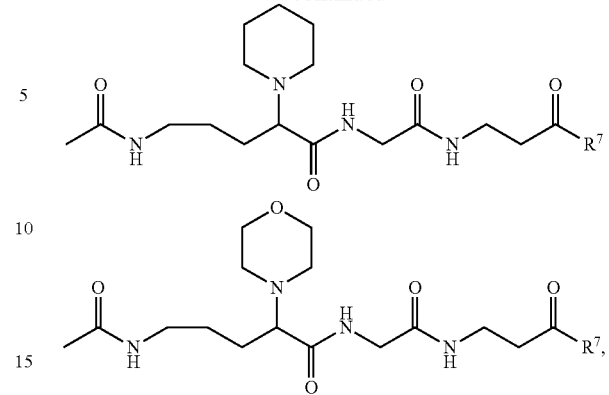

and isotopic analogues thereof.

11. The compound of claim 1, wherein the compound is selected from the group consisting of:

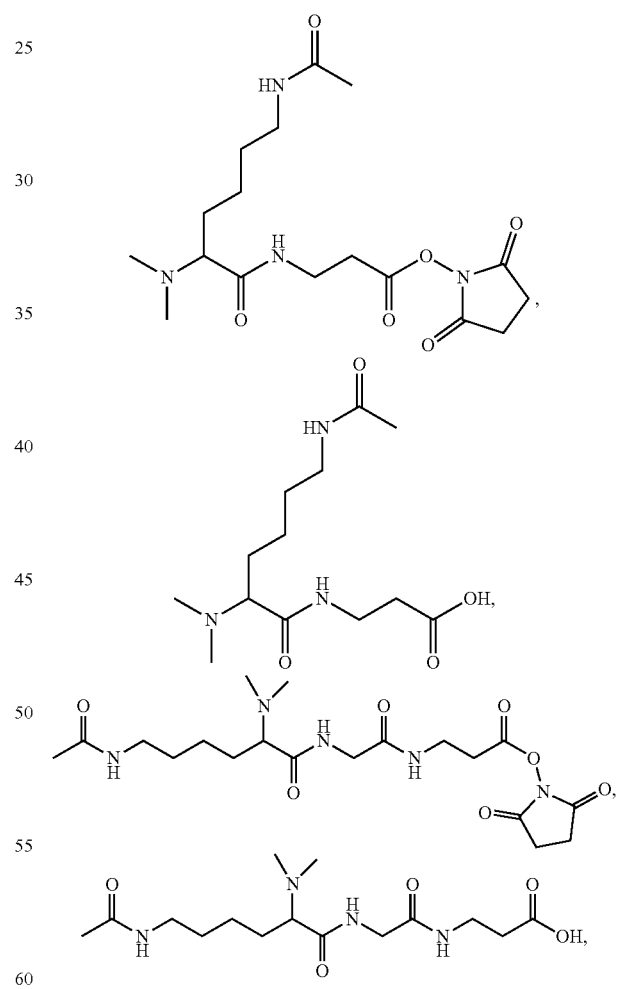

and isotopic isomers thereof.

12. The compound of claim 1, wherein $R^7$ is selected from the group consisting of optionally substituted heteroalkyl, substituted cycloheteroalkyl, optionally substituted heteroalkenyl, optionally substituted heteroaryl, alcohol, optionally substituted amino, optionally substituted acyl, optionally substituted thiol, hydroxysuccinimide, and hydroxysulfosuccinimide.

13. The compound of claim 1, wherein $R^1$ is optionally substituted acyl.

14. The compound of claim 1, wherein Z is —NH—.

15. The compound of claim 1, wherein E is optionally substituted amino.

16. The compound of claim 1, wherein $R^4$ is optionally substituted alkylene.

17. The compound of claim 1, wherein $R^6$ is —C(O)—N-alkyleneC(O)O—.

18. The compound of claim 1, wherein:
$R^1$ is —C(=O) $R^2$, where $R^2$ is selected from the group consisting of optionally substituted alkyl, optionally substituted heteroalkyl, optionally substituted aryl, and optionally substituted heteroaryl;
Z is —NH—;
$R^4$ is optionally substituted alkylene;
E is optionally substituted amino;
$R^6$ is —C(O)—N-alkyleneC(O)O—; and
$R^7$ is selected from the group consisting of optionally substituted heteroalkyl, substituted cycloheteroalkyl, optionally substituted heteroalkenyl, optionally substituted heteroaryl, alcohol, optionally substituted amino, optionally substituted acyl, optionally substituted thiol, hydroxysuccinimide, and hydroxysulfosuccinimide.

19. The compound of claim 13, wherein $R^7$ is selected from the group consisting of optionally substituted amino, optionally substituted thiol, optionally substituted acyl, hydroxysuccinimide, and hydroxysulfosuccinimide.

20. The compound of claim 1, wherein the isotopic analogue thereof comprises $^2H$, $^{13}C$, $^{15}N$, $^{18}O$, $^{18}F$, $^{33}S$, and/or $^{34}S$.

* * * * *